United States Patent [19]

Soares et al.

[11] Patent Number: 5,830,662

[45] Date of Patent: Nov. 3, 1998

[54] METHOD FOR CONSTRUCTION OF NORMALIZED CDNA LIBRARIES

[75] Inventors: Marcelo B. Soares, New York, N.Y.; Argiris Efstratiadis, Englewood, N.J.

[73] Assignee: The Trustees of Columbia University in the City of New York, New York, N.Y.

[21] Appl. No.: 619,542

[22] PCT Filed: Sep. 23, 1994

[86] PCT No.: PCT/US94/10821

§ 371 Date: Jun. 21, 1996

§ 102(e) Date: Jun. 21, 1996

[87] PCT Pub. No.: WO95/08647

PCT Pub. Date: Mar. 30, 1995

Related U.S. Application Data

[63] Continuation-in-part of Ser. No. 126,594, Sep. 24, 1993, Pat. No. 5,482,845.

[51] Int. Cl.$^6$ .............. C12Q 1/68; C12P 19/34; C07H 21/04

[52] U.S. Cl. ............. 435/6; 435/91.1; 536/23.1; 536/25.4

[58] Field of Search ............. 435/91.1, 6; 536/23.1, 536/25.4

[56] References Cited

U.S. PATENT DOCUMENTS 5,482,845  1/1996  Soares et al. ............. 435/91.1
5,637,685  6/1997  Soares et al. ............. 536/23.1
5,702,898  12/1997 Bonaldo et al. ............. 435/6

OTHER PUBLICATIONS

Ko, M.S.H., An 'equalized cDNA library' by the reassociation of short doubled–stranded cDNAs, Nucleic Acids Research, 18(19): 5705–5711 (1990).

Patanjali, S.R., et al., Construction of a uniform–abundance (normalized) cDNA library, Proc. Natl. Acad. Sci. U.S.A. 88: 1943–1947 (1991).

NTIS Progress Report, Soares & Efstratiadis, Oct. 1992; and.

Sasaki, Yasnory F., et al., Construction of a normalized cDNA library by introduction of a semi–solid mRNA–cDNA hydridization system, Nucleic Acids Research, 22(6): 987–992, (1994).

*Primary Examiner*—Kenneth R. Horlick
*Attorney, Agent, or Firm*—John P. White; Cooper & Dunham LLP

[57] ABSTRACT

This invention provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to appropriate Cot; and (e) purifying the unassociated single-stranded circles, thereby generating a normalized cDNA library. This invention also provides normalized cDNA libraries generated by the above-described method and uses of the generated libraries.

25 Claims, 19 Drawing Sheets cDNA LIBRARY NORMALIZATION

FIGURE 9A

```
CDNA7A   TCTGTGTGAAGGAGAGGGTGAGGAAGAGAGAGGAATACTAAAGTTAAAACGTCACAAAGTG
CDNA7B   ..........................................TTATCCATTCCTTTTGGCCCT

CDNA7A   CTGCTTTTACAGGGAAGCTTATTCTGTTTAAACATTGAAAAGTTGTGGTCTGATCAGTTAAT
CDNA7B   GCAGCATGTCATGCTCCCAGAATTTCAGCTTAACTGACAGATGTAAAGCTTTCTGG

CDNA7A   TTGTATGTAGCAGTGTATGCTCTCATATACAATTACTGACCTATGCTCTAAAACATGAATGCT
CDNA7B   TTAGATTCTTTTCACTTGGTGATCATGTCTTTTCCATGTGTACCTGTAATATTTTTCCATCAT

CDNA7A   TTGTTACAGACCCAAGCTGTCCATTCTCTGTGATGGGTTTTGAATAAAGTATTCCCTGTCTTA₁₈
CDNA7B   ATCTCAAAGTAAAGTCATTAACATCA₁₈
```

FIGURE 9B-1

```
13-λ17    TCTAGAGTTTAGTCCTACTGTCTCTCACTCGTCTCGTTACCCAGGGCTCTGCAGCACCTCACCT    63
cDNA17A   ................................................................

13-λ17    GAGACCCTCCACTCCACATCTGCATCACTCATGGAACACTCATGTCTGGAGTCCCCTCCAG   126
cDNA17A   ............................................................

13-λ17    CCGCTGGCAACAACAGCTTCAGTCCATGGGTAATCCGTTCATAGAAATTGTGTTGCTAACAA   189
cDNA17A   ..............................................................

13-λ17    GGTGCCCTTAGCCAGATGCTAGGCTGTCTGCGAAGAAGGCTAGGAGTTCATAGAAGGGAGTG   252
cDNA17A   ..............................................................

13-λ17    GGGCTGGGGAAAGGGCTGGCTGCAATTGCAGCTCACTGCTGCCTCTGAAACAGAAAGTTG   315
cDNA17A   ..............................................................

13-λ17    GAAAGGAAAAAGAAAAAAGCAATTAGGTAGCACAGCACTTTGGTTTTGCTGAGATCGAAGAG   378
cDNA17A   .......A₁₈
```

FIGURE 9B-2

```
13-λJ7    GCCAGTAGGAGACACGACAGCACACAGTGGATTCCAGTGCATGGGGAGGCACTCGCTGTTA    441
13-λJ7    TCAAATAGCGATGTGCAGGAAGAAAAGCCCCTCTTCATTCCGGGAACAAAGACGGGTATTGT    504
13-λJ7    TGGGAAAGGAACAGGCTTGGAGGGAAGGAGAGAAGTAGGCCGCTGATGATATTCGGGCAGG    567
13-λJ7    ACTGTGTGGTACTGGCAATACACAGCTCCGAGCTGTAGGAGAGTCGGTCTGCTTTGG      630
13-λJ7    ATGATTTTTAAGCAGACTGCTATCACATTTTATTAAACACAGGGAAAGCAT          693
13-λJ7    TTAGGAGAATAGCAGAGAGCCAAATCTGACCTAAAGTTGAAAAGCCAAAGGTCAAACAGGCT 756
13-λJ7    GTAATTCCATCATCATCGTTGTATTAAAGAATCCTTATCTATAAAGGTAGTCAGATCCCC   819
13-λJ7    CTCCCCCCAGTTCCTCCTCCCCCGATTGAGCCTTACGACACTTTGGTTTATGCGGTGC     882
13-λJ7    TGTCCGGGTGCCAGGGCTGCAGGGTCGGTACTGATGGAGCCTGCAGCGCCCGGTCTCTGTGT 945
13-λJ7    CAAGGTGAAGCACATACGGCAGACCCTCTTAAGACGAAGTAATTATGATGTCC          1008
13-λJ7    AGGGGAGAAGGAAGATAGGACGTATTTATATAGAACACAACAAGGATATAAAATG       1071
13-λJ7    AAAGATTTTACTAATATATTTTAAGGTTGCACACAGTACACACCAGAAGATGAAATTC    1134
13-λJ7    ATTTGTGCAATTAAGTGGTCCCAATGCTCAGCGCTTAAAAAACAAATTGGACAGCTACTTC 1197
cDNA17B   ................................................................

13-λJ7    TGGGAAAAACAACATCATTCCAAAAGAACAATATGCAAAATAACCAAGTC            1260
cDNA17B   ..................................................

13-λJ7    CTCCGAAGGCATTCACGGAACCGTAGACTAGGAAGTACGAGCCCCACAGAGCAGGAAGCCGA 1323
cDNA17B   ..............................................................

13-λJ7    TGTGACTGCATCATATATTTAACAATGACAAGATGTTCCGGCGTTTATTTCTGCGTTGGGTTT 1386
cDNA17B   ..................................................................

13-λJ7    TCCCTTGCCTTATGGGCTGAAGTGTTCTCTAGA                              1419
cDNA17B   .................................
```

FIGURE 9C

```
cDNA26-3   TTGTCTTTTGATCTTTTATTCTGAAACACTCAAACACCTTACAAAGTGCTGAGTAGTAATA
cDNA27-3   ...........................................................

cDNA26-3   GTGACCCAACTGTTGCTAAATGATTATTGTTAAATCTGTACAGTTTTAAGTGTTCACTT
cDNA27-3   ............................................................

cDNA26-3   ATACAAAGAGTGTATATACTTTCAAATAATTTAAAATGCTTTATATTAT--GGCTAGAAATTG
cDNA27-3   ....................................................TT......

cDNA26-3   CTGTTTTTAATAAATGTGAATTTTTTAAAATAAAGATTTTGCTTCCTA₁₈
cDNA27-3   ........AATAAA...........................A₁₈
```

FIGURE 10A

```
                                             353
                                             Val Gly Ile Asn Tyr Gln Pro Pro Thr Val Val Pro Gly Gly Asp Leu Ala 369
         tt ctc cgg cag                      GTG GGC ATT AAC TAC CAG CCC CCC ACG GTG GTC CCT GGG GGA GAC CTG GCC
TUBA2    ..  ... ... t..                     ... ... ... ... ... ... ... ... ..A ... ... ..C ... ... ... ... ...
H2-α     352
         Cys Pro Thr Gly Phe Lys
         347
         TGC CCC ACA GGC TTC AAG             ..T ..C ... ... ... ..T ..T ... ..T ..G ... ... ... ..T ... ... ...
Hα44     ..T ..C ... ... ..T ...

Lys Val Gln Arg Ala Val Cys Met Leu Ser Asn Thr Thr Ala Ile Ala Glu Ala Trp Ala Arg Leu Asp 392
TUBA2    AAG GTG CAG CGG GCT GTG TGC ATG CTG AGC AAC ACC ACG GCC ATC GCG GAG GCC TGG GCT CGC CTG GAC
H2-α     ... ... ... ... ... ... ... ... ... ... ... ..G ... ... ..T ... ... ..C ... ... ... ... ...
Hα44     ..T ..C ... ... ..C ..C ... ... ... ... ... ... ... ... ..T ..C ... ..C ... ..C ..C ... ...
```

FIGURE 10B

```
       His Lys Phe Asp Leu Met Tyr Ala Lys Arg Ala Phe Val His Trp Tyr Val Gly Glu Gly Met Glu Glu
                                                                                              415
TUBA2  CAT AAG TTC GAT CTC ATG TAT GCC AAG CGG GCC TTT GTG CAC TGG TAC GTG GGA GAA GGC ATG GAG GAG
H2-α   ... ... ... ..C ..G ... ... ... ... ..T ... ... ... ... ... ..T ... ..C ... ... ... ... ..A
Hα44   ..C ... ... ... ... ... ... ... ... A.. ..G ... ... ... ... ... ... ..T ..G ... ... ... ...

Gly Glu Phe Ser Glu Ala Arg Glu Asp Leu Ala Ala Leu Glu Lys Asp Tyr Glu Glu Val Gly Val Asp
                                                                                              438
TUBA2  GGG GAG TTC TCT GAG GCC CGC GAG GAC CTG GCA GCT CTG GAG AAG GAT TAT GAA GAG GTG GGC GTG GAT
H2-α   ..A ... ... ... ... ... ... ... ... ... ... ... ..A ... ... ... ... ... ... ... ... ... ...
                                           Met                                                Ile
Hα44   ..T ... ... ..C ... ... ..T ... ..T A.. ..T ..C ... ... ... ... ... ... ..G ... ... A.C ..C
```

FIGURE 10C

```
                                        445       446       450
        Ser Val Glu Ala Glu Ala Glu --- --- Glu Gly Glu Glu Tyr   *
TUBA2   TCC GTG GAA GCC GAG GCT GAA --- --- GAA GGT GAA GAA TAC TGA gggga-gggtg
H2-α    ... ... ... ..T ... ..C ... : : ... ..C ... ... ... ... : : : : : : : :
             Tyr Asp     Asp         : :     Gly
Hα44    ... TAT ..G .A. .A. .A. ..G GGA ... .AA --- --- .A. --- .A. agcagctgcct
```

FIGURE 11A

```
cDNA21      IKYMEKHKVKPDSKAFHLLQKLLTMDPIKRITSEQAMQDPYFLEDPLPTSDVFGGCQ
 1 (B40466)         K DSKA   LL ++LT +P KRIT E+A+   PY  +     PT +
 2 (S23428)         K DSKA   LL ++LT +P KRIT E+A+   PY  +     PT +
 3 (PQ0270)         K DSKA   LL ++LT +P KRIT E+A+   PY  +     PT +
 4 (A40466)         K DSKA   LL ++LT +P KRIT E+A+   PY  +     PT +
 5 (A35061)         K DSKA   LL ++LT +P KRIT E+A+   PY  +     PT +
 6 (S28184)         K DSKA   LL ++LT +P KRIT E+A+   PY  +     PT +
 7 (P27361)         K DSKA   LL ++LT +P KRIT E+A+   PY  +     PT +
 8 (S15519)         K DSKA   LL ++LT +P KRIT E+A+   PY  +     PT +
 9 (P21708)         K DSKA   LL ++LT +P KRIT E+A+   PY  +     PT +
10 (A60041)         K DSKA   LL ++LT +P KRIT E  A+   PY  +     PT +
11 (P23293)                   L +LL  +DP KR+T+  A     P+F  EDPLP+  +
12 (S23426)           DSKA   LL K+LT +P KRI  EQA+   PY  +     P+ +
13 (P27703)           DSKA   LL K+LT +P KRI  EQA+   PY  +     P+ +
14 (P28482)           DSKA   LL K+LT +P KRI  EQA+   PY  +     P+ +
15 (S23427)           DSKA   LL K+LT +P KRI  EQA+   PY  +     P+ +
16 (P29620)                A  LL ++  T DP  RIT++QA++  YFL    P  PT
17 (P16892)         +EK  + + K   LLQ++L  DP KRIT+++A++ PY
18 (S30095)         +EK  + + K   LLQ++L  DP KRIT+++A++ PY
19 (S25011)           DSKA   LL K+LT +P KRI  EQA+   PY
20 (S27423)           V P SK   L    LL  D  KR ++ +A+Q  YF E+P P   V  G
21 (M69024)           V P SK   L    LL  D  KR ++ +A+Q  YF E+P P   V  G
22 (P27638)                A  LL+KLLT +P KRIT+E+A++ PY
23 (S22008)            D      LL K+L +DP +RIT++QA++  YF E+
24 (A45091)                   LLQ LL  +P++RI++E+A+Q PYF
25 (Q03114)                   LLQ LL  +P++RI++E+A+Q PYF
26 (X66364)                   LLQ LL  +P++RI++E+A+Q PYF
27 (L04798)                   LLQ LL  +P++RI++E+A+Q PYF
28 (L00652)              D K +LL K+L  DP  RIT+  A++ PYF
29 (Q00535)                   LLQ LL  +P++RI++E+A+Q PYF
30 (P11440)         + H  D     LL K+L  DP KRI+ + A++ PYF
31 (S24913)         + H  D     LL K+L  DP KRI+ + A++ PYF
32 (A38643)               + F  L+QK+L  DP KRIT  +A++ P+F
```

FIGURE 11B-1

```
              T   N   C   S   L   I   K   Y   M   E   K   H   K   V   K   P   D   S   K   A
cDNA21B      ACC AAC TGC AGC CTT ATC AAG TAT ATG GAA AAA CAT AAA GTT AAA CCA GAT AGT AAA GCA T    61

F   H   L   Q   K   L   T   M   D   P   I   K   R   I   T   S   E   Q   A
cDNA21B      TCC ACT TGC TTC AGA AGC TGC TTA CCA TGG ACC CAA TAA AGC GAA TTA CCT CAG AAC AGG C   122

M   Q   D   P   Y   F   L   E   D   P   L   P   T   S   D   V   F   G   G   C
cDNA21B      TAT GCA GGA CCC CTA TTT CTT AGA AGA CCC ACT TCC TAC ATC AGA CGT TTT TGG CGG TTG T   183
                                                             gat cag CGT TTT TGG CGG TTG T
13-λ21

Q   I   P   Y   P   K   R   E   F   L   T   E   E   P   D   D   K   G   D
cDNA21B      CAA ATC CCT TAC CCA AAA CGA GAA TTT TTA ACG GAA GAA GAA CCT GAT GAC AAA GGA GAC A   244
13-λ21       CAA ATC CCT TAC CCA AAA CGA GAA TTT TTA ACG GAA GAA GAA CCT GAT GAC AAA GGA GAC A

K
cDNA21B      AA                                                                                  246
13-λ21       AAg taa gta tta aag tac tgt tag cag ctt ctt gtt tcg tga atg cct cca taa cat ttt c
13-λ21       cat tgt ggg tat att ttg ttc tcc ctc tga gct gaa ctt ttt ctg ttt aac caa ttg ag
```

FIGURE 11B-2

```
              K   N   Q   Q   Q   Q   G   N   N   H   T   N   G   T   G   H   P   G   N
cDNA21B      AAG AAC CAG CAG CAG CAG GGC AAT AAC CAC ACT AAT GGA ACT GGC CAC CCA GGG AAT C   307
13-λ21       AAG AAC CAG CAG CAG CAG GGC AAT AAC CAC ACT AAT GGA ACT GGC CAC CCA GGG AAT C

Q   D   S   S   H   T   Q   G   P   P   L   K   K   V   R   V   P   P   T   T
cDNA21B      AAG ACA GCA GTC ACA CAC AGG GAC CCC CGT TGA AGA AAG TGA GAG TTG TTC CTC CTA CCA C   368
13-λ21       AAG ACA GCA GTC ACA CAC AGG GAC CCC CGT TGA AGA AAG TGA GAG TTG TTC CTC CTA CCA C

T   S   G   L   I   M   T   S   D   Y   Q
cDNA21B      TAC CTC AGG TGG ACT TAT CAT GAC CTC AGA CTA TCA G                                  405
13-λ21       TAC CTC AGG TGG ACT TAT CAT GAC CTC AGA CTA TCA Ggt att cca agt tta ttt tgg gtt g
13-λ21       gac tgc atg tca gng ttt aca tat ggg ttt atg atc cgg atg aaa atg tga ttt aat tga g
13-λ21       a.. ... ... ... ... ... ... ... ...1.9 kb.. ... ... ... ... ... ... ... ... . .
13-λ21       cct ata cat cct ttc gtt gaa aca taa tga cac atc agt cac ata ttg gga ttg agc t R   S   N   P   H
cDNA21B                                                 C GTT CCA ATC CAC A                    419
13-λ21       tcc cct aga agc anc tga atc aca ctt ttc cct cat ctc ctt tcc agC GTN CCA ATC NAC A A   A   Y   P   N   P   G   P   Q   S   T   S   Q   P   Q   S   M   G   Y   S
cDNA21B      TGC TGC CTA TCC CAA CCC TGG ACC CCA AAG CAC ATC TCA GCC GCA GAG TCA CAG CAG CAG    480
13-λ21       TGC TGC CTA TCC CAA CCC TGG ACC CCA AAG CAC ATC TCA GCC GCA GAG TCA CAG CAG CAG
```

FIGURE 11B-3

|  | A | T | S | Q | Q | P | P | Q | Y | S | H | Q | T | H | R | Y | * | | | | |
|---|---|---|---|---|---|---|---|---|---|---|---|---|---|---|---|---|---|---|---|---|---|
| cDNA21B | GCT | ACC | TCC | CAG | CAG | CCT | CCA | CAG | TAC | TCA | CAT | CAG | ACA | CAT | CGG | TAC | TGA | GCT | GCA | TCG | G |
| 13-λ21 | GCT | ACC | TCC | CAG | CAG | CCT | CCA | CAG | TAC | TCA | CAT | CAG | ACA | CAT | CGG | TAC | TGA | GCT | GCA | TCG | G | 541 |
| cDNA21B | AAT | CTT | GTC | CAT | GCA | CTG | TTG | CGA | ATG | CTG | CAG | GGC | TGA | CTG | TGC | AGC | TCT | CTG | CGG | GAA | C |
| 13-λ21 | AAT | CTT | GTC | CAT | GCA | CTG | TTG | CGA | ATN | CTG | CAG | GGC | TGA | CTG | TGC | AGC | TCT | CTG | CGG | GAA | C | 602 |
| cDNA21B | CTG | GTA | TGG | GCC | ATG | AGA | ATG | TAC | TGT | ACA | ACC | ACA | TCT | TCA | AAA | TGT | CCA | GTA | GCC | AAG | T |
| 13-λ21 | CTG | GTA | TGG | GCC | ATG | AGA | ATG | TAC | TGT | ACA | ACC | ACA | TCT | TCA | AAA | TGT | CCA | GTA | GCC | AAG | T | 663 |
| cDNA21B | TCC | ACC | ACT | TTT | CAC | AGA | TTG | GGG | TAG | TGG | CTT | CCA | AGT | TGT | ACC | TAT | TTT | GGA | GTT | AGA | C |
| 13-λ21 | TCC | ACC | ACT | TTT | CAC | AGA | TTG | GGG | TAG | TGG | CTT | CCA | AGT | TGT | ACC | TAT | TTT | GGA | GTT | AGA | C | 724 |
| cDNA21B | TTG | AAA | AGA | AAG | TGC | TAG | CAC | AGT | TTG | TGT | TGT | GGA | TTT | GCT | ACT | TCC | ATA | GTT | TAC | TTG | A |
| 13-λ21 | TTG | AAA | AGA | AAG | TGC | TAG | CAC | AGT | TTG | TGT | TGT | GGA | TTT | GCT | ACT | TCC | ATA | GTT | TAC | TTG | A | 785 |
| cDNA21B | CAT | GGT | TCA | GAC | TGA | CCT | ATG | CAT | TTT | TTT | CAG | TGA | CAG | TCT | GTA | GCA | GTT | GAA | GCT | GTG | A |
| 13-λ21 | CAT | GGT | TCA | GAC | TGA | CCA | ATG | CAT | TTT | TTT | CAG | TGA | CAG | TCT | GTA | GCA | GTT | GAA | GCT | GTG | A | 846 |

METHOD FOR CONSTRUCTION OF NORMALIZED CDNA LIBRARIES

This is a national application based on PCT International Application PCT/US94/10821, filed Sep. 23, 1994 which is a continuation-in-part of U.S. Ser. No. 08/126,594 filed Sep. 24, 1993 U.S. Pat. No. 5,482,845, the contents of which are hereby incorporated in their entirety.

This invention was made with support under Grant Number DE-FG0291ER61233 from the U.S. Department of Energy. Accordingly, the U.S. Government has certain rights in the invention.

BACKGROUND

Significance of cDNA Library Normalization

A typical somatic cell contains approximately 0.6 pg of mRNA. Thus, there are about 500,000 mRNA molecules per cell assuming that the average size of a mRNA is 2 kb ($11 \times 10^7$ pg). These mRNAs occur in three frequency classes (reviewed by Davidson and Britten, 1979):

|  | % mass | # mRNA species | # copies per species | Total mRNAs |
|---|---|---|---|---|
| Superprevalent | 10 (10–20) | 10 | 5,000 | 50,000 |
| Moderately Prevalent | 45 (40–45) | 1,000 | 225 | 225,000 |
| Complex | 45 (40–45) | 15,000 | 15 | 225,000 |

Accordingly, the rarest mRNA (1 copy per cell) will be present at a frequency of $1/500,000$. Its representation in a cDNA library will depend on the number of independent recombinants. The probability that a given mRNA will be represented can be expressed by the equation $P(x)=1-(1-f)^n$, where f-frequency ($1/500,000$) and n-number of recombinant clones. Therefore, the probability that the most rare mRNA will not be represented in a cDNA library of $10^7$ recombinants is $2 \times 10^{-9}$.

Although even the rarest mRNA will be represented in a library, its identification is very difficult ($1/500,000$). In a normalized cDNA library, however, the frequency of each clone is in the same narrow range and depends on the complexity of the library.

Assuming that there are 50,000 to 100,000 genes in the human genome (Bishop et al., 1974), an ideal normalized cDNA library from a great variety of tissues containing 1–2 kb cloned inserts of every single expressed human gene would have a complexity of 50,000 to 200,000 kb, and every clone would be represented at a frequency of $1/50,000$ to $1/100,000$, which would still be 5–10 times higher than the frequency of the most rare mRNA in a single somatic cell ($1/500,000$).

According to the considerations described above, the relative frequency of a member of each class of sequences (superprevalent, moderately prevalent and complex) in a representative cDNA library of a typical cell is I:II:III=1.7 and III=25. At Cot=250 (which is 10×the $Cot_{1/2}$ of class III) of the leftover of each component, expressed as % of the initial amount, will be I=0.03%, II=0.6% and III=9%, while the relative average frequency of a member of each class will be 1:1:1, i.e., the library will be normalized.

Methods to Normalize cDNA Libraries

Thus far, two approaches have been proposed to obtain normalized cDNA libraries (Weissman, 1987). One approach is based on hybridization to genomic DNA. The frequency of each hybridized cDNA in the resulting normalized library would be proportional to that of each corresponding gene in the genomic DNA. The other is a kinetic approach. If cDNA re-annealing follows second-order kinetics, rarer species anneal less rapidly and the remaining single-stranded fraction of cDNA becomes progressively more normalized during the course of the hybridization (Galau, et al., 1977). Specific loss of any species of cDNA, regardless of its abundance, does not occur at any Cot value.

Two groups have pursued independently the construction of normalized cDNA libraries based on the kinetic approach (Ko, 1990; Patanjali et al., 1991).

Ko (1990) reported the construction of a normalized mouse cDNA library by a complex scheme involving: a) ligation of cDNAs to a linker-primer adapter; b) three rounds of PCR amplification, denaturation-reassociation, and purification of single-stranded cDNAs by hydroxyapatite (HAP) column chromatography; and c) digestion of the end product using a site present in the linker-primer sequence and cloning (#' non-coding cDNA fragments only) into a plasmid vector.

Colony hybridization with eight probes of different abundances showed a reduction in abundance variation from at least 20,000 fold in the original library to 40-fold in the library constructed after three cycles of normalization.

In Ko's method, both coding and non-coding fragments are present during reassociation. However, after the final digestion and directional cloning steps only the 3' non-coding fragments remain in the normalized library. Ko's rationale for constructing a normalized library consisting exclusively of 3' non-coding sequences was the following. The 3' non-coding terminal exon of a mRNA is almost always unique to that transcript. Thus, during the reassociation step, each 3' non-coding sequence is expected to only re-anneal to its very complementary strand. In contrast, coding exons may be conserved among members of a gene family, some of which might be less represented than others in a given tissue. Thus, during reassociation, the most frequent of such coding sequences might cross-hybridize to a related, but divergent, complementary strand from a less prevalent family member, which could result in the elimination of the rarer family member from the normalized library.

Patanjali et al. (1991) obtained a normalized library by a similar method which involved: a) cloning of short cDNAs produced by random priming into λgt10; b) PCR amplification of cloned DNAs; c) denaturation and reassociation to moderate Cot; d) separation of single-strands by HAP chromatography; e) PCR amplification of HAP-flow-through single-stranded cDNAs; and f) cloning into λgt10.

Patanjali's normalized library consisted of cDNA clones containing both coding and non-coding information. However, the cDNAs had to be relatively short and homogenous in length to assure equal efficiency of amplification during the polymerase chain reactions. The potential problem mentioned above of losing sequence representation of rare gene family members in the normalized library was not addressed in Patanjali's approach.

SUMMARY OF THE INVENTION

This invention provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and re-associating the purified partial duplexes to appropriate Cot; and (e) purifying the unassociated single-stranded circles, thereby generating a normalized cDNA library.

This invention also provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to appropriate Cot; and (e) purifying the unassociated single-stranded circles, thereby generating a normalized cDNA library, wherein the directional cDNA library is generated by using a primer having a rare restriction enzyme recognition site for the first strand cDNA synthesis, upstream of the oligodT stretch.

This invention further provides normalized libraries generated by the above methods.

The cDNA library in the form of single-stranded circles is annealed to a ½NotI-(dT) oligonucleotide (arrow) and controlled extensions are performed with Klenow in the presence of a 25-fold excess ddNTPs (each A-C-G) over dNTPs (each A-C-G-T). Partially duplex circular molecules are purified from remaining single-stranded circles by hydroxyapatite column chromatography. HAP-bound DNA containing the partially double-stranded circles is melted and re-associated to moderate Cot value. The remaining single-stranded circles (normalized library) are purified from the re-associated material by HAP chromatography, converted to partial duplexes by primed extension and electroporated into competent DH10B bacteria, thus generating a normalized library containing large size cDNA inserts.

Figure 2:
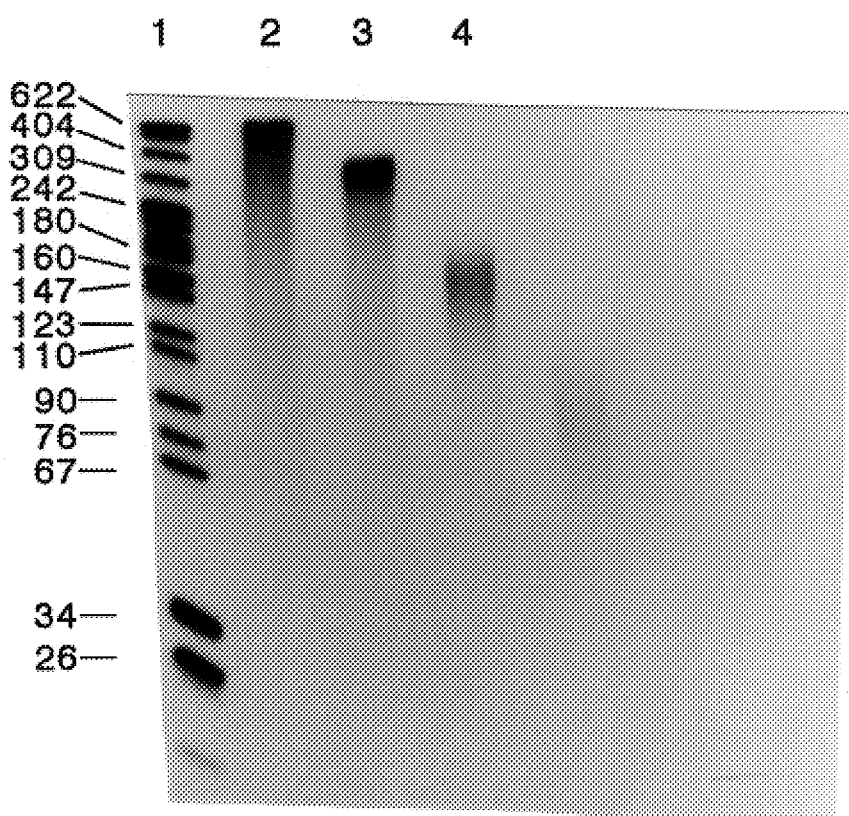

FIG. 2 Controlled Primed Extensions with Klenow Enzyme in the Presence of Different Ratios of dNTPs:ddNTPs.

Controlled primed extension of the single-stranded brain cDNA library with the Klenow enzyme in the presence of a 15-fold, 20-fold or 25-fold excess of ddNTPs (A-G-C) over dNTPs (lanes 2, 3 and 4, respectively). The oligonucleotide utilized as primer was the ½NotI-(dT)15. Lane 1. pBR322/MspI-digested.

Figure 3:
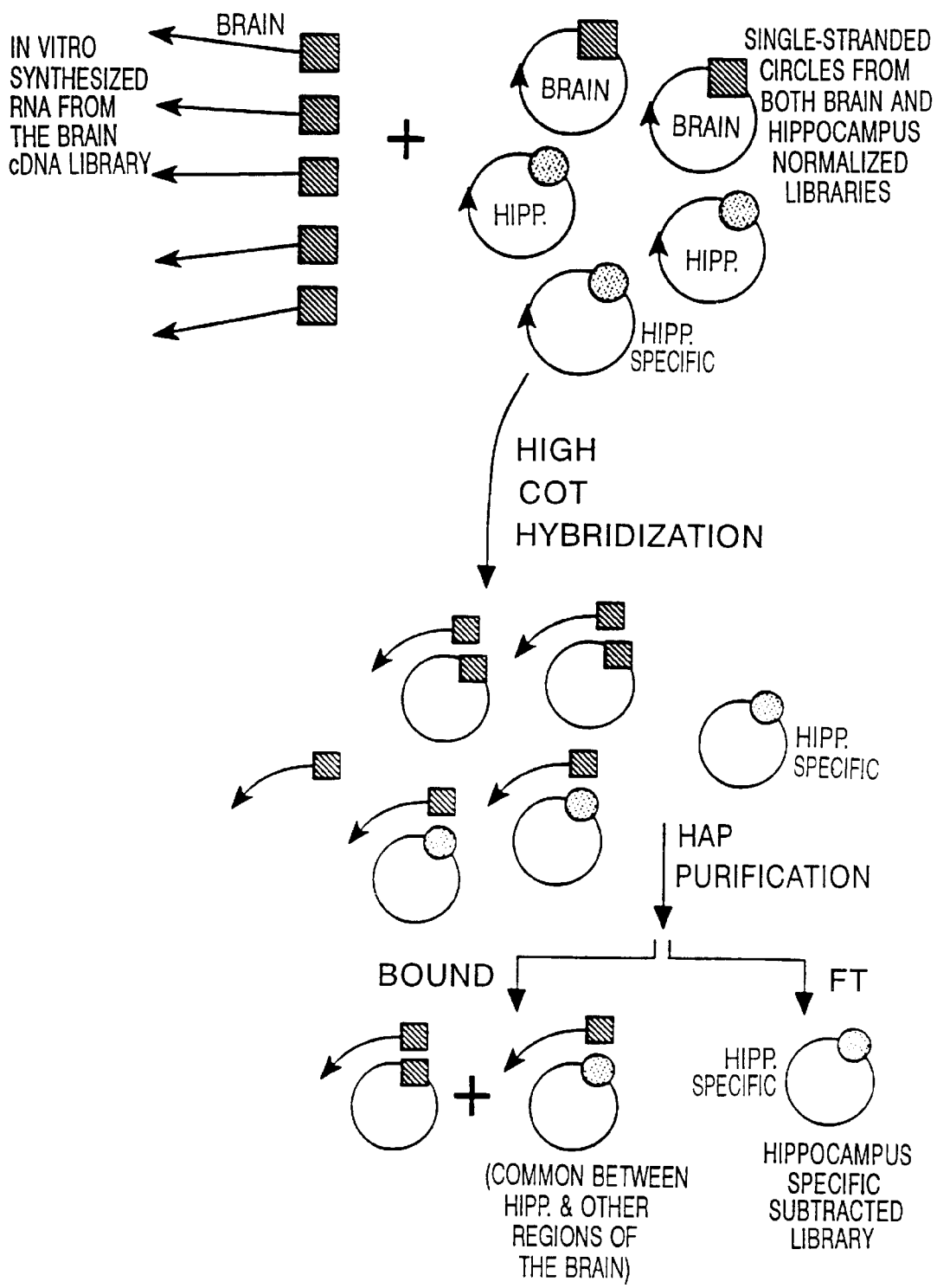

FIG. 3 Model System for Performance of Subtractive Hybridization: Application to the Isolation of Hippocampus-specific cDNAs.

In vitro synthesized RNA from the brain cDNA library (see the text; this library represents all regions of the brain with the exception of hippocampus) Single-stranded circles from both brain and hippocampus normalized libraries (see the text). Hippocampus specific subtracted library.

Figure 4:
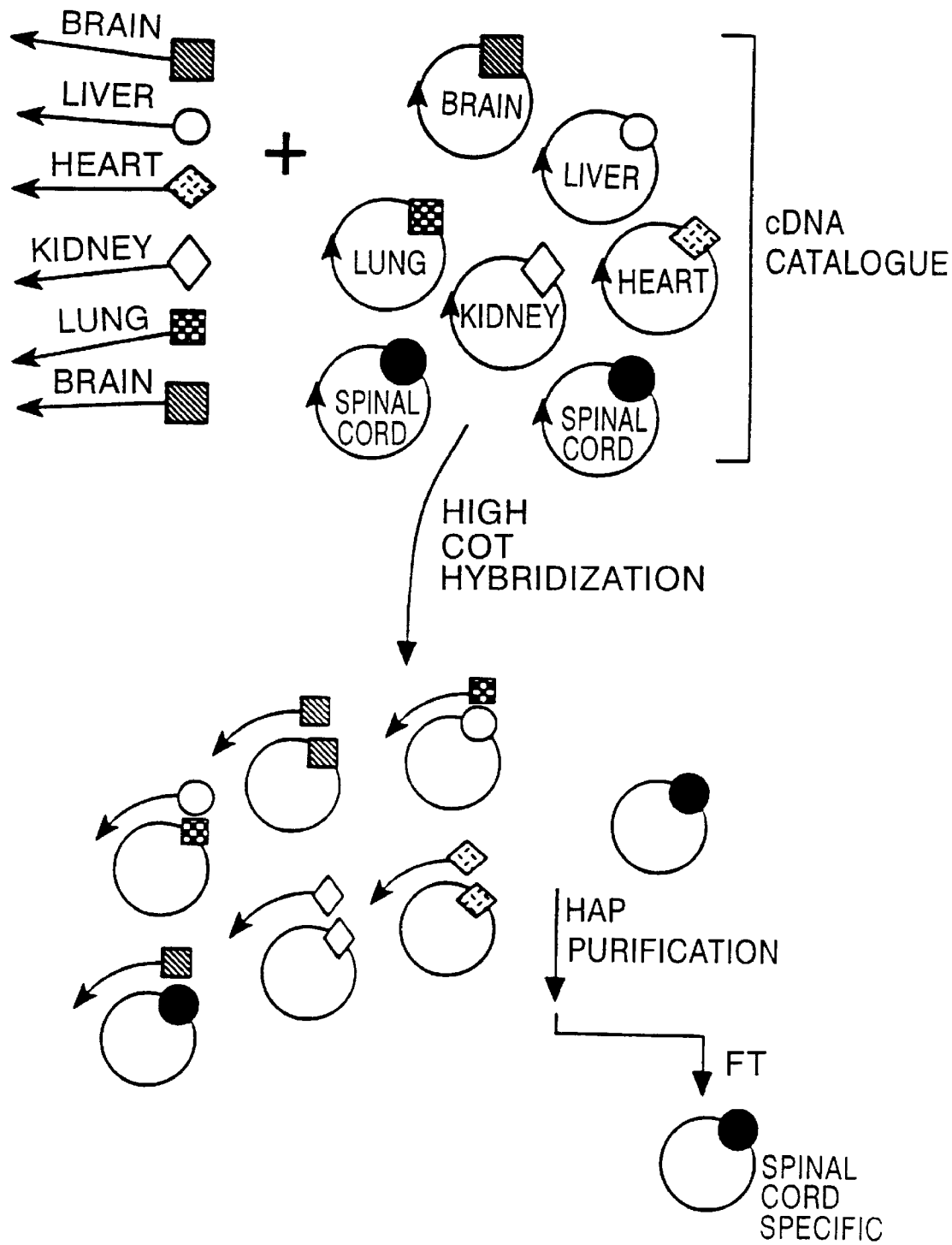

FIG. 4 Subtractive hybridizations involving RNA from combinations of normalized libraries and single-stranded circles from the cDNA catalogue. In FIG. 41 a spinal cord-specific library is isolated.

In vitro synthesized RNA from all individual normalized libraries (except spinal cord, in this example) will be hybridized to the cDNA catalogue in the form of single-stranded circles. After purification of the remaining single-stranded circles by HAP chromatography and conversion to partially duplex circular molecules for improvement of electroporation efficiencies, the subtracted library can be propagated in bacteria. All clones from this subtracted library should have the sequence identifier of the spinal cord library.

Figure 5:
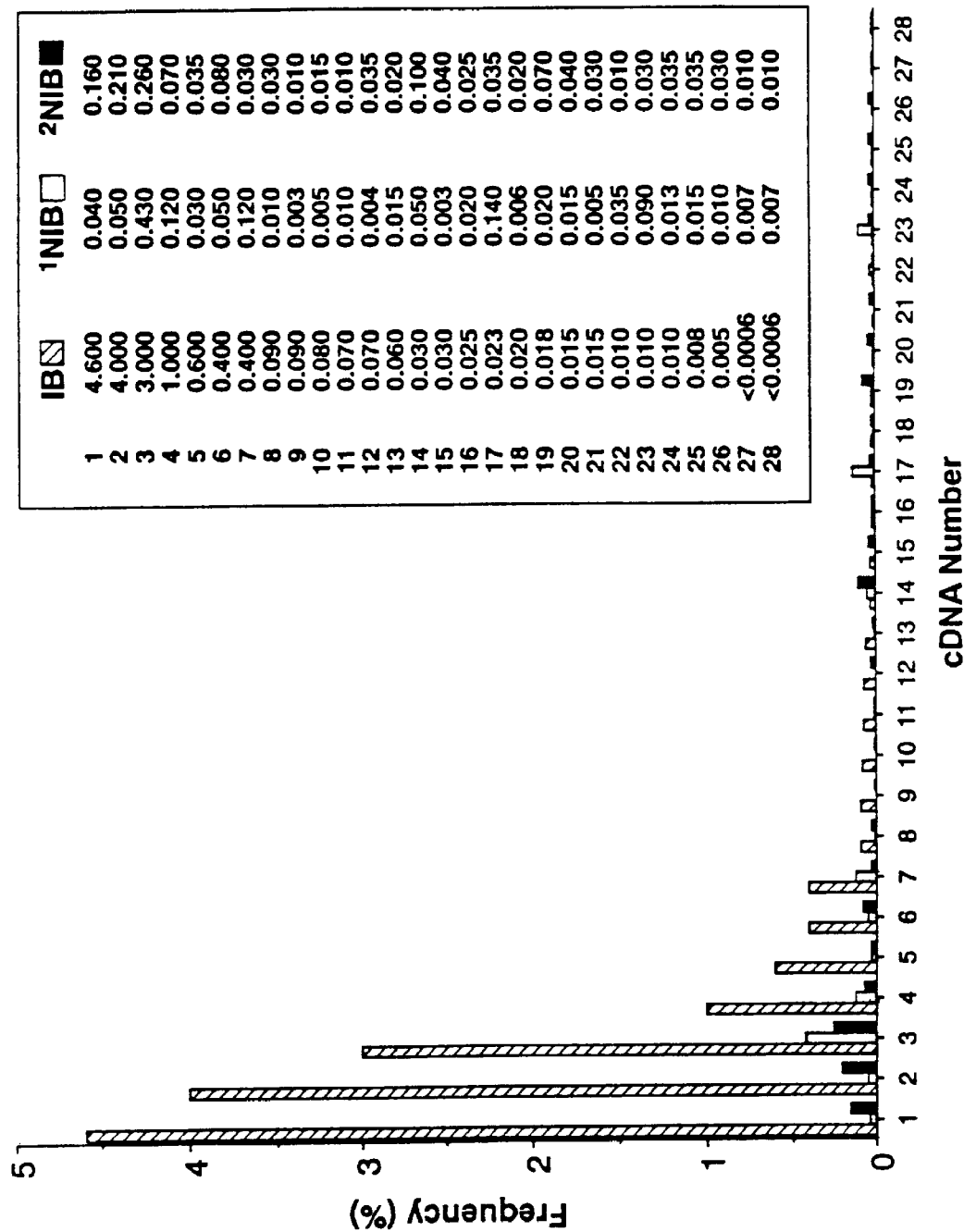

FIG. 5 Comparison of the frequencies of cDNA probes in the original (IB) and two normalized ([1]NIB and [2]NIB) libraries. The indicated percentages of 28 cDNA sequences in the three libraries, tabulated in order of decreasing frequency in the IB library, are shown in the form of a histogram to visualize normalization. Frequencies were calculated from the number of positive colonies after hybridization of duplicate filters containing 500–180,000 colonies from each of the three cDNA libraries with the following 28 probes: [1] elongation factor 1α; [2] α-tubulin; [3] β-tubulin; [4] myelin basic protein; [5] aldolase; [6] heat shock protein 89; [7] γ-actin; [8] secretogranin; [9] microtubule associated protein; [11] vimentin; [13] a cDNA randomly pricked from the [1]NIB library similar to a mouse cysteine-rich intestinal protein ([1]NIB-2, accession numbers T09996 and T09997); [19] a cDNA isolated from the [1]NIB library homologous to the human endogenous retrovirus RTVLH2 (cDNA-20, accession numbers L13822 and L13823); [20] histone H2b.1; [23] a cDNA randomly picked from the [1]NIB library encoding the human polyposis (DP1 gene) mRNA ([1]NIB-227, accession numbers T10266 and T10267; [27] a cDNA randomly picked from the [1]NIB library related to the human endogenous retrovirus ERV9 gene ([1]NIB-114, accession numbers T10086 and T10087). The remaining brain cDNAs are novel, and except for [10], [18], [21] and [25], they were randomly picked from the [1]NIB library.

Figure 6:
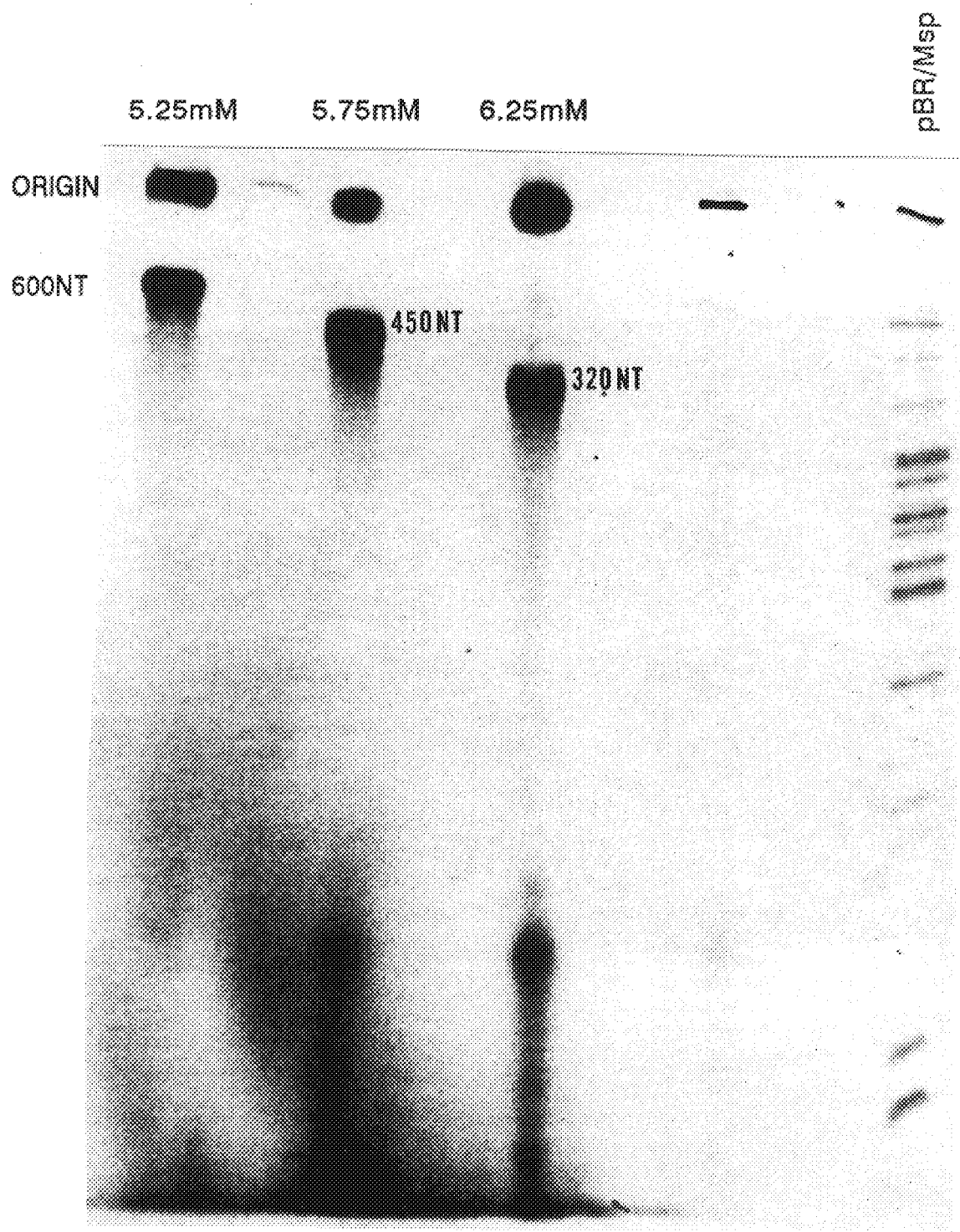

FIG. 6 Shows the results of a titration experiment in which primer extension reactions were carried out with 1 mM dNTPs and increasing amounts (5.25 mM, 5.75 mM and 6.25 mM) of each ddATP, ddCTP and ddGTP.

Figure 7:
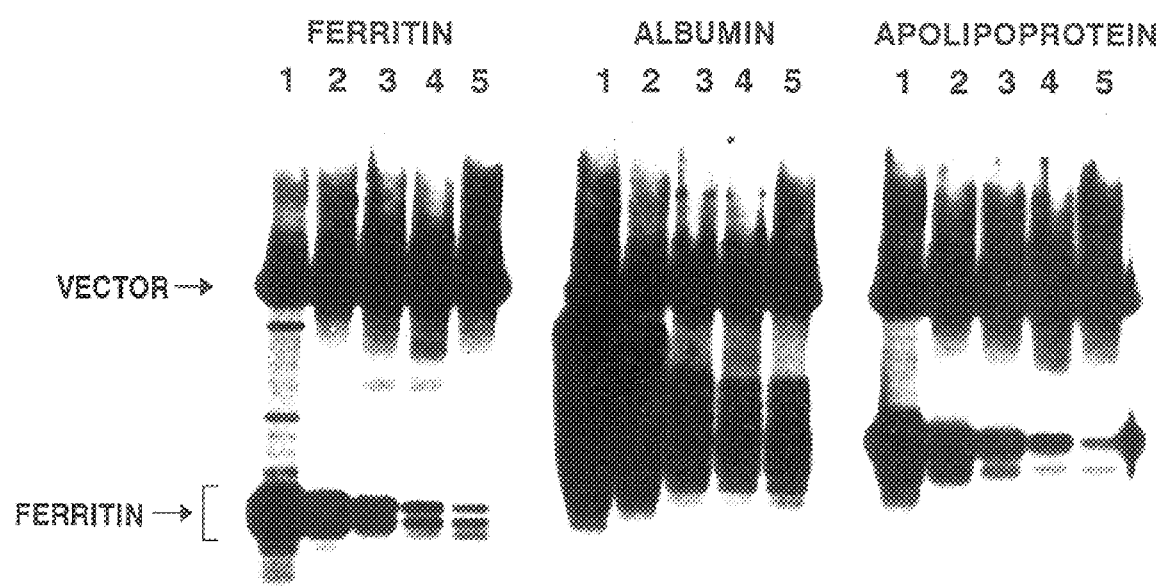

FIG. 7 A second cycle of normalization was then performed as follows: single-stranded circles from the [1]Cot 0.5 library was subjected to the normalization protocol and as before while reassociation was taking place aliquots were taken at [2]Cot 0.5, [2]Cot 5 and [2]Cot 20. Each sample was then processed, thus generating three additional normalized libraries. The libraries obtained after this second cycle were evaluated by Southern hybridzation with cDNA probes as follows: plasmid DNA from the starting library, [1]Cot 0.5 library, as well as [2]cot 0.5, [2]Cot 5 ad [2]Cot 20 libraries was doubly digested to release inserts from vector sequences, electrophoresed on agarose gels ad Southern transferred to nylon membranes. These filters were then hybridized with cDNA probes for ferritin, albumin and apolipoprotein. The results clearly indicated that the higher the Cot the lower the frequency of each of these three sequences in the respective resulting normalized library. Accordingly, the [2]Cot 20 library was considered to be the best one.

Figure 8:
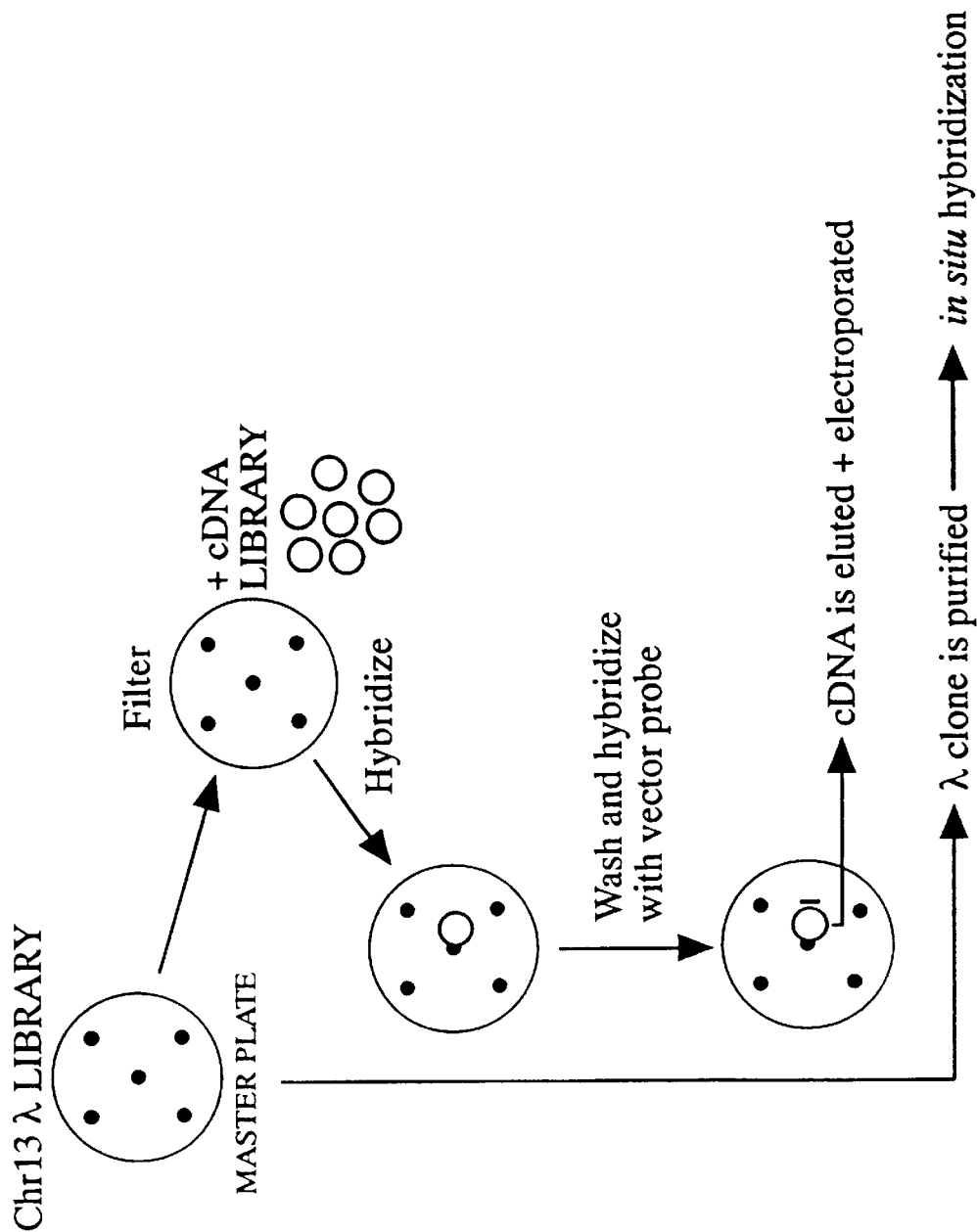

FIG. 8 Selection of cDNAs using chromosome-specific genomic clones.

Clones from a Chr 13 λ library are arrayed on a lawn of bacteria. A filter lift of this master plate is hybridized to a directionally cloned cDNA library in the form of single-stranded circles. The filter is washed and subsequently hybridized with a vector probe for visualization of cDNA/λ pairs by autoradiography. Small pieces of filter exhibiting single positive hybridization signals are cut out and treated with NaOH for elution of hybridizing cDNA circles, which are then partially converted to double-strands and electroporated into bacteria. The corresponding λ clones, which have unique addressed on the master plate, are amplified and their DNAs are used as probes for chromosomal localization by in situ hybridization.

FIGS. 9A–9C Cases of selection of two different cDNAs by a single genomic clone.

(A) Comparison of the 3' end sequences of cDNAs 7A SEQ ID NO:27 and 7B SEQ ID NO:28 (α-tubulin; Genbank accession numbers L13808 and L13810, respectively) encompassing the last 39 nucleotides of the carboxy terminal coding region and entire 3' noncoding region. Dots represent nucleotide identities. The TAA termination codon and the AAUAAA (and AGUAAA) polyadenylation signal sequences are underlines.

(B) Partial nucleotide sequence of the gene on 13-λ17 SEQ ID NO:29 (a 1,419 bp XbaI fragment; Genbank accession number L13838) and alignment with its cognate cDNAs 17A SEQ ID NO:30 and 17B SEQ ID NO:31 (3' and 5' terminal sequences, respectively; genbank accession numbers L13818 and L13821). The 3' end A-track present in cDNA 17a does not correspond to the bona fide poly(a) tail of its corresponding mRNA (priming of 1st strand cDNA17A apparently occurred at the underlined internal A-rich cluster). Dots is represent nucleotide identities.

(C) Partial nucleotide sequences cDNA 23-3 (SEQ ID NO: 32) and cDNA 27-3 (SEQ ID NO: 33) derived from the 3' ends of cDNAs 26A and 26B (Genbank accession numbers L13834 and L13836). The alternative polyadenylation signal sequences are underlined. The dashed lines represent a deletion of two nucleotides in the sequence of cDNA126A. Nucleotide identities are represented by dots.

FIGS. 10A–C The α-tubulin gene on chromosome 13 encodes a testis-specific isotype.

(A) Sequence comparisons between a partial nucleotide sequence of the α-tubulin gene on 13q11 (TUBA2 SEQ ID NO:34; Genbank accession number L11645) and the sequences of two previously identified human genes. H2α SEQ ID NO:36 (Villasante et al., 1986) and Hα44 SEQ ID NO:35 (Dobner et al., 1987) are shown. The amino acids TUBA2, SEQ ID NO: 35; H2α, SEQ ID NO: 37; and Hα44, SEQ ID NO: 39 that are characteristic of the testis-specific human genes TUBA2 and H2α are underlined. The dashed line represents deletions which were introduced to maximize homology; dots indicate sequence identity to the TUBS2 gene. Coding sequences are in capital letters; intron and noncoding exon sequences are in lower case letters. An intron between the codons for amino acids 352 and 353 is present in both TUBA2 and H2α genes.

FIG. 11A Homology between the putative polypeptide encoded by cDNA21B SEQ ID NO:40 and various protein kinases SEQ ID NOS:41–43.

Conservative amino acid replacements are indicated by (+), while blank spaces denote differences. The invariant arginine (R) residue is underlined. Although the blastx search revealed a homology to 100 protein kinases, only the top 32 matches are shown. They include: Human (2,3,7,8,), mouse (1,6), rat (5,9) and Chinese Hamster (10) Ca++/Calmodulin dependent extracellular signal-regulated protein kinase ERK1; yeast CDC28-related protein kinase SGV1 (11); human 40 kDa protein kinase (12); rat (13), human (14) and bovine (19) extracellular signal-regulated protein kinase-ERK2; human 41 kDa protein kinase (15), rice CDC2/CDC28-related protein kinase (16), yeast mitogen-activated protein kinase FUS3 (17,18), yeast CTD large subunit protein kinase (20,21), yeast mitogen-activated protein kinase SPK1 (22), Plasmodium falciparum protein kinase p34cdc2 (23); bovine proline-directed protein kinase (24,27); rat cell division protein kinase 5(25); human serine/threonine protein kinase (26,29); Dictyostelium discoideum crp gene product (28); mouse (30), rat (31) and human (32) cell division control protein 2 homolog. Genebank accession numbers are in parentheses.

Figure 1:
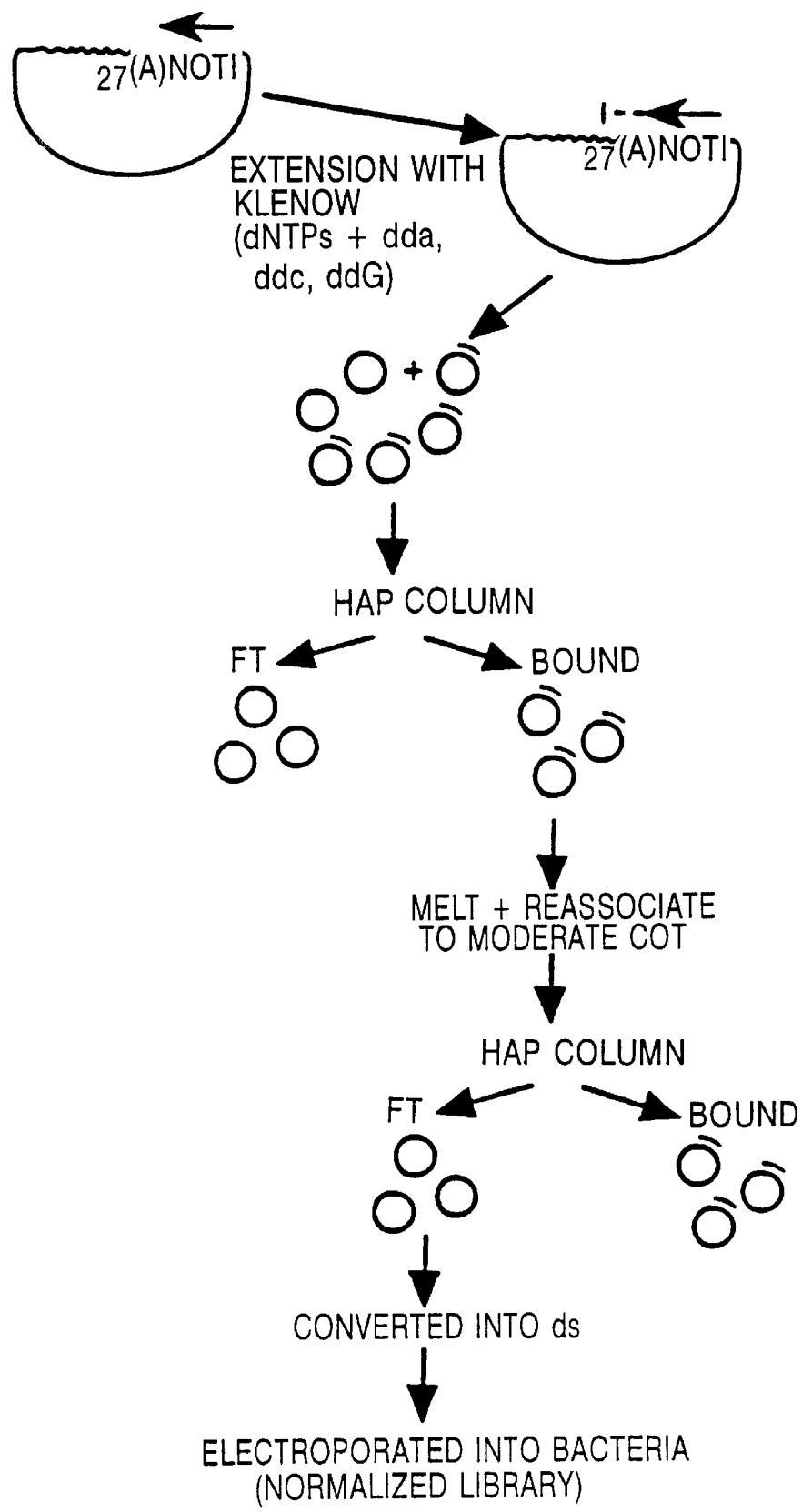
FIG. 1 Schematic Representation of the Normalization Protocol.

FIGS. 11B1–11B3 Partial nucleotide sequences of cDNA21B SEQ ID NO:44 and its corresponding genomic clone 13λ21 SEQ ID NOS:46 and 47. The nucleotide sequence obtained from the 5' end of cDNA21B (Genbank accession number L23208) is compared to that derived from the cognate region of 13-λ21 (Genbank accession numbers L30109 and L30110). The genomic sequence starts at the 5' end of the insert. Exon and intron sequences are in upper and lower case letters, respectively. The partial protein sequence SEQ ID NO:45 (1-letter amino acid abbreviations) is shown. PCR primer sequences (STS21; Table 4) are underlined.

DETAILED DESCRIPTION OF THE INVENTION

This invention provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to appropriate Cot; and (e) purifying the unassociated single-stranded circles, thereby generating a normalized cDNA library.

This invention also provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to appropriate Cot; and (e) purifying the unassociated single-stranded circles, thereby generating a normalized cDNA library, wherein the directional cDNA library is generated by using a primer having a rare restriction enzyme recognition site for the first strand cDNA synthesis, upstream of the oligodT stretch.

Vectors that allow propagation in single-stranded circles are well-known in the art. An example of the vector is a phagemid. Another example of the vector is the λzap system.

This invention provides the above method to normalize a cDNA library wherein step (b) the cDNA clones is annealed to an appropriate primer and controlled extensions are performed with an appropriate polymerase in the presence of appropriate ratio between the dideoxynucleotide triphosphates and deoxynucleotide triphosphates.

Rare restriction enzyme recognition sites are well-known in the art. In an embodiment, a Not I site is used. In another embodiment, a Pac I site is used.

In an embodiment, the controlled extensions are performed with Klenow.

In another embodiment, the controlled extensions are performed in the presence of excess dideoxynucleotide triphosphates containing dideoxyadenosine triphosphate, dideoxycytidine triphosphate and dideoxyguanosine triphosphate over deoxynucleotide triphosphates including deoxyadenosine triphosphate, deoxycytidine triphosphate, deoxyguanosine triphosphate and deoxythymidine triphosphate.

Methods to purify partial duplexes from single-stranded circles have been well-known in the art. In an embodiment, the partial duplexes are purified by hydroxyapatite column chromatography. Other methods such as affinity-capture techniques may be similarly used. One design of the affinity-capture may include using biotinylated deoxynucleotide in the controlled extension reaction and subsequently capture of the incorporated biotinylated nucleotides by avidin conjugated on a column. There are other affinity-capture techniques which may be similarly used in accordance with this invention.

This invention also provides the above methods which further comprise introduction of the unassociated single-stranded circles into host cells. In an embodiment, the single-stranded circles are converted to double-stranded DNA before the introduction into the hosts.

This invention further provides normalized libraries which are generated by the above-described methods.

In an embodiment, the cDNA library is derived from an adult brain. In another embodiment, the cDNA library is derived from an adult hippocampus. In still another embodiment, the cDNA is derived from an infant brain. In another embodiment, the cDNA is derived from a fetal brain. In another embodiment, the cDNA is derived from a fetal liver. In another embodiment, the cDNA is derived from infant liver. In another embodiment, the cDNA is derived from an infant spleen. In still another embodiment, the cDNA is derived from an infant heart. In still another embodiment, the cDNA is derived from an infant lung. In still another embodiment, the cDNA is derived from an infant muscle. In still another embodiment, the cDNA is derived from an adult spinal cord. In a further embodiment, the cDNA is derived from a placenta. In a further embodiment, the cDNA is derived from fetal eyes.

This invention provides a human cDNA catalogue comprising at least two tagged normalized libraries generated by the above-described method.

This invention also provides a method to normalize cDNA catalogue comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to appropriate Cot; and (e) purifying the unassociated single-stranded circles, thereby generating a normalized cDNA library.

This invention also provides a normalized cDNA catalogues generated by the above-described method.

This invention further provides a method of isolating cDNA clones specific to a tissue comprising: (a) hybridizing single-stranded DNA circles from a normalized library generated by the above-described method with excess RNAs derived from other tissue; and (b) separating the hybridized DNA circles from the unhybridized DNA circles, thereby isolating cDNA clones specific to the tissue. In an embodiment, the RNAs are synthesized in vitro from at least one normalized cDNA library. In a separate embodiment, the RNAs are at least one hundred fold excess than the single-stranded DNA circles. In a still further embodiment, the normalized libraries used are tagged with different sequence. In another embodiment, the above-described method, further comprising inputting single-stranded DNA circles of normalized library from other tissue in step (a).

This invention also provides a method of isolating cDNA clones specific to a tissue comprising: (a) hybridizing approximately equal amount of single-stranded DNA circles from a tagged normalized library and single-stranded DNA circles from at least one normalized library of other tissue but with different tag with excess in vitro synthesized RNAs from the tagged normalized library of other tissue; (b) separating the hybridized DNA circles from the unhybridized DNA circles; (c) determining the tag on unhybridized DNA circles, the absence of the tag sequence of the normalized library of other tissue indicating the completeness of the hybridization in step (a), thereby isolating cDNA clones specific to the tissue.

This invention provides a method of identifying cDNA clones capable of hybridizing a genomic clone comprising: (a) hybridizing the genomic clone with the single-stranded circles of a normalized cDNA library generated by the above-described method; and (b) separating the hybridized cDNA circles from the unhybridized circles, thereby identifying cDNA clones capable of hybridizing the genomic clone.

This invention provides a method of identifying cDNA clones capable of hybridizing a genomic clone comprising: (a) immobilizing the genomic clone on a solid matrix; (b) hybridizing the genomic clone with the single-stranded circles of a normalized cDNA library generated by the above-described method; (c) separating the hybridized cDNA circles from the unhybridized circles; and (d) eluting the hybridized cDNA circles from the solid matrix, thereby identifying cDNA clones capable of hybridizing the genomic clone. In an embodiment, the unhybridized circles are separated from the hybridized circles by washing the matrix with an appropriate buffer.

This invention further provides a method of identifying cDNA clones capable of hybridizing a genomic clone comprising: (a) growing the genomic clones from a genomic library on a master plate; (b) duplicating the genomic clones on a solid matrix such that the positions of the clones on the master plate and the matrix can be correlated; (c) hybridizing the genomic clones on the solid matrix with the single-stranded circles of a normalized cDNA library generated by the above-identified; (d) washing the matrix to separate the hybridized cDNA circles from the unhybridized circles; (e) labelling the hybridized cDNA circles of step (d) with a probe such that the position of the genomic clone on the master plate could be determined; and (f) eluting the hybridized cDNA circles from the solid matrix, thereby identifying cDNA clones capable of hybridizing the genomic clone which is determined on the master plate. In an embodiment the solid matrix is a filter. In another embodiment, the probe is nucleic acid molecule capable of hybridizing to the single-strand circle and is labelled.

This invention further provides the above-described method further comprising converting the eluted hybridized DNA circles to partial duplexes. In an embodiment, the duplexes are introduced into competent host cells. In a further embodiment, the duplexes are introduced into the cell by electroporation.

The ultimate goal of this proposal is to generate a reference normalized "human cDNA catalogue", in which the majority of the 100,000 or so existing genes will be represented. It is here referred to as a catalogue because it will comprise a number of different normalized cDNA libraries from a great variety of human tissues and stages of development.

An important feature of this cDNA catalog is that each library component will have a characteristic sequence identifier (tissue-specific IDs), provided by the oligonucleotide primer utilized for first strand cDNA synthesis, the sequence of which will be unique to each library. This cDNA catalogue will be analogous to a folder with many files each of which with a different color.

The next step will be to subdivide the catalogue into a number of normalized sub-libraries according to the pattern of expression of their components. The availability of the cDNA catalogue and of each of the individual normalized libraries will provide a unique opportunity for the performance of a number of subtractive hybridizations for isolation of tissue-specific sublibraries. Most importantly, however, it will allow unambiguous assessment of tissue-specificity by single pass sequencing of randomly picked clones from a subtracted sub-library. This will be possible because in a tissue-specific sublibrary all clones should have the same characteristic sequence ID.

A method to normalize directionally cloned cDNA libraries constructed in phagemid vectors (Soares and Efstratiadis, manuscript in preparation) which presents certain important advantages over other existing protocols (Ko, 1990; Patanjali et al., 1991) has been developed. This method has been utilized to normalized an infant brain cDNA library which has been extensively characterized. This established protocol is used to normalize all libraries that will be constructed.

In summary, this invention has the following specific aims:

a) to construct a number of directionally cloned cDNA libraries from a variety of human tissues and stages of development, each one of which with its unique sequence identifier;

b) to pool all these libraries together and re-normalize them to generate the "human cDNA catalogue";

c) to assess the efficiency of normalization by colony hybridization with an already available panel of cDNA probes representing the three frequency classes of mRNAs;

c) to optimize procedures for performance of subtractive hybridization of normalized libraries;

e) to generate a number of tissue-specific normalized sub-libraries by a series of subtractive hybridizations involving each of the individual normalized libraries, or combinations of them, and the cDNA catalogue;

f) to assess the efficacy of each subtractive hybridization by verification that any clone randomly picked from a tissue-specific sub-library has the correct sequence identifier at its 3' end. This will be done by single pass sequencing of a random sampling of clones from each subtracted library; and g) to assess the complexity of each tissue-specific sub-library. In a normalized library the frequency of all clones is within a narrow range. Therefore, by determining the frequency of a few individual clones one can estimate the total number of clones existing in the library.

A different method for normalization of directionally cloned cDNA libraries constructed in phagemid vectors which is based on the same kinetic principle has been developed. Briefly, the method involves annealing of the library in the form of single-stranded circles with a Not I-oligo(dT)18 primer and controlled extensions (160±20 nt) with Klenow in the presence of dNTPs and ddNTPs. After purification of the partial duplexes over HAP, and melting and re-annealing to a moderate Cot, unhybridized (normalized) single-stranded circles are purified by HAP and electroporated into bacteria, generating a normalized library. The advantages of this invention can be outlined as follows:

a) because it does not require any cycle of cDNA amplification by the polymerase chain reaction, and therefore no length constraints are imposed, the cDNA clones in the normalized library constructed by this invention have large size inserts (average of 1.7 kb). Because the library is directionally cloned, the 3' end of a clone contains the 3' terminal exon of the mRNA, with a short polyadenylate track and a recognizable polyadenylation signal sequence at the appropriate position, whereas the 5' end of a clone almost always lies within coding sequence;

b) there is no cloning step involved in this invention, after completion of the reassociation reaction; and c) although the normalized library constructed according to this invention consists of clones that contain both coding and 3' non-coding exons, only 3' non-coding sequences participate in the reassociation reaction, thus addressing the problem raised by Ko (1990) regarding the potential cross hybridization between coding exons from gene family members that are represented at different frequencies in the original cDNA population, without however, having to sacrifice the quality of the normalized library by leaving behind all relevant coding sequence information.

In the normalized cDNA catalogue, the origin (tissue source) of each clone will be readily known by single pass sequencing from the 3' end. This will be possible because each library component of this cDNA catalogue will have a distinctive sequence fingerprint. For each library a slightly different primer will be utilized for first strand cDNA synthesis. All primers will have in common the recognition sequence for a rare restriction site (Pac I), for directional cloning, and an oligo-dT track to prime cDNA synthesis off the polyadenylate tail of the mRNAs. However, the few nucleotides that lie between the 5' Pac I recognition sequence and the 3' oligo-dT track will be different for each primer, thus allowing immediate origin identification for any clone of the catalogue by straightforward single pass 3' end sequencing.

Subtractive hybridization

Subtractive hybridization of nucleic acids has proven to be a powerful method to isolate differentially expressed genes (Klar et al., 1992; Dear et al., 1988; Lee et al., 1991; Duguid et al., 1988; Yancopoulcs et al., 1990; Owens et al., 1991; Travis et al., 1987; Loros et al., 1989; Sykes & Weiser, 1992; Dear et al., 1991; Hara et al., 1991; Kho & Zarbl, 1991; Sive & St. John, 1988).

Subtractive hybridization experiments typically involved hybridizing first-strand cDNA (tracer) with an excess of poly (A⁻ RNA (driver). The remaining single-stranded cDNAs were separated from the DNA-RNA hybrids by HAP chromatography and either cloned (Travis & Sutcliffe, 1988) or used as a probe in a differential screening procedure (Miller et al., 1987).

Simpler and more efficient methods for subtractive hybridization have now been described. Rubenstein et al. (1991) described a method according to which photobiotinylated single-stranded phagemids from a directionally cloned cDNA library were used as drivers in a hybridization with tracer amounts of complementary single-stranded phagemids. After binding to streptavidin and extracting with phenol:chloroform, the unhybridized single-stranded circles (subtracted library) were recovered from the aqueous phase, converted to partially duplex circular molecules (for improvement of electroporation efficiencies) and electroporated into bacteria. Swaroop et al. (1991) successfully isolated a number of retina-specific clones by a very simple procedure involving hybridization of in vitro synthesized biotinylated RNA (run-off transcription of a directionally cloned cDNA library in the presence of Bio-11-UTP) with single-stranded phagemids from a directionally cloned cDNA library. DNA-RNA hybrids were captured by affinity to vectrex-avidin (Vector Laboratories) and the single-stranded circles (subtracted library) were eluted, precipitated with glycogen and directly electroporated into bacteria.

The method used is very similar to that described by Swaroop et al. (1991). The novelty of this approach, however, is that normalized libraries, both as drivers and tracers, in all subtractive hybridization experiments will be utilized, a feature that should improve the overall efficiencies of subtraction.

This invention will be better understood from the Experimental Details which follow. However, one skilled in the art will readily appreciate that the specific methods and results discussed are merely illustrative of the invention as described more fully in the claims which follow thereafter.

Experimental Details

Construction of directionally cloned cDNA libraries in phagemid vectors

Existing protocols to construct directionally cloned cDNA libraries in phagemid vectors (Soares, 1993) have been optimized in an effort to minimize some of the most widely acknowledged problems with cDNA libraries (Adam et al., 1991), i.e., a) high frequency of clones with small size inserts; b) large number of clones with long polyadenylate tails; c) detectable (but undetermined) frequency of chimeric clones; and d) undesirable number of recombinant clones.

The general scheme for construction of directionally cloned cDNA libraries can be outlined as follows: a) a Not I-(dT)18 oligonucleotide [or Pac I-(dT)18] is utilized as primer for first strand cDNA synthesis with RNAse H⁻ Reverse Transcriptase from Moloney Murine Leukemia Virus (Gibco®-BRL); b) "one tube" first and second strand cDNA syntheses are performed essentially as described (D'Alessio et al., 1987); c) double-stranded cDNAs are polished with T4 DNA Polymerase, size selected on a Bio-Gel A-50m column as described (Huynh et al., 1985) and ligated to a large excess of adaptor molecules (for the brain library described below which was constructed in the Lafmid BA vector applicants used Hind III adaptors, but for all libraries that applicants are planning to construct in the pT7T3-Pac I vector, applicants will utilize Eco RI adaptors instead); d) cDNAs are treated with T4 Polynucleotide Kinase to phosphorylate the adaptor ends (one of the two oligonucleotides of the adaptor molecule has a 5'OH to prevent concatemerization of adaptors), digested with Not I (or Pac I, depending on the primer utilized for 1st strand cDNA synthesis), size selected again over a Bio-Gel A-50m column and ligated directionally into the Not I and Hind III (Lafmid BA vector) or Pac I and Eco RI (pT7T3-Pac vector) sites of a phagemid vector; e) the ligation mixture is electroporated into bacteria and propagated under ampicillin selection; f) to eliminate complete from the library all clones that contain inserts shorter than 500 bp, the non-recombinants, and most existing chimeric clones, a plasmid preparation of the library is linearized with Not I (or Pac I), electrophoresed on an agarose gel and the linear recombinant molecules containing cDNAs larger than 500 bp are purified off the gel with β-agarose and recircularized in a large volume ligation reaction; and g) the ligation mixture is electroporated into bacteria and propagated under ampicillin selection to generate a cDNA library with an average size insert of 1.7 kb, no inserts shorter than 500 bp and a very low background of non-recombinant clones.

The following is a brief discussion of the modifications that were introduced to address each of the specific problems mentioned above.

Clones with small size inserts

This problem was solved by strictly size selecting the cDNAs over a 32 cm long −0.2 cm wide BioGel-A50m column as described (Huynh et al., 1985). Although time consuming, this column is very reliable and reproducible. There are two rounds of size selection; one right after second strand synthesis (before adaptor ligation) and a second after adaptor ligation, just prior to setting up the ligation to the cloning vector. In addition, applicants have introduced a gel purification step after cloning and propagation in bacteria; supercoiled plasmid DNA from the library is linearized by Not I (or Pac I, depending on the primer utilized for first strand cDNA synthesis) digestion, and electrophoresed on a 1% agarose gel; and the DNA smear corresponding to cDNAs with insert sizes larger than 500 bp is cut off the gel, casted into a low melting point agarose gel, and electrophoresed backwards to sharpen the DNA smear. Library DNA is then purified by digestion of the gel slice with β-agarose. Following a ligation reaction performed under conditions that promote recircularization only, the DNA is electroporated into bacteria (DH10B, BRL®) and propagated under ampicillin selection. The exact reaction conditions to promote recircularization rather than inter-molecular ligations can be determined by the formula $3.3/\sqrt{kb}\,\mu g/ml$ as discussed by Smith et al. (1987).

The end product is a library with an average size insert of 1.7 kb (based on restriction digestion analysis of 900 clones (Adams et al., submitted), and no inserts shorter than 400 bp. Furthermore, non-recombinants (vector only) are practically undetectable [only two out of 1,500 randomly picked clones (Adams et al., submitted); or 1 out of 493 (Khan et al., 1992).

Long polyadenylate tails

This problem could be practically eliminated by increasing the amount of the Not I-(dT)-oligonucleotide utilized to prime first strand cDNA synthesis. The rationale behind this idea was that if the poly(A) tails of the mRNAs were completely saturated with primers, only the most proximal primer could be extended to reverse transcribe the mRNA [reverse transcriptase cannot strand displace efficiently (Kornberg & Baker, 1992)]. Extension of any other primer would be limited to its distance to the next downstream primer, thus generating very small fragments that could be easily eliminated by an efficient size selection procedure.

The efficiency of this modification to shorten the length of the poly(A) track present at the 3' end of all clones has been firmly documented by sequencing analysis of over 2,000 randomly picked clones from an infant brain library (Khan et al., 1991; Adams et al., submitted).

Chimeric cDNA clones

Chimeric clones often result from blunt end ligation of cDNA molecules during the reaction in which adaptors are ligated to the cDNAs. To prevent formation of these cloning artifacts, adaptor molecules must be present in vast excess over cDNAs in this ligation reaction. Such conditions can be easily satisfied only if the cDNAs are efficiently size selected prior to ligation. This is so because a large amount of very small fragments of double-stranded tail are generated during cDNA synthesis. In terms of pmoles of ends these shore cDNAs constitute a very significant fraction of the cDNA molecules and they can take up most of the adaptor molecules. Therefore, it is important that the cDNAs are efficiently size selected after second strand synthesis before ligation to the adaptors. As mentioned above, chromatography over a Bio-Gel A-50m column is a very reliable method for size selection of cDNAs.

Another step where chimeric clones can be generated is during ligation of the cDNAs to the cloning vector. This is less likely to occur, however, because the cDNA have two different ends and three cDNA molecules must be joined together before they can be ligated to a vector molecule. Nonetheless, in order to minimize the probability of formation of chimeric clones during this ligation reaction, vector should be present in excess over cDNAs. Since dephosphorylation usually reduces cloning efficiencies, the approach of not dephosphorylating the vector and using it in only a slight excess is favored; a twofold excess over cDNAs seems to be a good compromise. Under these conditions, chimeric clones are unlikely to be formed and the background of non-recombinant clones still remains low.

An important feature of these directionally cloned cDNA libraries is that a major fraction of existing chimeric clones can be easily detected. A bona fide cDNA clone from this library should be linearized with Not I (or Pac I, depending on the primer utilized for first strand cDNA synthesis). Release of a fragment after digestion is indicative of chimerism. It should be acknowledged, however, that even if digestion indicates the presence of a single Not I (or Pac I) site, the possibility remains that the clone is chimeric and one of the sites was destroyed upon cloning.

It should be emphasized that a significant percent of chimeric clones are eliminated at the final size selection step in which the library (as plasmid DNA), is linearized with Not I (or Pac I) and the recombinant molecules containing cDNA inserts larger than 500 bp are gel purified, recircularized and electroporated into bacteria.

It is to avoid such non-specific priming events that applicants are planning to replace the Not I-(dT)18 oligonucleotide originally utilized to prime first strand cDNA synthesis in applicants' protocol, with a (GC-less) Pac I-(dT)18 primer.

Modifications

The plan is to modify the protocol to replace Not I by Pac I. In this regard, a Pac I-(dT)18 oligonucleotide has been synthesized to be utilized as primer for first strand cDNA synthesis and a library is currently under construction. Control digestions have been performed to show that the recognition sequence for the enzyme Pac I occurs very rarely on cDNAs. In positive control digestions, Pac I cut a supercoiled plasmid containing a single Pac I site with no difficulty; prolonged incubations of the enzyme with a different supercoiled plasmid that did not have a Pac I site, did not result in detectable conversion of supercoiled to relaxed circles. Altogether, these results indicated that Pac I (NEB) is a very good enzyme.

Because the Lafmid BA vector, which was utilized for construction of the infant brain cDNA library described below, does not have the promoters for in vitro synthesis of RNA, applicants decided to switch to another cloning vector (pT7T3, Pharmacia®). There was no reason to modify the Lafmid BA vector to include RNA promoters since other phagemids are already available that have all features that was needed. Accordingly, the polylinker of the pT7T3 phagemid vector (Pharmacia®) was modified to include a Pac I site. This modified vector was named pT7T3-Pac by applicants. This vector has all the features that was needed to normalize and subtract libraries, i.e., it has an f1 origin for production of single-stranded circles upon super-infection with a helper phage and it contains both the T3 and T7 promoters for in vitro synthesis of RNA.

The sequence of the polylinker of the pT7T3-Pac vector is:

```
           Sfi  I     Eco  RI       SnaBI          BamHI        Pac  I
5'GGCCCTCGAGGCCAAGAATTCCCGACTACGTAGTCGGGGATCCGTCTTAATTA

Not  I    HindIII
AGCGGCCGCAAGCTT 3'   (SEQ ID NO. 3).
```

Non-specific priming events

Some precautions are necessary to avoid non-specific priming at GC-rich regions of the mRNAs when using large amounts of the Not I-(dT)18 primer for first strand cDNA synthesis. Most importantly, the reaction mixture should be pre-incubated at 37° C. before the addition of reverse transcriptase. It was observed that if the enzyme is added to the reaction mixture while it is at room temperature, an appreciable number of clones without tail can be obtained. For example, clones for the mitochondrial 16S rRNA which resulted from priming events at two sites of the RNA sequence that differ from the recognition sequence of the Not I restriction enzyme by a single nucleotide have been obtained. Presumably, if a GC-rich cluster is flanked by a few (A)s located upstream on the RNA, the Not I sequence (GCGGCCGC, SEQ ID No. 1) of the primer can anneal to it while most of the oligo-dT tail loops out. The end product of such non-specific priming events can be a clone without a tail or a clone with a very short tail (shorter than the primer) These clones are easily detected because a bona fide polyadenylation signal sequence (AAUAAA, SEQ ID No. 2) cannot be identified at the appropriate position.

The plan is to clone cDNAs directionally into the Eco RI and Pac I sites of this phagemid vector. Accordingly, Pac I will be utilized to linearize the library for the gel purification step. Since (mRNA-like) and antisense RNA can be transcribed in vitro off the existing T7 and T3 promoters, respectively, which immediately flank the polylinker. Single-stranded circles will have the mRNA-like strand. Therefore, run-off transcripts from the T3 promoter will be complementary to the library in the form of single-stranded circles.

Preparation of high efficiency electrocompetent bacteria and propagation of cDNA libraries Protocols to make electrocompetent bacteria which yield cells with electroporation efficiencies of $6 \times 10^{10}$ cfu/$\mu$g CsCl-banded supercoiled plasmid DNA have been optimized. A side by side comparison of the electroporation efficiencies of the electrocompetent bacteria used with that of the commercially available Electromax (BRL®) have been done. The BRL cells had the advertised efficiency of $10^{10}$ cfu/$\mu$g whereas applicants' had a 6 fold higher efficiency. Very high efficiency electrocompetent bacteria was needed for some of the work done in the laboratory. That was the reason why some time was invested on the improvement of this protocol. According to the existing protocols (Dower et al., 1988; Zabarovsky & Winbert) the bacterial culture is grown to an $A_{600}$=0.5 to 1, when the cells are than harvested and sequentially washed with large volumes of 10% or 20% glycerol. The highest electroporation efficiencies were achieved when the cultures were harvested at a lower OD ($A_{600}$=0.2): the % live cells at the end of all manipulations was higher, and electroporation efficiencies of $6 \times 10^{10}$ cfu/μg were reproducibly obtained for DH10B bacteria. Applicants have two types of electrocompetent bacteria: DH10B and dH5αF'.

As a rule of thumb, the only time when a cDNA library is propagated into male (F') bacteria (dH5αF') is for production of single-stranded circles. For all other purposes (especially for amplification) female bacteria (DH10B) was used because they cannot get infected by filamentous phage. Despite all precautions that are taken to avoid "undesirable contaminants", helper phage can accidentally get introduced into a culture. It was observed that if a library is super-infected with helper phage for a prolonged time, differential growth of clones becomes apparent. That is why for single-stranded production, the culture was only allowed to be in the presence of helper phage for a limited amount of time. Thus, to avoid taking any chances, DH10B cells were used for most applications.

Propagation of cDNA libraries in the form of single-stranded circles

1–10 ng supercoiled plasmid DNA representing the entire library is electroporated into dH5αF', grown at 37° C. for one hour and then propagated under ampicillin selection to mid-log phase. The culture is then diluted 100 fold with fresh medium and grown in the presence of 0.2% glucose under ampicillin selection to $A_{600}$=0.2. At this time, the culture is superinfected with a 10–20 fold excess of helper phage (R408 or M13KO7) and grown for only four hours. The culture must be harvested at that time. Prolonged growth in the presence of helper phage is detrimental and must be avoided. The yield of single-stranded material will not be any better while differential growth will start to become apparent. To be safe, applicants routinely verified that no helper phage got accidentally introduced into the starting culture as follows: a sample of the culture is span down, and a drop of the supernatant is spotted onto a lawn of infectable bacteria to show that it can yield no plaques. Single-stranded DNA is prepared according to standard protocols which involve precipitation of packaged single-stranded circles with polyethyleneglycol and phenol/Sevag extractions.

Applicants have performed control colony hybridization experiments to show that the frequency of several of the abundant clones (α-tubulin, elongation factor 1α, β-tubulin and myelin basic protein) was absolutely identical in both the starting double-stranded library and in the library in the form of single-stranded circles. Thus, if prepared under the conditions described above, the library in the form of single-stranded circles is perfectly representative of the starting library.

cDNA library normalization

Applicants have developed (Soares & Efstratiadis, manuscript in preparation; see FIG. 1) a method for normalization of directionally cloned cDNA libraries constructed in phagemid vectors and successfully utilized it to normalize an infant brain cDNA library (see Table 1).

Applicants' method differs from other existing procedure (Ko, 1990; Patanjali et al., 1991) in several aspects. First, instead of utilizing PCR-amplified cDNA fragments as the starting material for the kinetic approach, library DNA was utilized in the form of partially duplex circles. (It should be emphasized that the double-stranded region of these circles correspond primarily to the 3' non-coding sequences. These partially duplex molecules are then melted and reassociated, and the remaining (non-reassociated, normalized) single-stranded circles are HAP-purified and electroporated into bacteria. Thus, the reassociation reaction involves primarily 3' untranslated sequences. It should also be noted that in applicants' method, the single-stranded (normalized) material at the end of the melting/reassociation reaction consists of already cloned cDNAs, as opposed to relatively short single-stranded cDNA molecules that need to be amplified by PCR and cloned in order to generate a normalized library (Ko, 1990; Patanjali et al., 1991).

The cDNA clones in the normalized infant brain cDNA library generated by this protocol contain large size inserts (average of 1.7 kb). Non-recombinant (vector only) molecules have not yet been detected in the normalized library (they were already almost undetectable in the library before normalization and they should have been left behind in the procedure because they could not have gotten primed in the first place). Digestion of over 200 clones with Not I failed to detect a single-chimeric clone (as discussed, non-chimeric clones should only be linearized with Not I; release of a Not I fragment would be indicative of chimerism).

For the construction of the infant brain (non-normalized) library, a Not I- (dT) 18 oligonucleotide [5'AACTGGAAGAATTCGCGGCCGCAGGAA(T)18, SEQ ID No. 4] was utilized as primer for first strand cDNA synthesis. After ligation to Hind III adaptors, the cDNAs were digested with Not I (after appropriate size selections) and directionally cloned into the Hind III and Not I sites of a plasmid vector (lafmid BA) derived from pEMBL. The polylinker of the lafmid BA vector contains the following restriction sites: 5' Hind III; Bam HI; Not I; and Eco RI 3'.

Single-stranded library DNA represents the message (mRNA-like) strand and therefore all single-stranded circles contain a short polyadenylate tail at their 3' end (except for the non-specific priming events discussed before, where priming took place at GC-rich regions rather than at the polyadenylate tail of the mRNAs).

Following is a brief description of the steps involved in the normalization of this infant brain cDNA library (See FIG. 1 for a schematic representation).

a Single-stranded library DNA was purified from any residual double-stranded plasmid contaminant by HAP column chromatography under standard aqueous conditions (Britten et al., 1974), in a jacketed column at 60° C. It should be noted that single-stranded circles are very sensitive to high temperatures (electroporation efficiencies of single-stranded circles drop very dramatically upon boiling, for example). However, a quick purification through a 60° C.-HAP column does not damage single-stranded circles in applicants' hands. HAP-purified single-stranded DNA was then purified from any residual amount of tRNA and from most of the helper phage DNA by agarose gel electrophoresis. The gel slice containing the single-stranded library DNA smear was casted into low melting point agarose. The current was reversed and the low melt agarose gel was run for a short time just to sharpen the smear. DNA was isolated after digestion with β-agarose (NEB). This gel purification step proved to be necessary to avoid undesirable internal priming events promoted by small RNA oligonucleotides (breakdown products from RNAse A digestion of tRNAs). The single-stranded DNA was never exposed to UV light (a small fraction of it was run on a separate lane, which was exposed to UV and served as a reference; this DNA was not used).

b) 0.6 pmoles of a ½ Not I-(dT)15 oligonucleotide [5'GGCCGCAGGAA(T)15, SEQ ID Nos. 5 and 6] were added to 0.3 pmoles of single-stranded circles (library DNA) in a 10 µl reaction containing 30 mM Tris pH7.5–50 mM NaCl–15 mM MgCl$_2$–1 mM DTT–0.1 mM each deoxynucleotide (dA, dC, dT, and dG)–2.5 mM each dideoxynucleotide (ddA, ddC and ddG; but no ddT) and a trace of α$^{32}$PdCTP. The mixture was first incubated for five minutes at 60° C., and then for fifteen minutes at 50° C. (annealing temperature). The temperature was lowered down to 37° C., 5 units of Klenow enzyme were added and the reaction remained at 37° for thirty minutes. Fifteen such reactions were carried out in parallel.

The size distribution of the synthesized strand was rather narrow (160t±20 nt; see FIG. 2, lane 4). Klenow was the only polymerase among the several that were tried that yielded such a sharp size distribution. Since 3' non-coding exons are usually larger than 300 nt (average of 600 nt), the vast majority of the synthesized material should correspond to 3' untranslated sequences.

In the next step these partially duplex circular molecules were purified from any remaining (unprimed, unextended) single-stranded circles by HAP chromatography (applicants have actually also tried incorporating biotinylated nucleotides during the extension reaction to allow capturing of the partial duplex circles by affinity to streptavidin-coated solid supports; the results were not satisfactory in applicants' hands especially because the procedure resulted in a dramatic impairment of electroporation efficiencies).

c) All 15 reactions were pooled together and stopped with EDTA (20 mM f.c.). The sample was extracted with phenol+Sevag, and phosphate buffer (PB) was added to a final concentration of 0.12M. 2 mls of 60° C. prewarmed 0.12M PB-10 mM EDTA-1% SDS containing 50 µg denatured sonicated salmon sperm DNA were added to the sample and the mixture was passed through a HAP column at 60° C. The column (0.4 g HAP, about 1 ml bed column) had been pre-equilibrated with 0.12M PB-10 mM EDTA-1% SDS. After a wash with 6 mls of 0.12M PB-10 mM EDTA-1% SDS, the partial duplex circles (HAP-bound) were eluted off the column with 6 mls of 0.4M PB-10 mM EDTA-1% SDS. 14 mls H$_2$O containing 50 µg denatured sonicated salmon sperm DNA were added to this eluate to lower the PB concentration down to 0.12M, the column was re-equilibrated with 0.12M PB-10 mM EDTA-1% SDS and the sample was passed through the column again. This second passage through HAP was necessary to eliminate the background of single-stranded circles that bind non-specifically to HAP; every time single-stranded DNA is passed through HAP, about 0.1% of it binds non-specifically. However, by passing it through twice, this background becomes negligible (0.1×0.1=0.01%). The column was washed with 6 mls 0.12M PB-10 mM EDTA-1% SDS and the partially duplex circles (HAP-bound) were eluted with 6 mls 0.4M PB-10 mM EDTA-1% SDS.

d) The eluate was desalted over a Nensorb column (DuPont). DNA was eluted off the Nensorb column with 1 ml 20% n-propanol in H$_2$O, vacuum-dried for 30 minutes, (at this point, an aliquot of the material was applied on a 6% sequencing gel for determination of the sizes of the extended material; see FIG. 2) and ethanol precipitated.

e) The DNA pellet was resuspended in 2.5 µl formamide and heated for 3 minutes at 80° C. under a drop of mineral oil. 1 µl 5 µg/µl oligo-(dT)25–30, 0.5 µl 1 µg/µl½Not-(dT)15 oligonucleotide, 0.5 µl 5M NaCl, and 0.5 µl 0.1M Tris-0.1M EDTA (total 5 µl) were added and the mixture was incubated at 42° C. [oligo-(dT)25–30 and ½Not-(dT)15 oligonucleotides were present to block the polyadenylate tails]. Small aliquots were taken at various times. The best normalization results (see Table 1) were obtain after 13 hours of incubation.

f) In this next step, the remaining (normalized) single-stranded circles were separated from the (reassociated) partially double-stranded circular molecules by HAP chromatography.

To 0.5 µl of the hybridization mixture, 5 µg were added of denatured sonicated salmon sperm DNA+2 mls of 60° C. prewarmed 0.12M PB-10 mM EDTA-1% SDS and the sample was passed through 0.4 g HAP. The column was washed with 6 mls 0.12M PB-10 mM EDTA-1% SDS and the HAP-flow-through (containing the normalized single-stranded circles) was passed through a second (fresh) HAP column just to minimize the chance that any residual amount of partially double-stranded molecules escaped from binding through some undetected small channel in the column; by passing it through a fresh column this potential problem was eliminated. The column was washed with 6 mls 0.12M PB-10 mM EDTA-1% SDS and the flow-through material (normalized single-stranded circles) was desalted through a Nensorb column as described above. HAP-bound DNA from the first column was also purified.

g) At this point, one can either directly electroporate the single-stranded circles (HAP-flow-through) into competent DH10B bacteria, or one may convert them into partially double-stranded circles (by primed extension) in order to improve their electroporation efficiencies by 50–100 fold. Such extensions can be primed with random hexamers, the M13 Universal primer, or an oligonucleotide complementary to a region of the ampicillin resistance gene. Applicants have successfully utilized all three of them.

After 1 hour at 37° C., an aliquot of the culture (10 µl out of 100 mls) was plated on an LB agar plate containing ampicillin for determination of total number of transformants, ampicillin was added to the culture to a final concentration of 75 µg/ml, and the bacteria were propagated until the culture reached mid-log phase. Supercoiled plasmid DNA (normalized library) was extracted by alkaline lysis and purified over a Qiagen mid-size column. 2.5 million transformants were obtained from the 0.5 µl of hybridization mixture that were processed.

Characterization of the normalized infant brain library by colony hybridization with a panel of probes Applicants have performed colony hybridization experiments to assess the frequency of a number of cDNA probes in the infant brain library both before and after normalization (see Table 1). The results indicated that the normalization was successful. The frequency fold variation observed amount 13 cDNA probes that were tested in the starting library was of 575 (cDNA probe elongation factor 1α=4.6%; cDNA probe Cot250#1-unknown=0.008%) In contrast, the frequency variation of 23 cDNA probes that were tested in the normalized library was only of 30 fold (cDNA probe γ-actin=0.1%; cDNA probe MAP=0.033%). Eight of these cDNA probes corresponded to cDNA clones that were randomly picked up from the normalized library (they were all given the prefix "normalized" in Table 1, column 1): their frequencies were within a 17 fold range (the most frequent was at 0.05% and the least frequent at 0.003%).

It should be mentioned that the number of positive hybridizers observed in both libraries (before and after normalization) with a human Cot1 DNA probe was within a twofold range. Similar results were also obtained by Ko (1990) and Patanjali et al. (1991). When divergent members of repetitive DNA families reassociate, they form imperfect hybrids that are likely not to bind to hydroxyapatite under standard conditions. Under applicants' conditions only double-stranded DNA 100 bp or longer (without any mismatched bases) can bind to HAP. This is a very desirable feature of the HAP which assures us that even those rare cDNA clones that happen to contain a repetitive DNA element within their 3' noncoding sequences will be represented in the normalized library.

Overall design and methods

The plan is to construct cDNA libraries from a number of different tissues, to normalize each one of them separately, to pool all the individual normalized libraries and re-normalize them together to generate a human cDNA catalogue. Each individual library will have a distinctive sequence identifier, so that information on the origin of any clone of the cDNA catalogue can be immediately retrieved.

These resources will provide a unique opportunity for the performance of a series of subtractive hybridizations involving normalized libraries. Furthermore, these sequence identifiers will allow immediate verification of tissue-specificity of clones from a subtracted library by straightforward single pass sequencing.

Construction and normalization of cDNA libraries

Human tissues are obtained for construction of the following cDNA libraries:

Infant brain library

Infant brain (total brain from a 3-month old human infant who died in consequence of spinal muscular atrophy) High quality mRNA is available. This mRNA was already utilized for construction of a cDNA library in the lafmid BA vector. However, because the lafmid BA vector does not allow for in vitro synthesis of RNA, a feature that is required in applicants' strategy for library subtraction, applicants will utilize this mRNA again to construct a cDNA library in the pT7T3-Pac vector.

Adult brain library

Adult brain (a collection of tissue samples representing all regions of the brain with the exception of hippocampus). Power was prepared from multiple areas of the brain and pooled. These areas included frontal, parietal, temporal and occipital cortex from the left and right hemispheres, subcortical white matter, basal ganglia, thalamus, cerebellum, midbrain, pons and medulla. High quality RNA is already available.

Adult hippocampus library

Adult hippocampus (obtained from the same brain of that utilized for construction of library #1). Both hippocampi were utilized. High quality RNA is already available.

Other libraries from different human tissue such as fetal brain, fetal liver, infant liver female, infant spleen, infant heart, infant lung, infant muscle, adult spinal cord, placenta, and fetal eyes.

Additional libraries may be constructed depending on availability of good tissue sources. As mentioned above, each of these cDNA libraries will have a characteristic sequence identifier, which will be provided by the oligonucleotide utilized to primer first strand cDNA synthesis.

The following is a list of these primer sequences:

5' TTT TTT TTAATTAA TTTT TT TTT TTT TTT TTT 3' (SEQ ID No. 8); 5' TTT TTT TTAATTAA GAGT TT TTT TTT TTT TTT TTT 3' (SEQ ID No. 9); 5' TTT TTT TTAATTAA TAGG TT TTT TTT TTT TTT TTT 3' (SEQ ID No. 10); 5' TTT TTT TTAATTAA CGTC TT TTT TTT TTT TTT TTT 3' (SEQ ID No. 11); 5' TTT TTT TTAATTAA TGCT TT TTT TTT TTT TTT TTT 3' (SEQ ID No. 12); 5' TTT TTT TTAATTAA AGCA TT TTT TTT TTT TTT TTT 3' (SEQ ID No. 13); 5' TTT TTT TTAATTAA GCTA TT TTT TTT TTT TTT TTT 3' (SEQ ID No. 14); 5' TTT TTT TTAATTAA CAAT TT TTT TTT TTT TTT TTT 3' (SEQ ID No. 15); 5' TTT TTT TTAATTAA CTGA TT TTT TTT TTT TTT TTT 3' (SEQ ID NO. 16); 5' TTT TTT TTAATTAA AAAG TT TTT TTT TTT TTT TTT 3' (SEQ ID No. 17); 5' TTT TTT TTAATTAA ACTG TT TTT TTT TTT TTT TTT 3' (SEQ ID No. 18); 5' TTT TTT TTAATTAA ATCC TT TTT TTT TTT TTT TTT 3' (SEQ ID No. 19); 5' TTT TTT TTAATTAA CCAC TT TTT TTT TTT TTT TTT 3' (SEQ ID No. 20); and 5' TTT TTT TTAATTAA GGAA TT TTT TTT TTT TTT TTT 3' (SEQ ID No. 21)

All primers will have the recognition sequence for the Pac I restriction endonuclease (TTAATTAA, SEQ ID No. 7), for directional cloning of cDNAs. The library sequence identifiers are underlined.

It is not the intention of this invention to be limited by the above embodiments.

This approach is to introduce a sequence ID which can be of any number of nucleotides and can be of any sequence. Such IDs should be present in the primer which is sued to prime the first strand cDNA between the recognition sequence for a rare cutter and an oligodT stretch. The use of Pac I as a rare cutter sequence is simply an example. An ordinary skilled artisan will be able to use this approach with other rare cutter sequence after reading this specification.

All cDNA libraries may be constructed in the pT7T3-Pac I vector. Applicants will follow the above-described protocols to construct all libraries. The only modification will be that instead of utilizing the Not I-d(T) 18 oligonucleotide to prime first strand cDNA synthesis, applicants will use the Pac I-d(T)18 oligonucleotides described above. Accordingly, the double-stranded cDNAs (after ligation to Eco RI adapters and required purifications) will be digested with Pac I (as opposed to Not I) and directionally cloned into the Pac I and Eco RI sites of the pT7T3-PacI vector. As discussed above, applicants decided to switch from Not I (GCGGCCTC, SEQ ID No. 22) to Pac I (TTAATTAA, SEQ ID No. 23), to avoid some of the non-specific priming events that can occur at GC-rich regions of mRNAs when priming first strand cDNA synthesis with the Not I-(dT)18 oligonucleotide.

Each individual cDNA library will be propagated in the form of single-stranded circles (mRNA-like strand), and normalized separately, according to the established protocol described in the Preliminary Results section. The only necessary modification regards the oligonucleotide to be utilized in the controlled primed extension reactions of the normalization procedure (see FIG. 1). Applicants will synthesize a degenerate oligonucleotide [5'CCGCTTAATTAANNNN(dT15, SEQ ID No. 24) named ½Not-Pac-(dT)15'] specific for this purpose. Its 5' most nucleotides (CCGC, SEQ ID No. 25) will be complementary to the sequence of the vector that immediately flanks the Pac I cloning site, thus serving as an anchor point which will allow applicants to raise the stringency of the annealing reaction and therefore minimize non-specific priming events. The same rationale was followed for the choice of the ½Not-(dT) primer utilized in the extensions for the successful normalization of the infant brain library.

If for any reason this primer will not work satisfactorily, applicants have the choice of priming each single-stranded individual library with its respective (and specific) Pac-(dT) 17–18 oligonucleotide.

Assessment of normalization will be done for each individual library by colony hybridization screenings with a panel of cDNA probes representing the three frequency classes of mRNAs, similarly to what was done to characterize the normalized infant brain library (see Table 1).

TABLE 1

FREQUENCIES OF cDNA CLONES IN AN INFANT BRAIN LIBRARY BEFORE AND AFTER NORMALIZATION

| cDNA clone | Frequencies | |
|---|---|---|
| | Before Normalization | After Normalization |
| Elongation factor 1α | 4.6% | 0.04% |
| α Tubulin | 3.7–4.4% | 0.045% |
| Myelin basic protein | 1% | 0.09% |
| γ-actin | 0.35% | 0.1% |
| Aldolase | 0.6% | 0.03% |
| Hsp 89 | 0.4% | 0.05% |
| Secretogranin | 0.07–0.1% | 0.01% |
| Cot109 + 103-bio20-unknown | 0.08% | 0.005% |
| CH13-cDNA#20-endogenous retrov | 0.02% | 0.02% |
| Cot109 + 103#4-unknown | 0.014% | 0.005% |
| Histone H2b.1 | 0.014% | 0.015% |
| CH13-cDNA#8-unknown | 0.01% | 0.035% |
| MAP | Not determined | 0.0033% |
| Cot250#1-unknown | 0.008% | 0.015% |
| YAC4 cDNA#1-unknown | Not determined | 0.006% |
| Normalized-cDNA #103-unknown | Not determined | 0.013% |
| Normalized-cDNA #120-unknown | Not determined | 0.003% |
| Normalized-cDNA #122-unknown | Not determined | 0.007% |
| Normalized-cDNA #138-unknown | Not determined | 0.02% |
| Normalized-cDNA #141-unknown | Not determined | 0.05% |
| Normalized-cDNA #142-unknown | Not determined | 0.01% |
| Normalized-cDNA #143-unknown | Not determined | 0.04% |
| Normalized-cDNA #114-unknown | Not determined | 0.007% |

Construction of the human cDNA catalogue

1–10 ng of supercoiled plasmid DNA from each of the 14 normalized libraries will be separately electroporated into dH5αF' and each culture (200 mls) will be grown under ampicillin selection to early-log phase ($A_{600}$=0.1–6×10$^7$ colonies per ml culture). 10$^7$ cells from each of the 14 cultures will then be pooled together (14×10$^7$ or 1.4×10$^8$ total cells), and diluted 50-fold with fresh broth containing 0.2% glucose and 75 μg/ml ampicillin. This culture will be grown to an $A_{600=0.2}$, when it will then be superinfected with a 10–20 fold excess of helper phage M13K07. After exactly 4 hours the culture will be harvested, single-stranded DNA will be isolated and purified through HAP and agarose gel electrophoresis as described in the Preliminary Results section. This material will then undergo the normalization protocol to generate the human cDNA catalogue. Applicants will utilize the ½Not-Pac-(dT)15 degenerate oligonucleotide for the controlled primed extension reaction involved in the normalization procedure. If this primer will prove inadequate, applicants have the choice of performing the annealing reaction in the presence of all 14 specific Pac-(dT)17–18 oligonucleotides.

As in the other cases, the extent of normalization of the cDNA catalogue may be assessed by screening the library (colony hybridization) with a panel of cDNA probes representing prevalent, moderate and rare mRNAs.

In addition, 100 randomly picked clones (single pass sequencing from the 3' end only) will be sequenced to estimate the frequency of each library component in the cDNA catalogue.

Subtractive hybridization of normalized libraries

The Strategy to be utilized for subtractive hybridization of cDNA libraries will be very similar to that described by Swaroop et al. (1991) for the isolation of retina specific cDNAs. Two strategies will be compared.

(1) Synthesize biotinylated run-off transcripts with Bio-11-UTP (Enzo Biochem) and then use vectrex-avidin (Vector Laboratories) to capture the hybrids and thereby purify (flow-through) the unhybridized single-stranded circles (tissue-specific sub-library) which can then be electroporated into bacteria (after conversion to partial duplexes by random priming for improvement of electroporation efficiencies).

(2) Synthesize non biotinylated run-off transcripts and then use HAP column chromatography to separate the remaining single-stranded material (subtracted library, HAP-flow-through) from the RNA-DNA hybrids (HAP-bound).

Supercoiled plasmid DNA from a normalized library will be linearized with Sfi I and in vitro transcribed from the T3 promoter (run-off transcription) to generate large quantities of antisense RNA which will be complementary to any of the directionally cloned normalized libraries in the form of single-stranded circles (mRNA-like strand). The reactions will be performed with the "Riboprobe Gemini II In Vitro Transcription System" (Promega, Cat#P2570), according to the manufacturer's instructions. A cDNA in the pT7T3-Pac vector has been subcloned to test its ability to drive transcription off the T7 and T3 promoters, and very good yields of RNA were obtained in both cases. Very good yields of single-stranded DNA circles with this plasmid (better with M13K07 than with R408) are routinely obtained.

The in vitro synthesized RNA will then be hybridized to single-stranded circles from normalized libraries. However, since the first 15–20 nucleotides at the 5' end of the in vitro synthesized RNA will be complementary to the sequence of the polylinker immediately flanking the Pac I cloning site, precautions need to be taken to prevent hybridization between RNA and single-stranded circles through such sequences. Applicants plan to synthesize a "blocking" oligonucleotide, which will have the same sequence of the single-stranded circles in that region [5' (A)$_{18}$NNNNTTAATTAAGCGGCCGCAAGCTTATT 3', SEQ ID No. 26]. Thus, to prevent hybridization through such sequences the RNA will first be annealed to an excess of the blocking oligonucleotide, and then digested with RNAse H, which will eliminate that very sequence form the RNA (RNAse H attacks the RNA strand of a DNA:RNA hybrid). The sample will be digested with RNAse-free DNAse, which will destroy both the excess blocking oligonucleotide and the linearized plasmid DNA template, and then hybridized to the single-stranded circles.

Typically 0.2 μg of a single-stranded DNA will be hybridized to 20 μg of RNA for 72 hours at 42°–45° C. in a 10 μl reaction containing 0.5M Sodium Phosphate pH 7.2, 10 mM EDTA, 0.1% SDS, 50% formamide (Cot of approximately 3,000). The remaining single-stranded circles (normalized tissue-specific sublibrary) will be purified either by HAP chromatography or by affinity (lack of) to vectrex-avidin, as discussed above. Applicants have vast experience with HAP and applicants know for fact that it is very reliable for this kind of purification. Thus, at least this approach is guarantee to work, but nonetheless applicants will compare efficiencies with the alternate method. After purification, the single-stranded material will be converted to partially duplex DNA by random priming (just as applicants have been routinely doing at the end of the normalization procedure) and electroporated into bacteria for propagation under ampicillin selection.

Model system for optimization of conditions for subtractive hybridization of normalized libraries.

As a model system for optimization of conditions for subtractive hybridizations involving normalized libraries applicants will isolate hippocampus-specific cDNAs (see FIG. 3). Two normalized libraries will be utilized: adult brain library: a collection of tissue samples representing all regions of the brain with the exception of hippocampus) and adult hippocampus library, obtained from the same brain of that utilized for construction of the adult brain library). In vitro synthesized RNA from the adult brain library (driver) will be hybridized (high Cot) to a mixture of single-stranded circles from both adult brain and adult hippocampus libraries (tracers), and the remaining single-stranded circles (hippocampus-specific normalized sub-library) will be purified as discussed above. The presence in the hybridization of single-stranded circles from adult brain library will serve as a built in control. If completion of hybridization is achieved, no single-stranded circles from adult brain library should remain unhybridized. Verification that the subtracted library really corresponds to hippocampus-specific cDNAs will be straightforward by single-pass sequencing (3' end sequencing with the M13 Universal Primer or with a primer complementary to the T3 promoter) of a number of randomly picked clones from the subtracted library. This will be possible because clones from these two libraries can be discriminated by their specific sequence identifiers. So, if all clones from the subtracted library will indeed have the sequence identifier of the hippocampus library applicants will know that the subtraction worked efficiently and that applicants will have isolated a collection of hippocampus-specific cDNA clones.

It should be emphasized that the bound material (either HAP-bound or avidin-bound) will also be informative. Clones from the hippocampus library present in the bound fraction will represent mRNAs that are common to hippocampus and some other (or all other) region of the brain. However, applicants will concentrate on the flow-through (tissue-specific) material.

Since this will be a test system, applicants will (in addition to sequencing) also demonstrate tissue-specificity by RNAse protection assays (just this first time) Once verified, applicants will have established a very effective and straightforward way to isolate and verify tissue-specificity of a subtracted library. From there on applicants will do all verifications by single-pass sequencing only.

Applicants will certainly also sequence about 50 clones from the original mixture of single-stranded circles from adult brain and adult hippocampus libraries (the very mixture that will be used as tracer in the hybridization) to assess relative frequencies of clones from the two libraries (the expectation would be to find each at a frequency of about 50%). Applicants will then first sequence 20 clones from the subtracted library. Depending on the extent to which the ratio of clones from the two libraries deviated from the starting frequency of 50% each, applicants will decide whether or not a second round of hybridization should be performed. If it will be necessary applicants will just make single-stranded circles from the first subtracted sub-library and hybridize it to a large excess (100-fold) of in vitro synthesized RNA from library #1 again. Once the sequence data will indicate purity of the subtracted sublibrary (all hippocampus-specific clones) applicants will go on and sequence up to 100 clones to derive a solid and statistically significant number. Each clone will then be sequenced from both 5' and 3' ends. It is applicants' experience that because the sequence obtained from 5' end of a clone will often correspond to coding information, the chances of identifying homologies through database searches increase rather significantly.

All DNA sequencing will be done using applicants' ABI DNA Sequencer. Applicants also have a Biomek workstation where all sequencing reactions are routinely performed. Blast searches (Altschul et al., 1990) will be done through e-mail to the NCBI server. Applicants do database searches on a daily basis in the context of another ongoing project in the laboratory to isolate chromosome 13-specific cDNAs.

Finally, applicants will estimate the complexity of the subtracted library by performing a number of colony hybridization experiments. Since the subtracted library will be normalized, the frequency of any clone should be within a narrow range. Therefore, applicants should be able to estimate the total number of different clones in the subtracted library by hybridizing 10,000 or so colonies from the subtracted library with a battery of randomly picked cDNA probes from the same subtracted library. If for instance each of 10–20 probes will be represented at a frequency of 0.1–0.5%. applicants will know that there might be 500–1, 000 different hippocampus-specific cDNA clones in the subtracted library.

Subtractive hybridizations involving different normalized libraries and the cDNA catalogue.

Once applicants have optimized all conditions with the model system described above, applicants will take advantage of the availability of all individual normalized libraries and the cDNA catalogue to generate a number of tissue-specific and developmental-specific sub-libraries.

The plan is to utilize as a driver a mixture of in vitro synthesized RNA from all but one of the normalized library components of the cDNA catalogue, in a hybridization where the tracer will be single-stranded circles form the cDNA catalogue (which contains all libraries including that one missing in the driver) [see FIG. 4]. In other words, supercoiled plasmid DNA from each individual normalized library (except one) will be linearized and separately utilized as templates for in vitro synthesis of RNA. After annealing to the blocking oligonucleotide, and digestion with both RNAse H and RNAse-free DNAse, as detailed above, all synthesized RNAs (20–40 μg) will be pooled together and hybridized to trace amounts (0.1 μg) of single-stranded circles from the cDNA catalogue. If hybridization goes to completion, only-single stranded circles from the library missing in the driver should be found in the flow-through (HAP or vectrex-avidin) fraction. Once again, verification of tissue-specificity would be easily accomplished by single-pass sequencing.

For example applicants plan to use this system to isolate embryonic-specific cDNAs.

Similarly applicants will attempt to isolate brain (fetal, infant and adult), liver (fetal, infant and adult), spinal cord (adult), lung (infant), heart (infant), spleen (infant) and muscle (infant) -specific subtracted libraries. Applicants will sequence 100 clones from each subtracted library and applicants will estimate their complexities by colony hybridization experiments, as described above.

Applicants anticipate that such resources will prove valuable for many purposes, e.g. identification of novel tissue and temporal-specific transcripts, chromosomal localization of differentially expressed genes (by painting chromosomes with pools of clones from tissue-specific sub-libraries; since cDNA inserts are large in applicants' libraries this should be straightforward by fluorescence in situ hybridization). Furthermore, the availability of this cDNA catalogue as a reference library should facilitate ongoing efforts for isolation of chromosome-specific cDNAs, large sequencing of cDNAs, and cloning of disease-causing genes. Methods for identification of transcribed sequences from genomic DNA, such as exon trapping (Duyk et al., 1990; Hamaguchi et al., 1992), exon amplification (Buckler et al., 1991), cDNA selection (Parimoo et al, 1991), and direct selection (Lovett et al., 1991; Morgan et al., 1992) should also benefit from this cDNA catalogue. "Exon amplification" and "exon trapping" are methods that take advantage of RNA splicing to capture expressed sequences from large regions of genomic DNA. "Direct selection" and "cDNA selection" utilize a genomic target DNA, a YAC clone for example, for hybrid selection of cDNAs. At the end either the small exons that were trapped or the short cDNA fragments that were selected need to be utilized to "fish" more informative cDNA clones from high quality cDNA libraries. Applicants also have developed a method for hybrid selection of cDNA clones (as single-stranded circles with filter immobilized genomic DNA, which applicants are utilizing to identify chromosome 13-specific cDNAs (Bonaldo et al., manuscript in preparation). However, to identify as many transcribed sequences as possible from any given region of DNA applicants would have to go through selections with a number of different libraries, as opposed to only one, if the cDNA catalogue were already available.

As mentioned before, applicants plan to make these resources available to all interested investigators. As an example, applicants' infant brain library has been distributed to many institutions in the USA and abroad (Lawrence Livermore, Argonne Laboratories, Harvard Medical School, University of Colorado, NIH, University of Pennsylvania, Genethon (France), MRC (Cambridge) and Rijks University (The Netherlands).

Human Subjects 1 and 2. The fetal tissues required for this project will be obtained from voluntary pregnancy terminations. These terminations are usually by suction curettage. The products of conception are considered surgical pathology specimens (category 5 of exceptions) that are discarded after examination. Voluntary terminations are suitable for this project because the procedures are scheduled, the tissues are fresh, and genetic abnormalities are usually absent. Tissues will be obtained from the Short Stay Surgical Unit of the Presbyterian Hospital through the cooperation of members of the Departments of Obstetrics and Gynecology, and Pathology. Dr. Stephen Brown, who is both a member of applicants' team and a faculty member in OBGYN, will serve as a liaison. All specimens will be identified by accession number, and no names of patients will be kept.

3. Since the tissues that applicants will collect are normally discarded pathological specimens, and no identification information will be retained, there will be no contact with the patients.

4, 5 and 6. The subjects are not exposed to any kind of potential risk by this study, because no additional procedures are carried out, and only the pathological material from non-viable products of conception will be used. The study does not involve persons under the age of 18 nor any drugs, medical devices or questionnaires.

References of the First Series of Experiments

1. Adams, M. D., et al. (1991). Complementary DNA sequencing: expressed sequence tags and human genome project. Science 252:1641–1656.
2. Adams, M. D., et al. (submitted for publication). Rapid cDNA Sequencing (Expressed Sequence Tags) from a Directionally Cloned Human Infant Brain cDNA Library.
3. Atschul, S. F., et al. (1990). Basic local alignment search tool. J. Mol. Biol. 215:403–419.
4. Bishop, J. O., et al. (1974). Nature 250:199–204.
5. Britten, R. J., et al. (1974). Analysis of repeating DNA sequences by reassociation. Meth. Enzymol. 29:363–441.
6. Buckler, A. J., et al. (1991). Exon amplification: a strategy to isolate mammalian genes based on RNA splicing. Proc. Natl. Acad. Sci. USA 88:4005–4009.
7. Davidson, E. H. and Britten, R. J. (1979). Science 204:1052–1059.
8. Dear, T. N., et al. (1991). Novel genes for potential ligand-binding proteins in subregions of the olfactory mucosa. EMBO J. 10(10):2813–2819.
9. Dear, T. N., et al. (1988). Differential expression of a novel gene, WDNM1, in nonmetastatic rat mammary adenocarcinoma cells. Cancer Res. 48:5203–5209.
10. Dower, W. J., et al. (1988). High Efficiency transformation of E.coli by high voltage electroporation. Nuc. Acids Res. 16(3);6127–6145.
11. Duguid, J. R., et al. (1988). Isolation of cDNAs of scrapie-modulated RNAs by subtractive hybridization of a cDNA library. Proc. Natl. Acad. Sci. USA 85:5738–5742.
12. Duyk, G. M., et al. (1990). A genetic screen to identify candidate transcribed sequences in cloned mammalian genomic DNA. Proc. Natl. Acad. Sci. USA 87:8995–8999.
13. Galau, G. A., et al. (1977). Arch. Biochem. Biophys. 179:584–599.
14. Hamaguchi, M., et al. (1992). Establishment of a highly sensitive and specific exon-trapping system. Proc. Natl. Acad. Sci. USA. 89:9779–9783.
15. Hara, E., et al. (1991). Subtractive cDNA cloning using oligo(dt)30-latex and PCR: isolation of cDNA clones specific to undifferentiated human embryonal carcinoma cells. Nuc. Acids Res. 19(25):7097–7104.
16. Huynh, T. V., et al. (1985). Constructing and Screening cDNA Libraries in λgt10 and λgt11. In "DNA Cloning Volume I" (ed. D. M. Glover), pp. 49–78. IRL Press Limited, England.
17. Khan, A. S., et al. (1992). Single pass sequencing and physical and genetic mapping of human brain cDNAs. Nature Gen. 2:180–185.
18. Kho, C-J and Zarbl, H. (1991). A rapid and efficient method for the generation of a subtracted cDNA library. Technique 3(2):58–63.
19. Klar, A., et al. (1992). F-Spondin: a gene expressed at high levels in the floor plate encodes a secreted protein that promotes neural cell adhesion and neurite extension. Cell 69:95–100.
20. Ko, M. S. H. (1990). An "equalized cDNA library" by the reassociation of short double-stranded cDNAs. Nuc. Acids Res. 18:5709.
21. Kornberg, A. and Baker, T. A. (1992). RNA-Directed DNA Polymerases: Reverse Transcriptases and Telomerase. In "DNA Replication", 2nd Edition, pp. 21714 222. W. H. Freeman and Company, New York.
22. Krady, J. K., et al. (1990). Use of avidin-biotin subtractive hybridization to characterize mRNA common to neurons destroyed by the selective neurotoxicant trimethyltin. Mol. Brain Res. 7:287–297.
23. Lee, S. W., et al. (1991). Positive selection of candidate tumor-suppressor genes by subtractive hybridization. Proc. Natl. Acad. Sci. USA 88:2825–2829.
24. Loros, J. J., et al. (1989). Molecular cloning of genes under control of the circadian clock in Neurospora. Science 243:385–388.
25. Lovett, M., et al. (1991). Direct selection: a method for isolation of cDNAs encoded by large genomic regions. Proc. Natl. Acad. Sci. USA 88:9628–9632.
26. Miller, F. D., et al. (1987). J. Neurosci. 7(8):2433–2444.
27. Morgan, J. G., et al. (1992). The selective isolation of novel cDNAs encoded by the regions surrounding the human interleukin 4 and 5 genes. Nuc. Acids Res. 20(19):5173–5179.
28. Owens, G. P., et al. (1991). Identification of mRNAs associated with programmed cell death in immature thymocytes. Mol. Cell. Biol. 11(8):4177–4188.
29. Parimoo, S., et al. (1991). cDNA selection: efficient PCR approach for the selection of cDNAs encoded in large chromosomal DNA fragments. Proc. Natl. Acad. Sci. USA 88::9623–9627.
30. Patanjali, S. R., et al. (1991). Construction of a uniform-abundance (normalized) cDNA library. Proc. Natl. Acad. Sci. USA 88:1943–1947.
31. Rubenstein, J. L. R., et al. (1990). Subtractive hybridization system using single-stranded phagemids with directional inserts. Nuc. Acids Res. 18(16):4833.
32. Sive, H. L. and St. John, T. (1988). A simple subtractive hybridization technique employing photoactivable biotin and phenol extraction. Nuc. Acids Res. 16(22):10937.
33. Smith, C. L., et al. (1987). Strategies for mapping and cloning macroregions of mammalian genomes. Methods in Enzimol. 151:461–489.
34. Swaroop, A., et al. (1991). A simple and efficient cDNA library subtraction procedure: isolation of human retina-specific cDNA clones. Nuc. Acids Res. 19(8):1954.
35. Sykes, D. E. and Weiser, M. M. (1992). The identification of genes specifically expressed in epithelial cells of the rat intestinal crypts. Differentiation 50:41–46.
36. Travis, G. H. and Sutcliffe, J. G. (1988). Proc. Natl. Acad. Sci. USA 85:1696–1700.
37. Travis, G. H. et al. (1987). Subtractive cloning of complementary DNAs and analysis of messenger RNAs with regional heterogeneous distributions in primate cortex. Neuropharmacol. 26(7B):845–854.
38. Weissman, S. M. (1987). Molecular genetic techniques for mapping the human genome. Mol. Biol. Med. 4:133–143.
39. Yancopoulos, G. D., et al. (1990). Isolation of coordinately regulated genes that are expressed in discrete stages of B-cell development. Proc. Natl. Acad. Sci. USA 87:5759–5763.
40. Zabarovsky, E. R. and Weinberg, G. (1990). High efficiency electroporation of ligated DNA into bacteria. Nuc. Acids Res. 18(19):5912.

Second Series of Experiments
INTRODUCTION

Two strategies have been proposed to normalize cDNA libraries, the "genomic" and the "kinetic" approaches (Weissman, 1987). The genomic approach is based on hybridization of saturating amounts of cDNA to genomic DNA. The frequency of each hybridized cDNA in the resulting normalized library would be proportional to that of each corresponding gene in genomic DNA. The requirement that even the rarest cDNAs be present at saturating levels, however, makes this approach technically cumbersome. The alternative is the kinetic approach: if cDNA re-annealing follows second-order kinetics, rarer species anneal less rapidly and the remaining single-stranded fraction of cDNA becomes progressively more normalized during the course of the hybridization (Galau et al., 1977). Specific loss of any species of cDNA, regardless of its abundance, does not occur at any Cot value.

The kinetic approach has been successfully utilized to normalize cDNA libraries by two independent groups (Ko, 1990; Patanjali et al., 1991).

Ko (1990) constructed a normalized mouse cDNA library by a scheme involving ligation of sheared cDNAs (200–400 bp) to a linker-primer adaptor, and one to three cycles of: (i) PCR amplification, (ii) denaturation-reassociation, and (iii) purification of the remaining single stranded cDNAs by hydroxyapatite (HAP) column chromatography. The resulting single-stranded material was PCR amplified, digested at a site present in the linker-primer sequences. Colony hybridization with eight probes of different abundances showed a reduction in abundance variation from at least 20,000 fold in the original library to 40-fold in the library constructed after three cycles of normalization.

Patanjali et al (1991) reported the utilization of a similar strategy to normalize a human adult thymus cDNA fragments into γgt10, (ii) PCR amplification of cloned cDNAs, (iii) denaturation and reassociation to moderate Cot, (iv) separation of single-strands by HAP Chromatography, (v) PCR amplification of HAP-flow-through single-stranded cDNA and (vi) cloning into γgt10. This procedure differs from Ko's (1990) in that both coding and non coding sequences are represented in the final library. The starting cDNA fragments were size selected [400–1,600 bp] to minimize length dependent differential PCR amplification.

As discussed by Ko (1990), coding sequences from different members of a gene family are likely to cross-hybridize during the reassociation reaction. Since some gene family members may be much more prevalent than others, there is a potential risk that the least frequent member be eliminated from the final library. 3' untranslated sequences of mRNAs, on the other hand, are usually unique to individual transcripts. For this reason Ko (1990) utilized short cDNAs for the reassociation reaction, and forced the cloning of those fragments containing 3' untranslated sequences only.

Applicants have developed a method for normalization of directionally cloned cDNA libraries constructed in phagemid vectors, which is also based on the kinetic principle. Briefly, the method involves annealing of the library in the form of single-stranded circles to a NotI oligo (dT)18 primer, and controlled extensions (200–250 nt) with Klenow in the presence of dNTPs and ddNTPs to generate a cDNA library in the form of partially duplex circular DNA molecules that can then be normalized by the kinetic approach, i.e melting and re-annealing to moderate Cot, and purification of the unreassociated single-stranded circles (normalized library) by hydroxyapatite column chromatography. Since the unreassociated material (HAP-flow-through) consists of already cloned cDNAs in the form of single-stranded circles, they can be readily electroporated into bacteria and propagated under appropriate antibiotic selection. This is in contrast to the alternative methods, according to which at the end of the reassociation reaction the remaining single stranded cDNAs need to be amplified by PCR and cloned.

Because this method does not require any cycle of cDNA amplification by the polymerase chain reaction, there are no length constraints on the cDNAs, and the normalized library consists of cDNA clones that have large size inserts (average of 1.7 kb).

It is noteworthy that although both coding and non-coding exons are represented in the normalized library, only 3' non-coding sequences participate in the reassociation reaction, thus minimizing the risk of eliminating low copy cDNAs due to cross hybridization between their coding sequences and those of other family members that are represented at a higher frequency in the starting cDNA library.

Here, applicants report the utilization of this method to construct a normalized human infant brain cDNA library in which the frequency of each clone is within a narrow range.
MATERIALS AND METHODS
Preparation of a directionally cloned human brain cDNA library Total cellular RNA from a 73 day old post-natal female human brain was extracted according to a modification (Puissant and Houdebine, 1990) of the procedure described by Chomczynski & Sacchi (1987), and poly (A)+ RNA was purified by standard procedures (Sambrook et al., 1989). A detailed description of the protocol utilized for construction of this human infant brain cDNA library has been provided elsewhere (Soares, in press).

Briefly, a Not I (dT)18 oligonucleotide [5'AACTGGAAGAATTCGCGGCCGCAGGAA(T)18, SEQ ID No. 4] was utilized as primer for first strand cDNA synthesis. After ligation to Hind III adapters, the cDNAs were digested with Not I (after appropriate size selections) and directionally cloned into the Hind III and Not I sites of a plasmid vector (lafmid BA) derived from pEMEL. The polylinker of the lafmid BA vector contains the following restriction sites: 5' Hind III-Bam HI-Not I-Eco RI 3'. The vector has an f1 origin for production of single-stranded circles upon super infection with a helper phage. Single-stranded library DNA represents the message (mRNA-like) strand and therefore all single-stranded circles contain a short polyadenylic acid tail at their 3' end. The high representation of mRNA sequences in this library has been firmly documented by single pass sequencing of over 2,000 randomly picked clones (Khan et al., 1992; Adams et al., in press). The main features of this library are: (1) average cDNA size of 1.6 kb; (2) short polyadenylic acid tails; (3) non recombinants account for less than <0.1% of the clones; (4) chimeric cDNA clones have not been identified yet.
Propagation of cDNA libraries in the form of single-stranded circles 1–10 ng supercoiled plasmid DNA representing the entire library was electroporated into dH5αF' (electroporation efficiency of 5×10 9 c.f.u/mg supercoiled plasmid), grown at 37° C. for 1 h and then propagated under ampicillin selection overnight. The culture was then diluted 100 fold with fresh medium and grown in the presence of 0.2% glucose under ampicillin selection to A600–0.2. At this time the culture was superinfected with a 10–20 fold excess of helper phage (R408 or M13K07) and grown for only 4 h. Single-stranded DNA was then prepared according to standard protocol.

Single stranded circles were purified from any residual double-stranded plasmid (RF) contaminant as follows: 20 mg single stranded library DNA in 2 mls 0.12M PB-1% SDS-10 mM EDTA were passed through 0.4 g HAP-60° C., pre-equilibrated with 0.12M PB-10 mM EDTA-1% SDS, the column was washed with 6 mls loading buffer and the combined HAP-flow-through (single-stranded circles in a total of 8 mls) was extracted twice with 30 mls H2O-saturated sec-butanol, once with 30 mls dry sec-butanol, once with 30 mls dry sec-butanol, and once with 20 mls of H2O saturated ether. The ether was blown off, and the sample was desalted by passage through a Nensorb column (DuPont) according to the manufacturer's instructions. [It should be noted that single-stranded circles are very sensitive to high temperatures (electroporation efficiencies of single-stranded circles drop very dramatically upon boiling, for example). However, a quick (1–2 min per passage) purification through a 60° C.-HAP column does not damage single-stranded circles in applicants' hands.

HAP-purified single-stranded DNA was then purified from any residual amount of tRNA and from most of the helper phage DNA by agarose gel electrophoresis. The agarose gel slice containing the single-stranded library DNA smear was casted into a low melting point agarose gel, the current was reversed and the DNA was electrophoresed backwards (just to sharpen the smear) until it entered the low melt agarose gel. The low melt gel slice containing the library DNA was digested with—agarose (NEE) and the single-stranded circles were ethanol precipitated. This gel purification step proved to be necessary to avoid undesirable internal priming events promoted by small RNA oligonucleotides (breakdown products from RNAse A digestion of tRNAs). The single-stranded DNA was never exposed to U.V. light [A small fraction of it was run on a separate lane, which was exposed to U.V., and served as a reference; this DNA was not used].

Applicants have performed control colony hybridization experiments to show that the frequency of several of the abundant clones (α-tubuli, elongation factor 1α, -tubuli and myelin basic protein) was absolutely identical in both the starting double-stranded library and in the library in the form of single-stranded circles. Thus, if prepared under the conditions described above, the library in the form of single-stranded circles is perfectly representative of the starting library.
cDNA library Normalization See FIG. 1. for a schematic representation of the normalization procedure.

a) 0.6 pmoles of a ½ Not I-(dT)15 oligonucleotide [5'GGCCGCAGGAA(T)15 3', SEQ ID Nos. 5 and 6] were added to 0.3 pmoles of single-stranded circles (library DNA) in a 10 ul reaction containing 30 mM Tris pH7.5–50 mM NaCl–15 mM MgCl2–1 mM DTT-0.1 mM each deoxynucleotide (dA,dC,dT, and dG)–2.5 mM each dideoxynucleotide (ddA,ddC and ddG; but no ddT)-and a trace of α32pdCTP. The mixture was first incubated for 5 min at 60° C., and then for 15 min at 50° C. (annealing temperature). At that time, the temperature was lowered down to 37° C., 5 units of Klenow enzyme were added and the reaction remained at 37° C. for 30 min. 15 such reactions were carried out in parallel. The end product of these reactions were partial duplex circles. The size distribution of the synthesized strand was rather narrow (200 nt±20; see FIG. 2 lane 3). [Since 3' non coding exons are usually larger than 300 nt (average of 750 nt in brain), the vast majority of the synthesized material should correspond to 3' untranslated sequences]. [Klenow was the only polymerase among several tested (T4 DNA Polymerase, Vent DNA Polymerase, Reverse Transcriptase and T7 DNA Polymerase) to generate extension products with such a narrow size distribution]. The next step was to purify these partially duplex circular molecules from any remaining (unprimed) single-stranded circles by HAP chromatography c) All 15 reactions were pooled together and stopped with EDTA (20 mM f.c.). The sample was extracted with phenol +Sevag, and phosphate buffer (PB) was added to a final concentration of 0.12M. At this time 2 mls of 60° C.-prewarmed 0.12M PB-10 mM EDTA-1% SDS containing 50 ug denatured sonicated salmon sperm DNA were added to the sample and this mixture was passed through a hydroxyapatite (HAP) column at 60° C. The column (0.4 g HAP, about 1 ml bed volume) had been pre-equilibrated with 0.12M PB. After a wash with 6 mls of 0.12M PB-10 mM EDTA-1% SDS, the partial duplex circles (HAP -bound) were eluted off the column with 6 mls of 0.4M PB-10 mm EDTA-1% SDS. 14 mls H2O containing 50 ug denatured sonicated salmon sperm DNA were added to this eluate to lower the PB concentration down to 0.12M PB f.c., the column was reequilibrated with 0.12M PB-10 mM EDTA-1% SDS and the sample was passed through HAP again. [This is necessary because a small fraction of single-stranded DNA can bind, non specifically to HAP; this background is of the order of 0.1%; by passing it through twice this background becomes irrelevant]. The column was washed with 6 mls 0.12M PB-10 mM EDTA-1% SDS and the partially duplex circles (HAP-bound) was eluted with 6 mls 0.4M PB-10 mM EDTA-1% SDS.

d) The eluate was desalted by passage through a Nensorb column (DuPont), after a few extractions with H2O-saturated and dried sedbutanol. DNA was eluted off the Nensorb column with 1 ml 20% n-propanol in H2O, vacuum-dried for 30 min, (at this point an aliquot of the material was applied on a 6% sequencing gel; see FIG. 2) and ethanol precipitated.

e) The DNA pellet (112.5 ng) was resuspend in 2.5 ul formamide and heated for 3 min at 80° C. under a drop of mineral oil. 1 ul 5 ug/ul oligo-(dT) 25–30, 0.5 ul 1 ug/ul ½ Not-(dT)15 oligonucleotide, 0.5 ul 5M NaCl, and 0.5 ul 0.1M Tris-0.1M EDTA (total 5 ul) were added and the mixture was incubated at 42° C. [oligo-(dT) 25–30 and ½ Not-(dT)15 oligonucleotides were present to block the polyadenylic acid tails]. 0.5 ul aliquots were taken at 13 h (Cot-8) and 84 h (Cot-51.5). The best normalization results (see Table 1) were obtained after 13 h incubation.

f) in the next step, the remaining (normalized) single stranded circles were separated from the (reassociated) partially double-stranded circular molecules by HAP chromatography.

To 0.5 ul of the hybridization mixture, applicants added 5 ug of denatured sonicated salmon sperm DNA+2 mls of 60° C. prewarmed 0.12M PB-10 mM EDTA-1% SDS and the sample was passed through 0.4 g HAP. The column was washed with 6 mls 0.12M PB-10 mM EDTA-1% SDS and the HAP-flow-through (containing the normalized single-stranded circles) was passed through a second (fresh) HAP column just to minimize the chance that any residual amount of partially double-stranded molecules escaped from binding through some undetected small channel in the column; by passing it through a fresh column this potential problem was eliminated. The column was washed with 6 mls 0.12M PB-10 mM EDTA-1% SDS and the flow-through material (normalized single-stranded circles) was desalted through a Nensorb column as described above. HAP-bound DNA from the first column was also purified.

g) At this point, one can either directly electroporate the single-stranded circles (HAP-flow-through) into competent DH10B bacteria, or one may convert them into partially double-stranded circles (by primed extension) in order to improve their electroporation efficiencies by 50–100 fold. Such extensions can be primed with random hexamers, or with the M13 Universal primer.

After 1 h at 37° C., an aliquot of the culture (10 ul out of 100 mls) was plated on an LE agar plate containing ampicillin for determination of total number of transformants, ampicillin was added to the culture to a final concentration of 75 ug/ml, and the bacteria were propagated till the culture reached mid-log phase. Supercoiled plasmid DNA (normalized library) was extracted by alkaline lysis and purified over a Qiagen midi-size column. Applicants obtained 2.5 million transformants from the 0.5 ul of hybridization mixture that were processed.

Colony hybridization

Colony hybridizations were done essentially as described (Grunstein). For best results while making replica filters with nylon membranes (GeneScreenPlus) the plate with bacteria should be kept at 4° C. for 1–2 hours, the master filter (first to be pulled off the plate) should not be pre-wetted whereas the second filter (to be pulled off the master filter) should be pre-wetted on an empty agar plate. Hybridization and washing conditions were as described before (Zeitlin & Efstratiadis).

DNA sequencing

Double-stranded plasmid DNA templates were prepared using MagidPrep (Promega) or Qiagen columns as described by the manufacturer's instructions.

DNA sequencing was performed by the cycle sequencing protocol (ABI) according to the manufacturer's instructions, using an automated ABI370A DNA Sequencer.

Database searches

Blastn and Blastx database searches were performed at the NCBI using the BLAST network service. [Altschul, Stephen F., Warren Gish, Webb Miller, Eugene W. Myers, and David J. Lipman (1990). Basic local alignment search tool. J. Mol. Biol.215:403–410.]

EXPERIMENTAL RESULTS

The efficiency of normalization was assessed by three criteria: (a) colony hybridization of both starting and normalized libraries with a number of cDNA probes representing mRNAs that occur in the starting library at a wide range of frequencies (Table 1), (b) screening of the normalized library with a number of cDNA probes derived from clones that were randomly pricked from the normalized library itself, and (c) by single-pass sequencing (from both the 5 and 3' ends) of approximately 200 cDNA clones (over 100 kb total sequence). Altogether these results strongly indicate that normalization was successful.

The cDNA probes that were utilized for screening of both starting and normalized libraries can be arbitrarily grouped into 3 classes: prevalent, with frequencies in the starting library ranging from 0.5–5%, intermediate (0.05–0.5%) and complex (<0.05%). Normalization reduced the frequency of the prevalent cDNAs by about 10–100 fold (with the exception of mitochondrial 16S rRNA, see below), that of the intermediates by 3–16 fold, whereas the frequency of the cDNAs from the complex class remained practically the same. The difference in frequency between the most and the least abundant clones in the starting library (elongation factor 1-α at 4.6% and cDNA#250-1 at 0.008%) was reduced from 575 down to 3 with the normalization procedure.

As described in the method's section, an aliquot of the hybridization mixture was passed over HAP to separate the remaining single-stranded circles (HAP-flow-through, normalized library) from the reassociated partially duplex molecules (HAP-bound). Both HAP-flow-through and HAP-bound fractions were processed so that applicants could verify that the frequency of an abundant cDNA was lowered in the normalized library (HAP-flow-through), because it reassociated fast and therefore it ended up in the HAP-bound fraction. Indeed, the frequency of two of the most abundant clones in the starting library [elongation factor 1-α (4.6%) and α-tubulin (4%) was reduced 100 fold (0.4% and 0.5%, respectively) in the HAP-flow-through fraction (normalized library) but remained high (3.7% and 6%, respectively) in the HAP-bound-fraction (the reassociated material), further documenting the efficacy of the kinetic approach to normalize cDNA libraries].

If a library is normalized, one would expect that any randomly picked clone would be represented within a narrow range of frequencies. To test this hypothesis, eight clones were randomly picked from the normalized library, and probes made from them were used to screen the normalized library itself. The frequency of all eight cDNAs fell within a 13-fold range, varying from 0.003% to 0.04%. Overall, based on colony hybridization experiments with 27 probes, the frequency variation in the normalized library is of the order of 50 fold (the 16S mitochondrial rRNA was excluded from this analysis, see below).

To further document that normalization was successful, 190 cDNA clones were randomly picked from the normalized and single-pass sequenced from both ends. Database searches of the public nucleic acid and protein databases revealed that 69% ($^{31}/_{190}$) of the clones correspond to novel brain expressed sequences: no matches could be identified in the public nucleic acid or protein databases to either their 3' or 5' end sequences. 19% ($^{25}/_{131}$) of those contained repetitive elements (mostly Alu) in either their 3' or 5' ends. 25% ($^{48}/_{190}$) of the clones had matches to known human sequences, 50% ($^{24}/_{48}$) of which to "ESTs to unknown genes". 6% ($^{12}/_{190}$) of the clones were putatively identified based on similarities to known sequences of other organisms, (mainly Rodent, Drosophilia, yeast or *C.elegans*). Among those putative identifications are an homologue of the yeast pr-mRNA splicing factor RNA helicase PRP22, a homologue of a Drosophila GTP-binding protein, the homologue of the Drosophila puff specific protein Bx42, and cDNAs similar to the *Streptomyces exfoliatus*-20beta-Hydroxysteroid dehydrogenase, yeast hypothetical 43.3 kd protein, Chines hamster DHFR-coamplified protein mRNA, and Rat plasma membrane Ca2+ ATPase-isoform 2 mRNA.

1,633 randomly picked clones from this same infant brain library (prior to normalization) have been single-passed sequenced (mostly from their 5' ends) [Adams et al., in press]. 37% of the clones were putatively identified by database searched, and 63% corresponded to sequences with not matches in the databases.

Applicants have performed Fasta searches of all 5' sequences obtained from those 190 clones that were randomly picked from the normalized library against 1624 sequences (kindly provided by M. Adams, TIGR) that were generated by random picking of clones from the same infant brain library prior to normalization. Only 8% ($^{15}/_{190}$) of the clones randomly picked from the normalized library had already been identified within those 1624 sequences derived from the non normalized library. Three of these matches corresponded to overlapping clones (cDNA clones of different lengths presumably derived from the same mRNA) rather than to the same clone. Five of these 15 clones corresponded to sequences not previously identified (no matches in the public databases). Five of them corresponded to already identified "ESTs to unknown genes". Five of them corresponded to known human sequences: mitochondrial 16S rRNA (3 clones), a human cDNA similar to mouse cysteine-rich protein and a human 23 Kd highly basic protein.

Similarly, 178 sequences were randomly selected from the 1624 ESTs derived from the non normalized library, and Fasta searched against the remainder 1446 sequences. 31% ($^{55}/_{178}$) of those had matches among the 1446 ESTs, i.e. they were represented at least twice in the original pool of 1624 sequences. Many hits were found to all those cDNA clones representing the prevalent mRNAs such as elongation factor 1-α, elongation factor 1y, α-tubuli, B-tubuli, y-actin and myelin basic protein.

EXPERIMENTAL DISCUSSION a) The method is advantageous because there is no PCR involved and because only 3' non coding sequences participate in the reassociation reaction.

b) Internal priming is a potential problem, and it can explain how come the frequency of 16S mitochondrial rRNA did not go down as it should have after normalization. Applicants have obtained sequence data from a number of 16S clones from the starting and normalized libraries. All clones in the starting library are full length or near full length. Most 16S rRNA clones in the normalized library are truncated versions generated by internal priming. The interpretation is that the extension products of both the full length and truncated circle templates can reassociate to the full length circles but only the extension products derived from the truncated version can reassociate to the truncated circle. Thus, there is a chance that a full length circle would reassociate to two extension products (one derived from the full length template and another derived from the truncated version). If that happens the truncated template will not have any extension product to reassociate with and therefore will be present in the normalized library. Applicants will discuss the utilization of a different primer to prime 1st strand cDNA synthesis which will help to minimize this problem.

c) Another important item to discuss is the fact that the frequency of repetitive sequences does not go down with normalization. This was also observed by the other groups and it is a very fortune fact. It would be undesirable if the frequency would go down because that would indicate that rare cDNAs that happened to have a repeat in their 3' non coding region could potentially be eliminated with normalization. Thus, it is an advantage that applicants do not see that happen. The reason why that does not happen is because double strand DNA will only bind to HAP if it is at least 100 bp long and if does not have mismatches. In other words, it takes about 100 bp of a perfect duplex to bind to HAP under applicants' conditions. Repetitive sequences are grouped into families and the sequence divergence among their members is high enough so that the hybrids that are formed upon reassociation will be imperfect and therefore will escape binding to HAP.

d) In Ko's method, both coding and non coding fragments are present during reassociation. However, after the final digestion and directional cloning steps only the 3' non coding fragments remain in the normalized library. Ko's rationale for constructing a normalized library consisting exclusively of 3' non coding sequences was the following. The 3' non coding terminal exon of a mRNA is almost always unique to that transcript. Thus, during the reassociation step, each 3' non coding sequence is expected to only re-anneal to its very complementary strand. In contrast, coding exons may be conserved among members of a gene family, some of which might be less represented than others in a given tissue. Thus, during reassociation, the most frequent of such coding sequences is might cross-hybridize to a related, but divergent, complementary strand from a less prevalent family member, which could result in the elimination of the rarer family member from the normalized library.

Third Series of Experiments

The mRNAs of a typical somatic cell are distributed in three frequency classes (1,2) that are presumably maintained in representative cDNA libraries. The classes at the two extremes (ca 10% and 40–45% of the total, respectively) include members occurring at vastly different relative frequencies. On average, the most prevalent class consists of about 10 mRNA species, each represented by 5,000 copies per cell, whereas the class of high complexity comprises 15,000 different species each represented by 1–15 copies only. Rare mRNAs are even more under-represented in the brain, a tissue exhibiting an exceptionally high sequence complexity of transcripts (3–5).

Although even the rarest mRNA sequence from any tissue is likely to be represented in a cDNA library of $10^7$ recombinants, its identification is very difficult (its frequency of occurrence may be as low as $2\times10^{-6}$ on average or even $10^{-7}$ for complex tissues such as the brain). Thus, for a variety of purposes, it is advantageous to apply a normalization procedure and bring the frequency of each clone in a cDNA library within a narrow range (generation of a perfectly equimolar cDNA library is practically impossible in applicants' experience). Normalized cDNA libraries can facilitate positional cloning products aiming at the identification of disease genes, can increase the efficiency of subtractive hybridization procedures, and can facilitate significantly genomic research pursuing chromosomal assignment of expressed sequences and their localization in large fragments of cloned genomic DNA (exon mapping). It is notable that normalization makes feasible the gridding of cDNA libraries on filters at high density by reducing the number of clones to be arrayed (gridding $10^7$ clones for 1x coverage of a non-normalized library is not a feasible task). Finally, by increasing the frequency of occurrence of rare cDNA clones while decreasing simultaneously the percentage of abundant cDNAs, normalization can expedite significantly the development of expressed sequence databases by random sequencing of cDNAs.

Although cDNA library normalization could be achieved by saturation hybridization to genomic DNA (6), this approach is impractical, since it would be extremely difficult to provide saturating amounts of the rarer cDNA species to the hybridization reaction. The alternative is the use of reassociation kinetics: assuming that cDNA annealing follows second-order kinetics, rarer species will anneal less rapidly and the remaining single-stranded fraction of cDNA will become progressively normalized during the course of the reaction (6–8). As reported in this application, applicants have used this kinetic principle to develop a method for normalization of a directionally cloned cDNA library that has significant advantages over two previously reported similar procedures (7,8; see Results and Discussion).

MATERIALS AND METHODS cDNA Library Construction

Poly (A)+ RNA isolated from the entire brain of a female infant (72 days old) who died in consequence of spinal muscular atrophy, was used for construction of a cDNA library (IB) as described (9,10). As a primer for first-strand cDNA synthesis, applicants used the oligonucleotide 5' AACTGGAAGAATTC<u>GCGGCCGC</u>AGGAAT$_{18}$ 3' SEQ ID NO:48 that contains a Not I site (underlined). After ligation to Hind III adaptors, the cDNAs were digested with Not I and cloned directionally into the Hind III and Not I sites of a phagemid vector (L-BA) that applicants have constructed by modifying pEMBL-9(+) (11). L-BA carries an ampicillin-resistance gene, plasmid and filamentous page (f1) origins of replication, and cloning sites (5' Hind III-Bam HI-Not I-Eco RI 3'). Superinfection of bacteria with the helper phage M13K07 (12) converts duplex plasmids into single-stranded DNA circles containing message-like strands of the cDNA inserts.

Preparation of Single-stranded Library DNA

Plasmid DNA from the IB library was electroporated into DH5αF' bacteria, the culture was grown under ampicillin selection at 37° C. to an $A_{600}$=0.2, super-infected with a 20-fold excess of the helper phage M13K07, and harvested after 4 hours for preparation of single-stranded plasmids, as described (12). To eliminate contaminating double-stranded RF DNA, 20 µg of the preparation were digested with Pvu II (that cleaves only duplex DNA molecules), extracted with phenol and chloroform, diluted by addition of 2 ml of leading buffer [0.12M Na phosphate buffer (PB), pH 6.8, containing 10 mM EDTA and 1% SDS], and purified by hydroxyapatite (HAP) chromatography at 60° C., using a column pre-equilibrated with the same buffer (1 ml bed volume; 0.4 g HAP). After a 6 ml wash with loading buffer, this volume was combined with the flow-through fraction, and the sample was extracted twice with $H_2O$-saturated sec-butanol, once with dried sec-butanol, and once with $H_2O$-saturated ether (3 volumes per extraction). The sample was desalted by passage through a Nensorb column (DuPont NEN Products, Boston, Mass.), according to the manufacturer's specifications, concentrated by ethanol precipitation, and electrophoresed on a low-melting agarose gel, to remove helper phage DNA and any residual tRNA contaminant or RNA oligonucleotides (breakdown products from the RNaseA digestion used during purification). The region of the gel containing the single-stranded library wa excised and, after β-agarase (New England Biolab, Beverly, Mass.) digestion, the DNA was purified and ethanol precipitated.

cDNA Library Normalization

The IB cDNA library was normalized (see FIG. 1) in two consecutive rounds to derive the normalized libraries $^1$NIB and $^2$NIB, using the following procedure. To synthesize a partial second strand of about 200 nucleotides (nt) by limited extension, 9 pmoles of the oligonucleotide primer 5' GCCG-CAGGAAT$_{15}$3' were added to 4.5 pmoles of single-stranded IB library DNA in a 150 µl reaction containing 30 mM Tris-HCl, pH7.5, 50 mM NaCl, 15 mM MgCl$_2$, 1 mM DTT, 0.1 mM each of all four deoxynucleotide triphosphates (dNTPs), 2.5 mM each of three dideoxynucleotide triphosphates (ddATP, ddCTP and ddGTP), and a trace of [α-$^{32}$P] dCTP. The mixture was incubated for 5 minutes at 60° C. and for 15 minutes at 50° C., the temperature was lowered to 37° C., 75 units of Klenow enzyme (United States Biochemical, Cleveland, Ohio) were added and the concubation was continued for 30 minutes. The reaction was terminated by addition of EDTA (20 mM final concentration) extracted with phenol and chloroform, diluted with 2 ml HAP loading buffer containing 50 µg of sonicated and denatured salmon sperm DNA carrier, and chromatographed on HAP, as described above. After washing, the partial duplex circles bound to HAP were eluted from the column with 6 ml of 0.4M PB containing 10 mM EDTA and 1% SDS. The concentration of PB in the eluate was lowered to 0.12M by adding 14 ml of $H_2O$ containing 50 µg DNA carrier, and the chromatographic step was repeated. The final eluate was extracted and desalted as described above and the DNA was ethanol precipitated. The pellet (112 ng) was dissolved in 2.5 µl formamide and the sample was heated for 3 minutes at 80° C. under a drop of mineral oil to dissociate the DNA strands. For an annealing reaction, the volume was brought to 5 µl by adding 0.5 µl of 0.1M Tris-HCl, pH 7.5, containing 0.1M EDTA, 0.5 µl of 5M NaCl, 1 μl (5 μg) of oligo-(dT)$_{25-30}$, and 0.5 μl (0.5 μg) of the extension primer. The last two ingredients were added to block stretches of A residues [representing the initial poly(A) tails] and regions complementary to the oligonucleotide on the single-stranded DNA circles. The annealing mixture was incubated at 42° C., and a 0.5 μl aliquot was withdrawn at 13 hours (calculated Cot=5.5). The unhybridized single-stranded circles (normalized library) were separated from the reassociated partial duplexes by HAP chromatography, and then recovered from the flow-through fraction as described above. Since applicants, and others (13), have observed that the electroporation efficiency of partially repaired circular molecules is increased by about 100-fold in comparison with single-stranded circles, the normalized cDNA circles were converted to partial duplexes by primer extension using random hexamers and T7 DNA Polymerase (Sequenase Version II; United States Biochemical, Cleveland, Ohio), in a 10–20 μl reaction containing 1 mM each of the dNTPs. After addition of EDTA to 20 mM, phenol extraction, and ethanol precipitation, the cDNAs were redissolved into 10 mM Tris-HCl, pH 7.5, 1 mM EDTA, and electroporated into competent bacteria (DH10B; Gibco BRL, Caithersburg, Md.). To determine the number of transformants, 1 hour after the electroporation a 10 μl aliquot of the culture was plated on an LB agar plate containing 75 μg/ml ampicillin (extrapolation from these data indicated that a normalized library of 2.5×10$^6$ colonies was obtained). Supercoiled plasmid DNA was then prepared ($^1$NIB library) using a Qiagen Plasmid kit (Qiagen, Chatsworth, Cailf.). The same protocol was used for a second round of normalization (calculated Cot=2.5), to derive the $^2$NIB library (1.3×10$^7$ transformants) from a preparation of $^1$NIB single-stranded circles, except that the HAP-purification step after primer extension to synthesize short complementary strands was omitted.

Colony Hybridization

For screening, colonies were grown on duplicate nylon filters (GeneScreen plus; DuPont NEN Products, Boston, Mass.) that were processed as described (14), and hybridized at 42° C. in 50% formamide, 5×Denhardt's solution, 0.75M NaCl, 0.15M Tris-HCl, pH 7.5, 0.1M Na phosphate, 0.1% Na pyrophosphate, 2% SDS and 100 μg/ml sheared and denatured salmon sperm DNA. Radioactive probes were prepared by random primed synthesis (15,16) using the Prime-it II kit (Stratagene®, La Jolla, Calif.), according to the manufacturer's specifications.

DNA Sequencing

Double-stranded plasmid DNA templates were prepared using the Wizard Minpreps DNA Purification System (Promega, Madison, Wis.) and sequenced from both ends using the universal forward and reverse M13 fluorescent primers. Reactions were assembled on a Biomek 1000 workstation (Beckman, Brea, Calif.) then transferred to a thermocycler (Perkin Elmer Cetus, Norwalk, Conn.) for cycle sequencing.

Reaction products were analyzed using the automated ABI 370A DNA Sequencer (Applied Biosystems, Foster City, Calif.). Nucleic acid and protein database searches were performed at the NCBI server using the Blast algorithm (17).

EXPERIMENTAL RESULTS AND DISCUSSION

Experimental Strategy

To develop a normalization procedure, shown schematically in FIG. 1, and at the same time increase the utility of the normalized model cDNA library, applicants first constructed a high quality brain cDNA library (IB) that has the following features (10): the average size of a cDNA insert is 1.7 kb, often providing coding region information by sequencing from the 5' end; the length of the segment representing mRNA poly(A) tail is short, allowing an increase in the output of useful sequencing information from the 3' end; the frequency of non-recombinant clones is extremely low (0.1%); and chimeric cDNAs have not been encountered, after single-pass sequencing of over 2,000 clones (10,18). However, the latter analysis also demonstrated that 13% of the clones in the IB library lack poly(A) -tails, and were presumably derived from aberrant priming.

To preserve the length of the cDNAs, avoid differential loss of sequences, and alleviate a need for subcloning steps after normalization, applicants exclude from applicants' protocol the use of PCR and chose directional cloning into a phagemid vector. Such vectors have been previously used advantageously for cDNA library subtractions (13), although normalization was not attempted. This cloning regime provides readily single-strands that can be used both for annealing and for direct propagation in bacteria. In control experiments (not shown), applicants assessed the frequency of occurrence of abundant cDNAs (encoding α- and β-tubulin, elongation factor 1α, and myelin basic protein), and demonstrated that, at least by this criterion, the representation of clones in the starting library remained unchanged after conversion into single-stranded circles. Applicants also note that electrophoretic purification of the circles prior to use is necessary, to remove contaminating RNA oligonucleotides (see Materials and Methods), the presence of which would otherwise result in undesirable internal priming events during the first step of applicants' protocol.

In contrast with applicants' scheme, two other PCR-based normalization methods (7,8) necessitate the use of subcloning steps. In one of these approaches (7), sheared cDNAs (0.2–0.4 kb) were ligated to a linker-primer, amplified by PCR, normalized kinetically, reamplified, and finally cloned directionally in such a way that only 3' terminal sequences (almost exclusively 3' noncoding regions) are purposely preserved. The steps of the second scheme (8) were similar, except that the process started from cloned, randomly pried, and relatively short cDNAs, initially selected to minimize length-dependent differential PCR amplification. Thus, both coding and noncoding regions were represented in the final normalized library, but in pieces.

While maintaining length and representation of mRNA regions, applicants' protocol (FIG. 1) also addressed successfully the problem recognized in the first of the alternate approaches (7). It was considered that the 3' noncoding region is almost always unique to the transcript that it represents and is expected, therefore, to anneal only to its complement. In contrast, cross-hybridzation of coding regions belonging to unequally represented members of oligo- or multi-gene families could result in the elimination of rarer members from the population during the normalization process. This possibility is precluded in applicants' method, which begins with the synthesis from the 3' end of the cDNA, of a short complementary strand on the circular single-stranded cDNA template under controlled conditions, calibrated to yield strands with a narrow size distribution (200±20 nt). Since the average length of 3' noncoding regions in brain mRNAs is 750 nt (19), the vast majority of synthesized complementary strands participating in the annealing reaction should be devoid of coding region sequences. Applicants note, however, that after this partial extension step, purification of the products by HAP chromatography is necessary to eliminate single-strands of the IB library lacking A-tails that cannot participate in primed synthesis. Applicants also note that they repeat the chromatographic step to reduce the background to negligible levels, since after the first passage through the HAP column about 0.1% of pure single-strands bind non-specifically. However, during the second round of normalization to derive the $^2$NIB library, applicants omitted this step since applicants showed that 187 clones, which were picked randomly and sequenced from the $^1$NIB library (see below) all contained 3' poly(A) stretches. The remaining steps of applicants' procedure entail melting and re-annealing of the partial duplexes, followed by purification of unreassociated circles (normalized library) by HAP chromatography and electroporation into bacteria (FIG. 1).

Characterization of Normalized cDNA Libraries

To evaluate the extent of normalization achieved with applicants' method, applicants compared the IB, $^1$NIB and $^2$NIB libraries by colony hybridization. For this analysis, applicants used 28 cDNA probes chosen to represent various frequencies of occurrence within a wide range (at least four orders of magnitude; 4.6% to <0.0006% in the IB library (FIG. 5). However, an additional comparison of these results with independent theoretical estimates was necessary, to provide a further assessment of the degree of normalization, especially because the $^1$NIB library was derived after incubation to a relatively low Cot (5.5) during the re-annealing step of applicants' procedure. When relatively high Cot values were used in applicants' initial attempts to normalize the IB library, applicants obtained unsatisfactory results (high background) that applicants attribute to technical problems inherent to the procedure. Nevertheless, a re-evaluation of brain cDNA hybridization data (20; see Table 2) suggests that a relatively low Cot would suffice for applicants' purpose, to bring the frequency of each library clone within a narrow range.

TABLE 2

Estimates of Frequencies of Brain mRNAS

| (a) Component | (b) % | (c) $k_{pfo}$ (pure) | (d) Complexity (kb) | (e) Number of RNA Species |
|---|---|---|---|---|
| I | 16 | 10 | 96 | 36 |
| II | 46 | 0.165 | 5,800 | 2,150 |
| III | 38 | 0.0079 | 122,000 | 45,000 |

| (f) Frequency (%) per species | (g) $k_{ao}$ | (h) Component (%) at Cot 5.5 | (i) Final Frequency (%) per species |
|---|---|---|---|
| 0.44 | 6.15 | 0.7 | 0.02 |
| 0.02 | 0.10 | 44.2 | 0.02 |
| 0.0008 | 0.0048 | 55.1 | 0.0012 |

(a) The experimental data of pseudo-first order hybridization kinetics of cDNA tracer, which was synthesized from mouse brain poly(A)$^+$ polysomal mRNA and driven by its template (20), were solved by computer (unconstrained fit) into three kinetic components using the EXCESS function of a least squares curve-fitting program (21)
(b) The fraction of total occupied by each of the components is shown, after a minor correction (at completion, practically all of the tracer had reacted). These numbers (and all other numbers) in the table have been rounded.
(c) The computer-calculated pseudo-first order hybridization rate constant ($k_{pfo}$; M$^{-1}$sec$^{-1}$) for each component was divided by each of the values in (b), to derive $k_{pfo}$ (pure).
(d) The complexity (i.e. length of unique sequence) was calculated by considering the data from a calibration kinetic standard: cDNA synthesized from encephalomyocarditis virus RNA (complexity: 9.7 kb) that was driven by its template ($K_{pfo}$ pure: 99). Thus, each of the values in (d) is the ratio (99 × 9.7)/(c). The complexity calculated for the rarest component (III) matches closely the values obtained from additional kinetic experiments using cDNA enriched for infrequent sequences (22, 23) and also the data of saturation experiments with single-copy genomic DNA tracer (24, 25).

TABLE 2-continued

Estimates of Frequencies of Brain mRNAS (e) The number of different RNA species in each component was estimated from their complexities by assuming that the average size of brain mRNA is 2.7 kb (26). A conjecture (26) that rare brain mRNAs are longer than this value (hypothetically 5 kb on average) has not been supported yet by hard evidence.
(f) The initial average frequency of an individual mRNA species of each component in the entire population of mRNA molecules is the ratio of values (b)/(e).
(g) To assess the behavior of these kinetic components under the annealing conditions that we used for normalization (Cot: 5.5; length of complementary sequence in annealing strands: 0.2 kb), we first calculated the second order reassociation rate constant ($k_{so}$; M$^{-1}$sec$^{-1}$) for each component. For this calculation, we considered that the $k_{so}$ of a single and pure kinetic component with a complexity of 1 kb reacting at a fragment length of 0.2 kb is 590 (27, 28). Thus each $k_{so}$ value is 590/(d).
(h) To determine the percentage of the leftover of each component in the population at Cot 5.5, we first used the $k_{so}$ values in (g) to calculate the fraction remaining single-stranded, according to the equation C/Co = 1/1 + kCot, and then normalized the derived values to a total of 100%.
(i) The final average frequency of an individual mRNA species of each component is the ratio of values (h)/(e).

For applicants' calculations (Table 2), which should be regarded as rough but indicative estimates, applicants used a set of reliable hybridization data that are available only for mouse brain mRNAs (20), assuming that these measurements that these measurements should not differ significantly among mammals (in all cases examined, including humans, the average amount of RNA per brain cell and the number of cells per gram tissue are practically the same; see e.g. references 29,30). These calculations show that at Cot 5.5, of the three kinetic classes of mRNAs, the most abundant species are drastically diminished, while all frequencies are brought within the range of one order of magnitude [Table 2; compare columns (b) and (h), and (f) and (i)]. Applicants' experimental results (FIG. 5) show that the same range is achieved after a single round of normalization at this Cot (5.5). Thus, for all practical purposes, a single cycle is probably sufficient. Secondary normalization (calculated Cot=2.5) to derive the $^2$NIB library, although not resulting in a dramatic improvement, preserved the range of frequencies, while making the differences among individual sequences narrower overall (FIG. 5). It is noteworthy that 11 of the 28 probes used in this analysis were derived from clones that were randomly picked from the $^1$NIB library. The overall frequency fold variation was reduced from >7,667 (4.61<0.0006) in the IB library, to 133 (0.4/0.003) and 26 (0.1/0.01) in the $^1$NIB and $^2$NIB libraries, respectively. However, some unexplained anomalies were also observed for a small minority of clones, whose already reduced frequencies in the $^1$NIB library were somewhat increased in the $^2$NIB library (FIG. 5).

To provide a further indication that normalization was successful, applicants sequenced from both ends 187 cDNA clones that were randomly picked from the $^1$NIB library (Genbank accession numbers T09994-T10011, T10014-T10369). With the exception of 4 clones, which carried sequences corresponding to human mitochondrial 16S rRNA, all other cDNAs of this pool were unique, in agreement with the expectation for a normalized library. To further investigate the effect of the normalization procedure on the subset of mitochondrial 16S rRNA clones (1.4%, 1% and 0.4% in the IB, $^1$NIB and $^2$NIB libraries, respectively), applicants compared the sequences of a number of 16S rRNA clones isolated from both the IB and $^1$NIB libraries (kindly provides by M. Adams and J. Sikela). This analysis (not shown) revealed that the 16S rRNA clones isolated from $^1$NIB do not correspond to the predominant 16S rRNA species present in the IB library. Interestingly, in 17 of 19 16S rRNA clones sequenced from the IB library, the position of the A-track was the same as that present In the nature 16S rRNA. In contrast, all 8 clones sequenced from the $^1$NIB library represented truncated versions of the 16S rRNA, in which different lengths of the 3' terminal sequence were absent. Such truncated clones are under-represented in the IB library (2 of 19). Therefore, their frequency was increased by normalization, as expected, while the 16S rRNA clones of the most prevalent form were reduced. It is likely that the shorter clones represent bona fide copies of naturally occurring truncated 16S rRNA molecules (31–33; to be discussed elsewhere).

Database searches (both Blastn and Blastx; 17) revealed that of the 183 cDNAs examined, 152 (83%) were unknown (no hits), 15 (8.2%) correspond to known human sequences, 5 (2.7%) were novel but related to known human sequences, 4 (2.2%) were homologous to mammalian sequences, and 7 (3.8%) were homologous to known sequences from various non-mammalian organisms.

In contrast to these results, when 1633 randomly picked clones from the non-normalized IB library were sequences mostly (88%) from the 5' end, the percentage of unknown sequences was significantly lower than in applicants' case (63%), while about 30% of the clones were sequences twice or more (up to 50) times (10). Similar results were obtained by sequencing 493 random IB clones exclusively from the 3' end (18). It is notable that of the initially abundant cDNAs, which were sequenced multiple times in both of these studies, those encoding elongation factor-1α, α-tubulin, β-tubulin, myelin basic protein and γ-actin (corresponding to applicants' probes 1–4 and 7; FIG. 5) were absent from the pool of 187 clones that applicants examined. Moreover, only 15 of the unique 183 clones that applicants sequenced from the $^1$NIB library (8%) had been previously identified in the collection of the sequenced 1633 IB clones.

Applicants note that 18 of the unknown cDNAs that applicants sequences (10% of the total clones) carried Alu repetitive elements (6 at the 5' end; 11 at the 3' end; and 1 at both ends). Thus, as previously observed (8), the frequency of cDNAs containing Alu repeats is not reduced by normalization. This phenomenon can be attributed to sequence heterogeneity among Alu family members, which are abe to form imperfect hybrids that are probably non-bindable to HAP. However, this is not a disadvantageous property, since it prevents elimination of rare, Alu-carrying cDNAs from the population.

To assess whether the normalization procedure had skewed the distribution of lengths favoring shorter cDNA clone, Southern blots of released inserts from the IB, $^1$NIB and $^2$NIB plasmids were hybridized with several of the cDNA probes used in FIG. 5 individually. The results (not shown) demonstrated that the intensity of hybridization signals varied as expected, but the size of each hybridizing fragment remained the same.

After completion of this manuscript, a paper appeared (34) describing an alternate normalization procedure, in which a cDNA library was constructed following depletion of abundant mRNA species by sequential hybridization cycles to matrix-bound cDNA. However, this procedure does not seem to be more advantageous than ours, while its actual practical potential remains to be assessed, as the putative normalized library was not adequately characterized.

References of the Third Series of Experiments

1. Davidson, E. H. and Britten, R. J. (1979). Science 204:1052–1059.
2. Bishop, J. O., Morton, J. G., Rosbash, M. and Richardson, M. (1974). Nature 250:199–204.
3. Hahn, W. E. and Owens, G. P. (1988) in *The Molecular Biology of Neurological Disease*, ed. R. N. Rosenberg and A. E. Harding (Butterworths, London).
4. Kaplan, B. and Finch, C. (1982) in *Molecular Approaches to Neurobiology*, ed. I. Brown (Academic Press, New York).
5. Snider, B. J. and Morrison-Bogorad, M. (1992). Brain Res. Rev. 17:263–282.
6. Weissman, S. M. (1987). Mol. Biol. Med. 4:133–143.
7. Ko, M. S. H. (1990). Nucleic Acids Res. 18:5705–5711.
8. Patanjali, S. R., Parimoo, S. and Weissman, S. M. (1991). Proc. Natl. Acad. Sci. USA 88:1943–1947.
9. Scores, M. B. (1994) in *Automated DNA Sequencing and Analysis Techniques*, ed. J. Craig Venter (Academic Press, London).
10. Adams, M. D., Soares, M. B., Kerlavage, A. R., Fields, C. and Venter, J. C. (1993). Nature Genet. 4:373–380.
11. Dente, L., Cesareni, G. and Cortese, R. (1983). Nucleic Acids Res. 11:1645–1655.
12. Vieira, J. and Messing, J. (1987). Methods Enzymol. 153:3–11.
13. Rubenstein, J. L. R., Brice, A. E. J., Ciaranello, R. D., Denney, D., Porteus, M. H. and Usdin, T. B. (1990). Nucleic Acids Res. 18:4833–4842.
14. Grunstein, M. and Hogness, D. (1975). Proc. Natl. Acad. Sci. USA 72:3961–3965.
15. Feinberg, A. P. and Vogelstein, B. (1983). Anal. Biochem. 132:6–13.
16. Feinberg, A. P. and Vogelstein, B. (1984). Anal. Biochem. 137:266–267.
17. Altschul, S. F., Gish, W., Miller, W., Myers, E. W. and Lipman, D. J. (1990). J. Mol. Biol. 215:403–410.
18. Khan, A. S., Wilcox, A. S., Polymeropoulos, M. H., Hopkins, J. A., Stevens, T. J., Robinson, M., Orpana, A. K. and Sikela, J. M. (1992). Nature Genet. 2:180–185.
19. Hawkins, J. D. (1988). Nucleic Acids Res. 16:9893–9908.
20. Hahn, W. E., Van Ness, J. and Maxwell, I. H. (1978). Proc. Natl. Acad. Sci. USA 75:5544–5547.
21. Pearson, W. R., Davidson, E. H. and Britten, R. J. (1977). Nucleic Acids Res. 4:1727–1737.
22. Van Ness, J. and Hahn, W. E. (1982). Nucleic Acids Res. 10:8061–8077.
23. Chaudhari, N. and Hahn, W. E. (1983). Science 220:924–928.
24. Bantle, J. A. and Hahn, W. E. (1976). Cell 8:139–150.
25. Grouse, L. D., Schrier, B. K., Bennett, E. L., Rosenzweig, M. R. and Nelson, P. G. (1978). J. Neurochem. 30:191–203.
26. Milner, R. J. and Sutcliffe, J. G. (1983). Nucleic Acids Res. 11:5497–5520.
27. Galau, G. A., Britten, R. J. and Davidson, E. H. (1977). Proc. Natl. Acad. Sci. USA 74:1020–1023.
28. Welsh, J., Liu, J-P and Efstratiadis, A. (1990). Genet. Anal. Techn. Appl. 7:5–17.
29. Mandel, P., Rein, H., Harth-Edel, S. and Mardlel, R. (1964) in *Comparative Neurochemistry*, ed. D. Richter (A Pergamon Press Book, The Macmillan Company, New York).
30. Winick, M. (1968). Pediat. Res. 2:352–355.
31. Mazo, A. M., Minchenko, A. G., Avdonina, T. A., Gause, G. G. and Pusyriov, A. T. (1983). Mol. Biol. Rep. 9:155–161.
32. Baserga, S. J., Linnenbach, A. J., Malcolm., S., Ghosh, P., Malcolm, A. D. B., Takeshita, K., Forget, B. G. and Benz Jr., E. J. (1985). Gene 35:305–312.

33. Christianson, T. W. and Clayton, D. A. (1988). Mol. Cell. Biol. 8:4502–4509.
34. Sasaki, Y. F., Ayusawa, D. and Oishi, M. (1994). Nucleic Acids Res. 22:987–992.

Fourth Series of Experiments

Modifications of the Protocol

It is imperative that the size of the extension products be homogeneous and not longer thatn 200–350 nt so that synthesis remains restricted to the 3' non-coding region. Accordingly, applicants have introduced modifications in the original protocol.

a) the final concentration of dNTPs was increased from 0.1 mM up to 1 mM, and the fold excess of each dideoxynucleotide (ddATP, ddCTP and ddGTP) was decreased from 25 fold down to 6.25 fold. Therefore, applicants now use 1 mM each dNTP and 6.25 mM each ddATP, ddCTP and ddGTP. FIG. 6 shows the results of a titration experiment in which primer extension reactions were carried out with 1 mM dNTPs and increasing amounts (5.25 mM, 5.75 mM and 6.25 m) of each ddATP, ddCTP and ddGTP.

b) an oligo(dT)$_{12-18}$ was used as a primer to replace the 5' GGCCGCAGGAA(T)$_{15}$3' SEQ ID NO:49 oligonucleotide which was used for normalization of the infant brain library. The use of the oligo(dT)$_{12-18}$ primer is advantageous because it can be used for any oligo(dT)-primed library, regardless of the rare restriction site used for directional cloning.

c) applicants have tested whether a second cycle of the normalization procedure would result in an even better extent of normalization. Accordingly, applicants re-normalized the normalized infant brain library ($^1$NIB) to generate the $^2$NIB library. Although not indispensable, the second cycle did contribute to make the range of frequencies even narrower. Applicants have also adopted the same strategy to generate different normalized version of a fetal liver-spleen library (see below).

The higher reproducibility is probably due to the fact that these conditions (vase excess of dNTPs) make the procedure less sensitive to differences in template concentration, while the enzyme is working under optimal conditions.

In the reaction that was performed to generate the normalized liver-spleen library, approximately 1.5 pmoles of template and 3 pmoles of oligo(dT)$_{12-18}$ primer were present in a single 100 μl reaction containing 37.5 units of the Klenow fragment of DNA Polymerase I, 1 mM each dNTP, 6.25 mM each ddATP, ddCTP and ddGTP and a trace of α$^{32}$PdCTP. Incubation times and temperatures were precisely as described before.

Normalization of the Fetal Liver-Spleen Library

Two cycles of normalization were carried out. In the first cycle, single-stranded circles from the starting library were subjected to the normalization protocol. While the reassociation reaction was taking place, aliquots were withdrawn at $^1$Cot 0.5, $^1$Cot 5 and $^1$Cot 11.5, and after processing they were individually electroporated into bacteria to generate each a normalized library.

Preliminary characterization of each of the three normalized libraries by colony hybridization experiments with cDNA probes representing RNAs that occur at high frequencies in the starting library indicated that normalization was successful (see table below).

| cDNA Probe | Starting Library | $^1$Cot 0.5 | $^1$Cot 5 | $^1$Cot 11.5 |
|---|---|---|---|---|
| albumin | 10% | 1.3% | 1.05% | 0.7% |
| apolipoprotein | 2.3% | 0.2% | 0.04% | 0.03% |
| ferritin | 8.3% | 0.5% | 0.37% | 0.46% |

A second cycle of normalization was then performed as follows: single-stranded circles from the $^1$Cot 0.5 library was subjected to the normalization protocol and as before while reassociation was taking place aliquots were taken at $^2$Cot 0.5, $^2$Cot 5 and $^2$Cot 20. Each sample was then processed, thus generating three additional normalized libraries. The libraries obtained after this second cycle were evaluated by Southern hybridization with cDNA probes as follows: plasmid DNA from the starting library, $^1$Cot 0.5 library, as well as $^2$cot 0.5, $^2$Cot 5 ad $^2$Cot 20 libraries was doubly digested to release inserts from vector sequences, electrophoresed on agarose gels ad Southern transferred to nylon membranes. These filters were then hybridized with cDNA probes for ferritin, albumin and apolipoprotein (see FIG. 7). The results clearly indicated that the higher the Cot the lower the frequency of each of these three sequences in the respective resulting normalized library. Accordingly, the $^2$Cot 20 library was considered to be the best one.

It should be emphasized, however, that a very good extent of normalization had already been achieved after a single cycle of the protocol and that the performance of a second cycle should not be considered as mandatory but rather as something that contributes to narrow frequencies even further.

Fifth Series of Experiments

Applicants have developed a general method for en masse isolation of cDNAs present in a normalized library by hybridization to arrayed chromosome-specific phage λ clones; applicants have used this approach to initiate exonmapping chromosome 13. An advantage of the simultaneous isolation of cDNAλ pairs is that it allows cytogenetic assignment of a bona fide genomic clone by in situ hybridization which also verifies that the corresponding cDNA or a homologous expressed sequence resides on chromosome 13. This information is enriched by partial sequencing of a selected cDNA from both ends. The sequence of the 3' noncoding region provides an "identifier" that is used to develop STSs, while the sequence from the 5' end, often corresponding to a coding region, is used for homology searches in databases that occasionally reveal gene functions.

Cloned genomic DNA fragments of large size are currently used to assemble long-range contigs for physical mapping of the human genome. The utility of such molecular physical maps of human chromosomes for the identification of genes related to hereditary disorders and also for future sequencing projects, can be significantly enhanced by localization of expressed regions residing in large DNA fragments (cDNA or exon mapping). To meet this goal, several strategies have been developed [1] with various advantages and disadvantages (see Discussion).

In some of these approaches, cDNAs are selected efficiently by hybridization to cloned genomic DNA. However, when this hybridization principle is used for exon mapping, it is important to consider that a cDNA does not always correspond to a unique gene, but it may represent a member of an oligogene or multigene family. Thus, quite often a cDNA may be selected by cross-hybridization to a homologous but not identical, segment of a genomic fragment. As applicants report here, applicants have used human chromosome 13 (Chr13) as a model system for exon mapping, and developed a method for cDNA selection which, among other advantages provides an adequate solution to this problem through the simultaneous isolation of hybridization pairs of cDNAs and phage λ Chr13 genomic clones. The criterion of specificity in chromosomal assignment is fulfilled by cytogenetic mapping of the genomic clone, while the identity or sequence homology of the cognate cDNA is tested by Southern and PCR analyses.

MATERIALS AND METHODS

Somatic Cell Hybrids

As a source of human chromosome 13 DNA, applicants used the hamster(CH)-human hybrid cell line GM 10898 containing human chromosome 12 as its only human chromosome. This line was developed by J. Wasmuth and is available from the National Institutes of General Medical Sciences Human Mutant Cell Repository (Camden, N.J.). For in situ hybridization, applicants also used the CHO-human hybrid PK87-6.13, developed by D. Warburton, which contains only human chromosomes 6 and 13.

Human chromosome 13 Phage λ library

This 31X redundant library of mostly chromosome 13-specific genomic clones (LA13NL01), which carry DNA inserts of 15–20 kb generated by partial Sau 3A digestion, was constructed into λ Charon 40 from flow sorted chromosomes from a hamster-human cell hybrid (HHW686) containing human chromosomes 13, der 5. The recovered chromosome 13 DNA (92% pure) was contaminated with DNA from chromosome 5. It has been estimated that of the clones of this library, 92% contain human and 4% rodent DNA, while the background of nonrecombinants is low (4%).

For application of applicants' procedure, 360 phage plaques were picked, spotted onto a lawn of LE392 cells (100–200 plaques per 137 mm plate), and then transferred [42] to nylon filters (GeneScreen Plus; NEN). Since each clone has its own address in these arrays, rescreening for plaque purification is unnecessary.

cDNA library

In applicants' selection procedure, applicants used a human infant brain (IB) cDNA library that was constructed into phagemid vectors by directional cloning, as described [43,44], and then normalized (1NIB library; [40]).

Preparation of Double-and Single-stranded cDNA Plasmids

To convert double-stranded phagemids of the cDNA library into single-stranded circles, applicants used the DH5αF host stain. For this purpose, duplex plasmids were electroporated into HD5λF and propagated under ampicillin selection. The culture was grown at 37° C. to an A600=0.2, super-infected with a 20-fold excess of the helper phage R408, and harvested after 4 hr for preparation of singly-stranded plasmids, as described [45]. When the library or individual cDNAs were propagated as duplex plasmids, applicants used a different bacterial host (DH10B; Gibco-BRL®).

To prepare either DH5αF or DH10B bacteria competent for electroporation with efficiencies of 3×109 or 3×1010 cfu/µg of supercoiled pUC19 plasmid DNA, respectively, applicants used the following protocol. After growing a singly colony overnight at 37° C. in 100 ml 2XYT broth containing 15 µg/ml nalidixic acid (DH5αF) or 25 µg/ml streptomycin (DH10B), 10 ml of this culture were inoculated in 1 liter of 2XYT and grown to A600=0.2–0.25. The culture was then chilled on ice and distributed into six polypropylene conical bottles (200 ml; Nunc) that were centrifuged for 10 min at 10,000 rpm in a GSA rotor (Sorvall RC-5B). Each bacterial pellet was resuspended gently into 50 ml of ice-cold 10% glycerol and the suspensions were combined into two bottles that were centrifuged as above. This step of resuspension/centrifugation was repeated twice, first using 100 ml of 10% glycerol and then 50 ml per pellet. The suspensions were then combined into a single bottle that was centrifuged for 20 min at 10,000 rpm, and the final pellet was resuspended in 1–2 ml of ice-cold 10% glycerol. At this step, when a 25 µl aliquot is diluted into 10 ml of 10% glycerol, the A600 should be 0.15. The final suspension was then divided into 24 µl aliquots that were quickly-frozen in dyr ice-ethanol and stored at −70° C. Electroporations were performed under standard conditions (25 µF, 200 ohm) using a BioRad GenePulser and Pulse Controller [46].

cDNA Selection Protocol (FIG. 8)

Filters with arrayed chromosome 13 phage plaques were prehybridized in 50% formamide, 5×Denhardt's solution, 0.75M NaCl, 0.15M Tris-HCl pH 7.5, 0.1M Na phosphate, 0.1% Na Pyprophosphate, 2% SDS, and 100 µg/ml sheared and denatured salmon sperm DNA, for 1 hr at 42° C. After addition of 20 µg/ml poly (dl) -poly (dC) (Pharmacia®) and 15 µg/ml denatured human Cot1 DNA (75–200 nt fragments; Gibco-BRL®) to the prehybridization solution, the incubation was continued for 13 hr. The filters were washed twice at room temperature with a solution containing 0.3M NaCl, 0.04M Na phosphate pH 7.2, 2 mM EDTA, and 0.1% SDS, to remove the excess of poly(dl)-poly(dC), and then hybridized for 40–144 h at 42° C. with 50–100 µg of single-stranded cDNA plasmids (representing the entire IB or ¹NIB library) in 20 mls of the same (formamide-containing) solution as that used for prehybridization. To block hybridization between repeats, the single-stranded circles had already been pre-annealed with 1 mg of denatured human Cot 1 DNA for 30 min at 42° C. in 1–2 ml of a solution containing 50% formamide, 0.75M NaCl, 0.15M Tris pH 7.5, 0.1M Na phosphate, and 0.1% Na pyprophosphate. After hybridization, the filters were washed sequentially with 2×SC (0.3M NaCl, 30 mM Na citrate pH 7.0) containing 2% SDS for 30 mins at room temperature, with 2×SSC/2% SDS/50% formamide for 30 min at 42° C., and finally with 0.1×SSC/0.5% SDS for 15 min at 65° C. (prolonged incubation in aqueous solution at 65° C. was avoided, to minimize nicking of the circular single-stranded phagemid molecules).

To visualize cDNA/λ hybrids, the filters were subsequently hybridized with a 32P-labeled phagemid vector probe. Thus, after detection of positive signal, the position of a λ clone that was hybridized with a cDNA was identified in the array, and the corresponding phage was purified from the plaque of the initial plate by standard procedures [42]. To recover the cognate cDNA by alkaline denaturation and elution, a small piece of the filter containing the positive cDNA/λpair was cut out and placed into a 1.5 ml Eppendorf tube containing 100 µl of sonicated salmon sperm DNA carrier, 30 µl of 3 Na acetate pH 5.2, and 170 µl of $H_2O$ to each tube, the DNA was precipitated with 2.5 volumes of ethanol, Recovered cDNAs were then converted to partial double-stranded circles by primer extension, using either M13 universal primer or random hexamers and T7 DNA Polymerase (Sequenase Version II; USB), in a 10–20 µl reaction containing 1 mM each of the dNTPs. After extraction with phenol and chloroform and ethanol precipitation, phagemid cDNAs were electroporated into bacteria (DH10B) and propagated under ampicillin selection.

Validation of the Specificity of Selection

In contrast to highly repetitive sequences, low copy number repeats are not in general blocked efficiently by pre-annealing of the single-stranded cDNA library with an excess of human Cot 1 DNA. Thus, to verify that the selection of cDNA was specific, and not due to hybridization between a repetitive DNA element present on both the cDNA and a genomic clone, applicants applied routinely the following procedure.

After transformation of each selected cDNA, duplex plasmid DNA was prepared from 10 randomly picked colonies, digested with Not I and Hind III to release the inserts, and electrophoresed on a 1% agarose gel. Following alkaline transfer of the DNA onto a nylon membrane, as described [47], each blot was first hybridized with a 32P-labeled human Cot 1 DNA probe. It is applicants' experience that repetitive sequences present per haploid genome at a frequency as low as 1,000 copies are sufficiently in this Cot 1 DNA probe to allow detection of potential complements on cDNA after an overnight exposure. This is exemplified by cDNA20 (see Results), which corresponds to a human endogenous retrovirus-like element. The blot was then stripped of Cot 1 DNA probe by denaturation with 0.4N NaOH for 30 min at 42°0 C., and rehybridized with a probe synthesized from the entire corresponding λ genomic clone, including the phage DNA arms (the phagemid and λ genomic clone, including the phage DNA arms (the phagemid and λ vectors do not cross-hybridize).

The cDNAs hybridizing to their corresponding λ clones but not to human Cot 1 DNA were selected, and their authenticity as belonging to chromosome 13 was determined by Southern and PCR analyses (see below). After this step, each selected cDNA was positioned to a cytogenetic band of CHR13 by in situ hybridization (see below) using as probes the corresponding λ clones.

DNA and RNA analyses

DNA from the chromosome 13-containing GM10898 somatic cell hybrid and control DNA samples from the hamster CHO line UV 135 and from human placenta were digested with Hind III, electrophoresed on a 1% agarose gel and transferred to a nylon membrane. The inclusion of DNA from this entire panel is important, since a small percentage of clones in the genomic library were derived from human chromosome 5. Hybridizations were performed under the conditions described above for cDNA selection, using each time as a probe a candidate cDNA that was labeled by randomly primed synthesis [48,49] using the Prime-It II kit (Stratagene®) according to the manufacturer's instructions.

For Northern analysis, total cellular (20 μg per lane) or polyA+ (55 μg per lane) RNA from human infant brain and fetal liver and spleen were electrophoresed on formaldehyde/1% agarose gels [50] and then transferred onto nylon membranes. These blots were prehybridized and hybridized as described above.

DNA Sequencing

Double-stranded plasmid DNA was purified using Qiagen or Promega Magic Miniprep DNA Purification Systems and sequenced from both ends on an ANI 370A Sequencer using the universal forward and reverse M13 fluorescent primers. Reactions were assembled on a Biomek 1000 workstation and then transferred to a Perkin Elmer Cetrus thermocycler for cycle sequencing. Reaction products were analyzed using the automated AB1 370A DNA Sequencer. Nucleic acid and protein database searches were performed at the NCBI server using the Blast algorithm [51].

Chromosomal Assignment by PCR

For PCR analyses, oligonucleotide primer pairs (each with a calculated Tm between 59° C. and 61° C.; Table 4) were chosen from the 3' (and/or exceptionally the 5') terminal 300 nt of each cDNA (and/or exceptionally the genomic clone; see Table 4) using the Primer program (version 0.5; Whitehead Institute, 1991). The primers were synthesized on an ABI DNA synthesizer. PCR amplifications were performed in a Perkin Elmer Cetus Thermocycler model 480 with the GeneAmp PCR reagent kit (Perkin Elmer Cetus) in the presence of tracer α-32P-dCTP. Each reaction (100 μl) contained 10 mM Tris-HCl, pH 8.3, 2.5 mM MgCl2, 50 mM KCl, 0.2 mM each of the dNTPs, 0.2 μM each primer, 50 ng DNA template and 2.5 units of Taq Polymerase. The reaction mixtures were heated to 94° C. for 3 min, and then subjected to 30 cycles of melting (1 min at 94° C.), annealing (I min at 55° C.) and elongation (i min at 72° C. or exceptionally 2–5 min for longer fragments). The final extension was for 7 min at 72° C. DNA samples from the GM 10898 hybrid, CHO cells and human placenta were used as templates. In addition, reverse transcription-PCR (RT-PCR) was used to derive products from human infant brain total cellular RNA (pre-digested with RNAse free-DNaseI). The amplification products were denatured and electrophoresed, in parallel with size markers (end-labelled Msp I fragments of pBR322 DNA) on a 5% polyacrylamide sequencing gel. For autoradiography, each gel was exposed overnight at –70° C. with an intensifying screen.

In Situ Hybridization

To prepare probes for in situ hybridization, each phage λ clone corresponding to a cDNA was labeled by nick translation with digoxigenia-dUTP. Probes (10 ng/μl) were hybridized, as described [52] to metaphase spreads from the PK87-6.13 CHO-human cell line and to normal human metaphase preparations from lymphocyte cultures. Hybridized probe was detected by a nonfluorescent method, using sequentially peroxidase-tagged anti-digosigenin (Boehringer-Mannheim), DAB (diaminobenzidine) and silver amplification (Amersham kit), as described [52–55]. To determine the minimal silver amplification time sufficient to observe a specific signal, several times (ranging from 15 to 45 min) were tested with each probe. CElls were chosen for analysis only if the silver signal on chromosome 13 was confined to a single small dot on each chromatid. For each of the examined probes, 5–10 clearly labeled chromosomes were photographed and the correspondence of signal to a cytogenetic band on the long arm of the chromosome (13q) was assigned as follows. The distance from signal to telomere was divided by the total length of 13q, and this ratio was compared to the standardized ratios of cytogenetic bands that had been calculated similarly from a series of measurements on banded chromosome 13 specimens. This method permitted band assignments only to the level of resolution of a 400 band karyotype. Because of lower background, it was easier to detect specific signal using the metaphase spreads from the cell hybrids, but all locations were confirmed on normal human metaphase chromosomes.

EXPERIMENTAL RESULTS

Selection of cDNAs Using Chromosome 13-specific Phage λ Clones

Applicants' protocol for assignment of cDNAs to chromosomes, as applied to human Chr13, is outlined in FIG. 8. Phage λ clones from a Chr13-specific genomic library, immobilized on filters in arrayed configuration, are used as a hybridization reagent to select cDNAs from a (preferably normalized) library in the form of single-stranded circles. Construction of cDNA libraries in phagemid vectors allows easy conversion into single-strands, which facilitates both the normalization and selection procedures.

After the first hybridization step, the filter is rehybridized with a phagemid vector probe to visualize cDNA/λ pairs. Each member of a pair is then isolated. The λclone, which had an unique address on the master plate, is picked and propagated directly, obviating a need for plaque purification. The hybridized cDNA circles are eluted from the filter and converted into partial duplexes, since we, and others [2], have observed that the electroporation efficiency of partially duplex molecules is increased by about 100-fold, in comparison with that of single-strands. Despite this need for a primer extension reaction, the initial use of single-stranded circles that contain large size cDNA inserts and can be propagated in bacteria without intermediate subcloning steps is very advantageous.

Verification of Selection

As a single step to test the specificity of selection, released inserts from 10 randomly picked colonies derived from a single cDNA/λ pair, in each case, are analyzed by Southern blotting, using sequentially a repetitive genomic DNA probe (human Cot I DNA, BRL®) and a probe synthesized from the cognate λ clone (see Materials and Methods). Applicants consider the use of repetitive probe as an important requirement for quality control, although in the sample of clones reported here hybridization via repetitive elements was encountered only once (cDNA20; see below). However, the sensitivity an: specificity of the method was demonstrated by hybridization with phage probes. Although some of the clones were shown to be fortuitous hybridizers, applicants never failed to identity at least one true positive cDNA in each group of ten (a few cases). Most of the time half of the clones, and occasionally 9 of 10 cDNAs, were hybridized specifically to the λ probe. However, fulfillment of this criterion does not provide a guarantee that a cDNA sequence is CHR13-related, since the phage library includes a small fraction of chromosome 5 contaminants and clones of hamster DNA origin. For example, in situ hybridization analysis showed that sequences corresponding to a particular cDNA were located on chromosome 5 (cDNA22; data not shown). In another case, a false-positive α-tubulin cDNA (cDNA10; data not shown) was identified by cross-hybridization to a λ clone of CHO DNA, presumably containing an α-tubulin gene, that carried CHO-specific repeats, since it hybridized to all hamster chromosomes, according to the results of in situ hybridization analysis (not shown). As illustrated by these examples, further verification of cDNA authenticity is necessary, which can be achieved by using three methods (see also Materials and Methods).

First, Southern analysis with a particular cDNA probe, using in parallel Hind III-digested DNA isolated from human placenta, CHO cells and the GM10898 cell hybrid (chromosome 13 DNA in CHO background), allows on occasion assignment of the cDNA to chromosome 13. However, this is not always feasible, because of evolutionary conservation of some human and CHO expressed sequences and/or detection of multiple hybridizing fragments. Nevertheless, the 3' noncoding sequences of mRNAs are not as well conserved as the coding regions between species. Thus, in a second approach, which can provide better discrimination, the same three types of DNA are used a templates for pCR amplification with primers designed from the 3' terminal regions of the cDNAs (see Materials and Methods and Table 3). However, even the results of such PCR analyses are not always conclusive if members of multigene families are encountered. Thus, unequivocal assignment of selected cDNAs to CHR13, and simultaneous regional localization, is achieved by in situ hybridization. This is best achieved by using the cognate λ clone as a probe, rather than the cDNA itself, for two reasons. The longer phage probe provides a better signal, while the evolutionarily divergent intronic and intergenic sequences, which predominate in the λ inserts, allow a high degree of discrimination.

TABLE 3

Chromosome 13 Gene based STSs (A) cDNAS of Known Identity

| cDNA Name | Identification | Genbank Number | GDB Name | cDNA Length | Poly(A) signal (kb) |
|---|---|---|---|---|---|
| cDNA6 | High Mobility Group 1-Protein | L13804 L1380S | HMG1L | 0.6 | AAUACA |
| cDNA7A | α-Tubulin | L13808 L13809 | TUBA2 | 1.5 | AAUAAA |
| cDNA7B | α-Tubulin | L13810 L13811 | TUBA2 | 1.5 | AGUAAA |
| cDNA11 | Elongation Factor 1-α | L13814 L13815 | EEF1AL | 1.6 | AUUAAA |
| cDNA12 | Glyceraldehye 3P-Dehydrogenase | L13816 L13817 | GAPDL14 | 1.5 | AAUAAA |
| cDNA20 | Human Endogenous Retrovirus RTVLH2 | L13822 L13823 | D13F119S1E, D | 1.75 | AGUAAA |
| cDNA21A | Putative Protein Kinase | L13824 L13825 | | 1.5 | AAUAAA |
| cDNA21B | Putative Protein Kinase | L13826 L13208 | D13S502E | 1.8 | AAUAAA |

(A) cDNAS of Known Identity

| CH13 Hind III Fragments (kb) | Human Hind III Fragments (kb) | CHO Hind III Fragments (kb) | Brain mRNA (kb) | Genomic clone | Cytogenetic Band |
|---|---|---|---|---|---|
| multiple | multiple | multiple | 2.3, 0.9, 0.4, 3.4 | 13-λ6 | q12 |
| multiple | multiple | multiple | 1.7 | 13-λ7 | q11 |
| multiple | multiple | multiple | 1.7 | 13-λ7 | q11 |
| multiple | multiple | multiple | 1.8 | 13-λ11 | q21 |
| multiple | multiple | multiple | 1.7 | 13-λ12 | q11–q12 |
| multiple | multiple | none detectable | not determined | 13-λ20 | q14 & q33 |
| 3.0 | 4.0, 3.0, 9.0 (weak) | 5.5 | not detectable | 13-λ21 | q12 |

TABLE 3-continued

Chromosome 13 Gene based STSs

| | | | | | |
|---|---|---|---|---|---|
| 9.0, 3.0 | 4.0, 3.0, 9.0 | 5.5 | not detectable | 13-λ21 | q12 |

(B) Novel cDNAs

| cDNA Name | Identification | Genbank Number | GDB Name | cDNA Length | Poly(A) signal (kb) |
|---|---|---|---|---|---|
| cDNA8 | Unknown | L13812 L13813 | D13S509E | 1.4 | AAUAA |
| cDNA17A | Unknown | L13818 L13819 | | 1.5 | not present |
| cDNA17B | Unknown | L13820 L13821 | D13S501E | 2.25 | AAUAAA |
| cDNA19A | Unknown | L23206 L23207 | D135502E | 1.95 | not present |
| cDNA19B | Unknown | L23206 L30108 | | 1.6 | not present |
| cDNA23A | Unknown | L13828 L13829 | D13S504E | 1.1 | not present |
| cDNA23B | Unknown | L13830 L13831 | D13S505E | 1.55 | AAUAA |
| cDNA25 | Unknown | L13832 L13833 | D13S506E | 1.3 | UAUAA |
| cDNA26A | Unknown | L13834 L13835 | | 1.3 | AAUAAA |
| cDNA26B | Unknown | L13836 L13837 | D13S507E | 2.0 | AAUAAA |

(B) Novel cDNAs

| CH13 Hind III Fragments (kb) | Human Hind III Fragments (kb) | CHO Hind III Fragments (kb) | Brain mRNA (kb) | Genomic clone | Cytogenetic Band |
|---|---|---|---|---|---|
| 6.5, 3.5 | 6.5, 3.5 | none detectable | not detectable | 13-λ8 | q32 |
| 8.2, 4.2 (weak) | 8.2, 4.1 (weak) | multiple | not detectable | 13-λ17 | q33 |
| 8.2 | 8.2, 5.5 | 6.0 | not detectable | 13-λ17 | q33 |
| 7.5 | 7.5 | none detectable | not detectable | 13-λ19 | q11 |
| | | | | 13-λ19 | q11 |
| 2.3 | 2.3 | none detectable | not detectable | 13-λ23 | q11 |
| 7.2, 5.2 | 7.2, 5.2 | none detectable | not detectable | 13-λ23 | q11 |
| 23.0 | 23.0 | none detectable | not detectable | 13-λ25 | q34 |
| 25.0 | 25.0 | none detectable | not detectable | 13-λ26 | q13 |
| 25.0 | 25.0 | none detectable | not detectable | 13-λ26 | q13 | cDNAS 6, 7A, 7B, 8, 11, 12, 17A, 17B, 19A and 19B were selected from the Ib Library; the remaining cDNAS were selected from the [1]NIB library. With the exception of cDNAs 19A and 19B, all other cDNAs have an oligo-d(A) tract at their 3' end with the exception of cDNA 17A (see text) all other cDNAs have a bonafide polyadenylation signal sequence located 12–26 bp upstream from the tail. The Genbank accession numbers of both the 3' and 5' end sequences of each cDNA are listed. Whenever two cDNAs represented different incomplete products of reverse transcription of the same transcript (cDNAs 17A and 17B, cDNAs 19A and 19B; CDNAs 21A and 21B; cDNAs 26A and 26B), GDB D-segment numbers were obtained only for the longer cDNA in each case.

Using applicants' methods, applicants selected 18 cDNAs and their respective 12λ clones corresponding to 11 genes and a human endogenous retrovirus element (Table 3). The fact that two different cDNAs were selected by a single λ clone in six cases is indicative of the sensitivity of the method (see FIG. 9). Partial sequencing information was obtained from both the 5' and 3' ends of all cDNAs, and database searches revealed the identities, homologies or putative functions of 8 cDNAs (6λ clones). The sequences of the remaining 10 cDNAs (6λ clones) are novel.

Sequences of Known or Putative Function High Mobility Group-1 Protein

The homology search using the sequencing information from both the 5' and 3' terminal regions of cDNA6 showed that this brain sequence is identical to that carried by a placental cDNA clone encoding the high mobility group-1 (HMG1) nonhistone chromosomal protein [3]. As expected from the demonstrated evolutionary conservation of this sequence across species [3], the results of Southern analysis using a cDNA6 probe were inconclusive, since multiple common hybridizing Hind III fragments were observed in human DNA, GM 10898 hybrid DNA and CHO DNA. On the other hand, the PCR analysis was more informative, Primers derived from the 3' noncoding region of cDNA6 failed to amplify either GM 10898 hybrid or CHO DNAs, while a fragment of expected size was obtained both with human DNA and cDNA control (see Table 4). In contrast, when primers derived from the 5' end of cDNA6 (5' terminal sequence of the 3' noncoding region) were used, the PCR results were positive for all DNA templates tested (human DNA, GM 10898 hybrid DNA, CHO DNA, cDNA control, and DNA from the cognate 13-λ6 clone; Table 4). Applicants interpret these results as indicating that the genomic clone 13-λ6, which was regionally mapped to 13q12 by in situ hybridization, carries an (active or inactive) HMG1-related sequence. A high number of HMG1-like sequences, most of them representing retropseudogenes, are present in the human genome [4], but it is unknown whether more than one active gene exists. In this regard, it remains to be seen whether the several transcripts previously described [3,4], and also detected in brain with a cDNA6 probe (see Table 3), correspond to different gene products or are generated from a single precursor by differential RNA processing.

TABLE 4

Chromosome 13 Gene Based STSs

| STS Name | Size of PCR Product | | | |
|---|---|---|---|---|
| | Human | CH13 | CHO | CDNA |
| STS6-3 | 173 | — | — | 173 |
| 13-STS6-5 | 153 | 153 | 153 | 153 |
| 13-STS7 | 238 | 238 | — | — |
| 13-STS8 | 208 | 208 | — | 208 |
| 13-STS11 | 207 | 207 | — | 207 |
| STS12 | 188 | — | — | 188 |
| 13-STS17AB | 1236 | 1236 | — | 1236 |
| 13-STS19-5 | 327 | 327 | — | 327 |
| 13-STS21 | 153 | 153 | — | 153 |
| STS21 | 62 | — | — | 62 |
| 13-STS23A | 274 | 274 | — | 274 |
| 13-STS23B | 163 | 163 | — | 163 |
| 13-STS25 | 205 | 205 | — | 205 |
| 13-STS26A | 163 | 163 | — | 163 |
| 13-STS26B | 163 | 163 | — | 163 |

| | Primer | | |
|---|---|---|---|
| STS Name | Type | Sequence | Comments |
| STS6-3 | Sense | AAGCAGGTTCTTGTTGGTGC | (a) |
| | Antisense | AGAATGTCAACAAAACAGCTGC | |
| 13-STS6-5 | Sense | ACCCCCCTGTACACAACTCA | (b) |
| | Antisense | TGCAAAATACCACCAGGACA | |
| 13-STS7 | Sense | AAGGTGCAGCGGGCT | (c) |
| | Antisense | CTTCACCTTCTTCAGCCTCG | |
| 13-STS8 | Sense | CAGTACCCTCTCTCCATTTTCA | (d) |
| | Antisense | GACAGAGTATCCCCTTGAGGG | |
| 13-STS11 | Sense | CTGTTTGTTTCAATTGGCCA | (e) |
| | Antisense | AAATTCTGGGACAAATTTTTGG | |
| 13-STS12 | Sense | CCTCCAAGGAGTAAGACCCC | (f) |
| | Antisense | GGTACATGACAAGGTGCGG | |
| 13-STS17AB | Sense | TCCATGGGTAATCCGTTCAT | (g) |
| | Antisense | ACCCAACGCAGAAATAAACG | |
| 13-STS19-5 | Sense | TTTCTTCAGCAAGCCTCTTT | (i) |
| | Antisense | TTCCCCCCTTTTGAAAGC | |
| 13-STS21 | Sense | AAATATTTTCGTCCTGATTTTAAAGC | (j) |
| | Antisense | CCTCAAAAATTCTAAGGCTCTCC | |
| STS21 | Sense | TCTTAGAAGCCCACTTCCTACATC | (k) |
| | Antisense | TTTTGGGTAAGGGATTTGACA | |
| 13-STS23A | Sense | CCCAGTGCAGAAATCAGGAT | (l) |
| | Antisense | AAAATCAGAATCGCTTCCCA | |
| 13-STS23B | Sense | TCCTTCTCAAACTGCAAAAGG | (m) |
| | Antisense | GAGCTCCAAACTGAATGGGT | |
| 13-STS25 | Sense | CATTTGTTCCCACTGCCTTT | (n) |
| | Antisense | TTCTGCAAACCACAATATGTCA | |
| 13-STS26A | Sense | ACACCTTACAAAGTGCTGAGTAGG | (o) |
| | Antisense | TTAAAAACAGCAATTTCTAGCCATA | |
| 13-STS26B | Sense | ACACCTTACAAAGTGCTGAGTAGG | (p) |
| | Antisense | AAAAACAGCAATTTCTAGCCAAAT | |

(a) Primers (sense, SEQ ID NO: 50; antisense, SEQ ID NO: 51) were derived from the 3' terminal sequence of the 3' noncoding region of cDNA6. CHO-specific amplification products were also observed.

TABLE 4-continued

Chromosome 13 Gene Based STSs (b) Primers (sense, SEQ ID NO: 52; antisense, SEQ ID NO: 53) were derived from the 5' terminal sequence of the 3' noncoding region of cDNA6. PCR amplification of the genomic clone 13-γ6 with this primer pair resulted in amplification of the same 153 bp fragment.
(c) This primer pair (sense, SEQ ID NO: 54; antisense, SEQ ID NO: 55) derived from the carboxy terminal region of the testis-specific α-tubulin gene of 13-γ7, was designed to be specific for the TUBA2 gene by anchoring the 3' end of each primer on a base that is different in the other tubulin genes. Additional, presumably non-specific, amplification products were observed both in human and CHO. As expected, no detectable amplification product was obtained by RT-PCR of brain mRNA with this prime pair.
(d) Primers (sense, SEQ ID NO: 56; antisense, SEQ ID NO: 57) were derived from the 3' end sequence of cDNA8.
(e) Primers (sense, SEQ ID NO: 58; antisense, SEQ ID NO: 59) were derived from the 3' terminal sequence of the 3' noncoding region of cDNA11. CHO-specific amplification products were also observed.
(f) Primers (sense, SEQ ID NO: 60; antisense, SEQ ID NO: 61) were derived from the 3' terminal sequence of the 3' noncoding region of cDNA12. CHO-specific amplification products were also observed.
(g) The sense primer (SEQ ID NO: 62) was from the 3' end of cDNA17A; the antisense primer (SEQ ID NO: 63) was derived from the 5' end of cDNA17B.
(h) Primers (sense, SEQ ID NO: 64; antisense, SEQ ID NO: 65) were derived from the 5' end of cDNA19.
(i) Primers (sense, SEQ ID NO: 66; antisense, SEQ ID NO: 67) were derived from the 3' end of cDNA21B.
(j) Primers (sense, SEQ ID NO: 68; antisense, SEQ ID NO: 69) were derived from the 5' end sequence of cDNA21B. The 62 bp amplified fragment is interrupted by an intron in 13-γ21. Accordingly, ampiification of this size fragment would only be expected from a processed pseudogene or cDNA templates. Larger amplification products were observed in the PCR of the CH13 DNA template.
(k) Primers (sense, SEQ ID NO: 70; antisense, SEQ ID NO: 71) were derived from the 3' end sequence cDNA23A.
(l) Primers (sense, SEQ ID NO: 72; antisense, SEQ ID NO: 73) were derived from the 3' end sequence of cDNA23B.
(m) Primers (sense, SEQ ID NO: 74; antisense, SEQ ID NO: 75) were derived from the 3' end sequence of cDNA25
(n) Primers (sense, SEQ ID NO: 76; antisense, SEQ ID NO: 77) were derived from the 3' end sequence of cDNA26A.
(o) Primers (sense, SEQ ID NO: 78; antisense, SEQ ID NO: 79) were derived from the 3' end sequence of cDNA26B.
The lengths (in bp) of the pCR amplification products of human DNA (human), GM 10898 DNA (CH13) and CHO DNA (CHO) are compared to thcse obtained by RT-PCR of human infant brain RNA control (cDNA). Primer pairs were derived as specified. PCR and gel electrophoresis conditions were described in the Methods section. All chromosome 13 STS's have the "13" prefix in their STS name.

α-Tubulin

Two α-tubulin cDNAs (cDNA 7A and 7B; FIG. 9) were selected by the same genomic clone (13-λ7). Sequence comparisons revealed that the cDNAs 7A and 7B, which have common coding, but different 3' noncoding sequences, are identical to the previously described human α-tubulin cDNAs bα1 and kα1. respectively [5]. The bα1 sequence is fetal brain-specific, while kα1 appears in a variety of tissues [5]. The genomic structure of the kα1 gene has not been reported, while the organization of the bα1 gene [6] indicates that a portion of the coding sequence is included in the same exon with the 3' noncoding region. From this information, in conjunction with the complete dissimilarity of the kα1 (cDNA 7A) and bα1 (cDNA 7B) 3' noncoding regions, it can be inferred that an intron is interrupting the kα1 gene immediately after the termination codon.

In mammals, the highly conserved α-tubulins are encoded by some so the 15–20 members of a multi-gene gamily that includes retropseudogenes [7]. Thus, as expected, our Southern and PCR analyses were uninformative. To examine whether the genomic clone 13-λ7, which was cytogenetically assigned to 13q11, corresponds to a gene or to a processed pseudogene, applicants partially sequenced a fragment hybridizing to a cDNA 7A probe. Comparison of this sequence with other known human α-tubulin gene sequences (FIG. 10A–C) revealed a high degree of homology (96%) with the H2α human gene, which encodes a testis-specific isotype [8]. Thus, it is likely that the Chr13 α-tubulin sequence corresponds to an active gene, since all of the nucleotide differences from the H2α sequence are silent substitutions in the compared codons for the carboxy-terminal amino acids. The putative gene carried by the 13-λ7 clone was designated TUBA2. Sequence comparison of TUBA2 with the TUBA1 (Hα44) gene on human chromosome 2q[9], which also encodes a testis-specific α-tubulin [10], showed a divergence of 15.5%. Some of the nucleotide substitutions correspond to amino acid replacements (FIG. 10A–C).

Elongation Factor-1α

The partial sequence that applicants obtained from cDNA11 (both 5' and 3') was identical to that encoding elongation factor-1α (EEF1A), a housekeeping protein involved in protein synthesis [11,12]. Southern analysis has shown that the human genome contains at least 20 loci with sequence homology to an EEF1A cDNA, but most of them correspond to retropseudogenes [13]. Thus far only one active gene has been described with certainty [12,13]. Not unexpectedly, due to multiple sequences and evolutionary conservation, applicants were unable to verify applicants' assignment by Southern analysis using a cDNA11 probe (multiple hybridizing Hind III fragments were observed with all DNA sources). On the other hand, when PCR was used with primers derived from the 3' end of cDNA11, a fragment of expected size was amplified from human DNA, GM 10898 hybrid DNA and cDNA control, while no amplification of CHO sequences was observed (Table 4). However, since applicants have not sequenced yet the genomic clone 13-λ11, it remains unknown whether the EEF1A locus, positioned to 13q21 by in situ hybridization, is the active gene or a processed pseudogene.

Glyceraldehyde-3-Phosphate Dehydrogenase

The sequence of cDNA 12 was identical to that encoding the evolutionarily conserved glyceraldehyde-3-phosphate dehydrogenase (GAPD), a glycolytic enzyme apparently acting as a tetramer [14–16]. The 37 kD subunit of GAPD also functions as a nuclear uracil DNA glyocyclase [17]. In human DNA, up to approximately 40 sequences cross-hybridize at high-stringency with a GAPD cDNA probe [18]. The existing evidence indicates that this family includes a single expressed locus that has been mapped to 12p13, while the remaining sequences, presumably representing retropseudogenes, are dispersed on many other chromosomes, including CHR13, as shown by Southern analysis [19]. The latter (named GAPDL14) might correspond to the sequence carried by applicants' genomic clone 13-λ12, which was localized to 13q11-q12 by in situ hybridization. The conclusion that the GAPD-related sequence on CHR13 should be a processed pseudogene is consistent with the results of PCR analysis. No amplification of chromosome 13 or CHO sequences was observed with primers derived from the 3' sequence of cDNA12, while a fragment of expected size was amplified from human and cDNA control templates (Table 4).

Human endogenous retrovirus-like element

Sequence analysis of cDNA20 revealed that this clone carried a retroviral element that is represented by approximately 1,000 copies per human haploid genome [20]. Thus, this sequence should be relatively under-represented in Cot1 DNA, which may explain why the homologous cDNA was not competed out efficiently during the pre-annealing reaction. Applicants note that the frequency of cDNA20 in both the 1B and $^1$NIB cDNA libraries is low (0.02%). This may suggest that only a few of these elements are actively transcribed.

In situ hybridization analysis using both the 13-λ20 clone and cDNA20 as probes allowed localization of this sequence to 13q33. However, the cDNA probe revealed an additional copy (or copies) of this retroviral element on 13q14. In fact, the hybridization signal with the cDNA probe was stronger at 13q14 than at 13q33. Since exons are under-represented in genomic clones, the signal detected with the λ probe is likely to have resulted from hybridization involving introns and intergenic sequences that are apparently unique to 13q33. Interestingly, Southern analysis with the cDNA probe revealed multiple copies of this retroviral element, not only in total human DNA, but also in GM 10898 DNA (not shown). These date suggest that multiple copies of this retroviral element might be clustered at least at 13q14. As expected for a human-specific repetitive sequence, cross-hybridizing Hind III fragments were not detected in CHO DNA.

A putative protein kinase

A computer search using the composite sequence of cDNAs 21A and 21B, representing different incomplete products of reverse transcription, revealed an open reading frame of 176 amino acids with weak but convincing homology to a number of $Ca^{2+}$. Calmodulin-dependent protein kinases (FIG. 11A–B). The region of homology includes an Arg residue that is present at the carboxy terminus of the catalytic domain of most kinases [21].

Partial sequencing of the corresponding 13-λ21 genomic clone, positioned cytogenetically to 13q12, revealed sequence identity with the cDNAs and the presence of three introns in this region (FIG. 11A–B). the sequence of the first detectable intron (3' splice site) is very short (6 nucleotides) and corresponds to one end of the cloned genomic fragment. Southern analysis with a cDNA21B probe (which is longer than 21A) showed three hybridizing Hind III fragments in total human DNA, only two of which are present on chromosome 13. Thus, a related sequence is present on another chromosome, which corresponds to a processed pseudogene according to the results of PCR analysis (Table 4). When primers derived from the 3' end of cDNA21B were used for amplification, the product of expected size was derived from human DNA, GM 10898 hybrid DNA and cDNA control, while no amplification of rodent sequences was observed. However, when the same templates were used with primers from the exon sequences flanking the first detectable intron, product of the predicted size was obtained, not only with the cDNA control (as expected), but also with total human DNA. Thus, the non-13 copy of this sequence should be a retropseudogene.

Novel cDNAs cDNAs 17A and 17B

Only the second of these non-overlapping cDNAs, both selected by the genomic clone 13-λ17, contains a polyadenylation signal (see Table 3 and FIG. 9B). Sequencing of a 1.4 Xba I fragment from 13-λ17, which hybridized with both cDNA probes, revealed that during 1st strand synthesis priming of cDNA17A occurred at an internal A-rich cluster of the mRNA located upstream of the sequence represented by cDNA17B (FIG. 9B). This was certified by RT-PCR analysis using infant brain RNA template devoid of DNA contamination and primers from the 5' end of cDNA17B and the 3' end of cDNA 17A. An amplification product of predicted size was obtained from the reaction (Table 4). On the other hand, Northern analysis with both cDNA probes failed to produce a hybridization signal, suggesting that the corresponding mRNA(s) might be rare (Table 3).

Southern analysis with a 13cDNA17B probe showed that total human DNA contains two hybridizing Hind III fragments, only one of which is present on CHR13 (see Table 3). The latter fragment and an additional, also 13-specific, fragment were detected by cDNA17A probe. The results with CHO DNA were more complex. The cDNA17A probe exhibited cross-hybridization with multiple fragments, while only a single band was detected with the cDNA17B probe. A possible interpretation of these results is that the hamster genome contains, in addition to a conserved gene, several diverged genes and/or pseudogenes.

cDNAs 19A and 19B

These cDNAs, differing only in the length of 5' sequence, represent different incomplete products of reverse transcription. The presence of a Not 1 site and the 3' end, while a polyadenylation signal and a poly(A) tail are missing, indicates that the initial double-stranded cDNA product was cleaved at an internal Not 1 site prior to closing. Northern analysis with a cDNA19A probe filled to detect any hybridizing mRNA. However, the fragment of expected size was successfully amplified by RT-PCR with primers derived from the 5' end of cDNA19A (Table 4).

cDNAs 23A and 23B

Both of these non-overlapping cDNAs were hybridized to the same genomic clone (13-, which was positioned to 13q11 by in situ hybridization, while Southern analysis showed that the sequences carried by these cDNAs are specific, and not in hamster DNA. Thus, unless two closely linked genes reside on 13-λ23, the two cDNAs should represent different regions of the same mRNA, especially since only one of them (cDNA23B) has a polyadenylation signal. However, applicants were unable to show whether this is indeed the case, because the results of Northern analysis were negative [the transcripts) may be rare]. Nevertheless, RT-PCR assays using infant brain RNA with primers derived from the 3' regions of the cDNAs resulted in amplification products of the expected sizes (see Table 4).
cDNAs 26A and 26B These two cDNAs were selected by the same genomic clone λ26). They appear to be the products of differential polyadenylation, since the 3' noncoding region of 26A, which is longer in the 3' direction, contains two polyadenylation signals (FIG. 9). Otherwise the two sequences are identical, with the exception of two extra T nucleotides in cDNA26B, apparently representing a simple polymorphism; DNA sequence of the product derived by PCR amplification of GM10898 DNA with primers derived from the 3' region of cDNA26B was identical to that of cDNA26B (Table 4). Southern analysis with cDNAs 26A and 26B probes revealed the presence of a single hybridizing Hind III fragment in both human and GM 10898 DNAs, and no cross-hybridizing CHO fragments. In situ hybridization with 13λ26 positioned this locus to 13q13.
EXPERIMENTAL DISCUSSION One of the strategies that have been used for identification of transcribed sequences within large fragments of genomic GNS is the direct screening of cDNA libraries with YAC probes [22,23]. Although successful on occasion, this approach is of low sensitivity and has technical problems. The opposite scheme, i.e. the screening of chromosome-specific libraries with total cDNA probes [24,25], has similar limitations in sensitivity, due to high probe complexity. "Exon trapping" [26,27], and "exon amplification" [28] are elegant methods that take advantage of RNA splicing to capture expressed sequences from large regions of genomic DNA. The advantage of these methods is that they permit identification of exons regardless of their presence in cDNA libraries. However, since potential utilization of cryptic splice sites may lead to artifacts, validation of the identity of a tapped exon ultimately requires isolation of its corresponding cDNA. This unavoidable screening of libraries with individual trapped exon probes, makes the procedure laborious and time consuming. Searches for HpaII tiny fragments (HTF) islands [29–32], which are frequently located upstream of genes, is not a general or reliable method for comprehensive exon mapping; the correlation is not universal, while the distance between an HTF island and the first exon might be large, making this approach tedious and inefficient. Finally, the identification of evolutionarily conserved coding sequences by cross-species hybridization [22, 33–35] is neither a rapid nor a large-scale approach.

More advantageous are two similar hybrid-selection methods [36,37], In those protocols, PCR-amplified cDNA fragments are hybridized to YAC DNA immobilized on filters, and the selected cDNAs are eluted, amplified by PCR and cloned, thus generating a mini-library that is enriched for expressed sequences residing on the YAC DNA insert, Successful modifications of this technique have also been reported [38,39], in which cloned genomic DNAs is biotinylated and then hybridized in solution with amplifiable cDNAs. The genomic clones are attached cDNAs are captured on streptavidin-coated magnetic beads, and the cDNAs are eluted and amplified.

Applicants' methods uses the same principle, but offers significant advantages over the PCR-based hybrid-selection procedures. First, in contrast to the short (usually ≦500 bp), randomly-primed cDNA segments that must be further amplified and cloned, the cDNAs that applicants select carry long inserts (1.7 kb on average in the particular library that applicants have used), which can be directly propagated in bacteria. Moreover, when two (or more) randomly-primed cDNAs are selected by the same genomic fragment, it is difficult to assess without an extensive subsequent analysis whether they represent parts of the same mRNA, homologous members of a family, or entirely different genes. In contrast, applicants' selection of Not-oligo(dT)-primed, directionally cloned cDNAs facilitates their analysis, since the 3' noncoding region that they usually contain can serve as an mRNA identifier. This region is often unique, while cases of differential polyadenylation or splicing can be discriminated by sequencing or cross-hybridization, if more than one cDNA is captured. Nevertheless, some problems can arise on occasion from internal priming at A-rich stretches or from the rare occurrence of internal Not I sites (see Results, for examples of such cases).

An additional advantage of applicants' approach is the simultaneous isolation of cDNA/λ pairs. Of these two reagents, a λ clone is a superior probe for in situ hybridization analysis that provides a better signal because of length and also guarantees specificity in the cytogenetic assignment because of the uniqueness of introns and gene flanking sequences. At the same time, verification of the chromosomal assignment is achieved. The cDNA, on the other hand, can be readily sequenced from both ends for establishment of an STS from the 3' identifier and database searches using the 5' end sequence, often representing coding region, to identify candidate function. The latter is exemplified by applicants' identification of an mRNA that apparently encodes a novel protein kinase (see Results). In interesting cases, the availability of a cognate λ clone for a characterized cDNA allows the acquisition of further sequence information from relevant regions of the gene itself. For example, applicants identified a novel human gene presumably encoding a testis-specific α-tubulin isotype by partial sequencing of applicants' 13-λ7 clone.

It is notable that, if appropriate analyses are applied, the potential of chromosomal DNA, used as a recognition reagent, to capture both corresponding and related cDNAs becomes an advantageous feature of all hybridization-based cDNA selection methods, including ours. Thus, on occasion, new gene family members may be revealed corresponding to functional genes or processed pseudogenes or multitranscript families might be identified derived from differential pre-mRNA processing or use of alternate promoters.

The fact that only 11 genes were identified in a total of 360 1 clones screened by applicants' method should be regarded cautiously. this is so because applicants elected to pursue only those that exhibited strong hybridization signal with the vector probe. It remains to be determined, however, whether a larger number of genes could have been identified if applicants had eluted cDNA circles from all phage plaques irrespectively of the signal observed with the vector probe. Nonetheless, if taken at faith value, applicants' results could be interpreted as indicative that the method lacks sensitivity, Accordingly, applicants note that the fact that two different cDNAs were selected by single 1 clones in six cases, and that they could be identified among 10 randomly picked colonies in each case, suggest otherwise. Furthermore, cDNA20, for example, occurs at a frequency of 0.02% in the [1]NIB library, a frequency that is only six fold higher than that of the least frequent clone documented to date in this library [40]. Therefore, applicants conclude that applicants' method is sensitive for selection of cDNAs from normalized libraries. Applicants' results could also be interpreted as indicative that chromosome 13 might be gene-poor (see below), and/or that either or both cDNA and genomic libraries are not well representative of all brain mRNAs and chromosome 13 sequences, respectively.

Chromosome 13 represents 105 Mb or 3.5% of the human haploid genome, and it might contain 1,750 to 3,500 genes, of which only a minority have been identified [41]. This paper contributes 11 regionally localized genes/pseudogenes to be added to the previous list of 46 genes/pseudogenes known to reside on Chr13. Of these 46, 33 have been assigned cytogenetically to 13q and only one (RNR1) to 130. With out contribution, a preliminary examination of a total of 44 genes (or pseudogenes) that have been localized to cytogenetic bands on the long arm of CHR13 shows an apparently uneven distribution; 64% of the mapped genes were localized in two regions that are the most proximal and most distal to the centromere (q11–12 and q33–34). Together, these two regions represent only 35% of the total length of the long arm. In contrast, only 6% of the genes were mapped to q21–22, a region that comprises 24% of 13q. It remains to be seen whether this phenomenon is real or due to sampling, either because the number of mapped genes is still small or because some bias was introduced by skewed representation of Chr13 sequences in the phage and or cDNA libraries.

References for the Fifth Series of Experiments

1. Hochgeschwender, U. and Brennan, M. B. (1991) Identifying genes within the genome: new ways for finding the needle in a haystack. *BioEssays,* 13, 139–144.
2. Rubenstein, J. L. R., Brice, A. E. J., Ciaranello, R. D., Denney, D., Porteus, M. H. and Usdin, T. B. (1990) Subtractive hybridization system using single-stranded phagemids with directional inserts. *Nucleic Acids Res.,* I8, 4833–4842.
3. Wen, L., Huang, J-K., Johnson, B. H., and Reeck, G. R. (1989) A human placental cDNA clone that encodes nonhistone chromosomal protein HMG1. *Nucleic Acids, Res.,* 17, 1197–1214.
4. Stros, M. and Dixon, G. H. (1993) A retropseudogene for non-histone chromosomal protein HMG1. *Biochem. Biophys. Acta,* 1172, 231–235.
  Cowan, N. J., Dobner, P. R., Fuchs, E. V. and Cleveland, D. W. (1983) Expression of human α-tubulin genes; interspecies conservation of 3' untranslated regions. *Mol. Cell. Biol.,* 3, 1738–1745.
6. Hall, J. L. and Cowan, N. J. (1085) Structural features and restricted expression of a human α-tubulin gene. *Nucleic Acids Res.,* 13, 207–223.
7. Little, M. and Seehaus, T. (1988) Comparative analysis of tubulin sequences. *Comp. Biochem.,* 90, 655–670.
8. Villasante, A., Wang, D., Dobner, P., Dolph, P. Lewis, S. A. and Cowan, N. J. (1086) Six mouse α-tubulin mRNAs encode five distinct isotypes: testis-specific expression of two sister genes. *Mol. Cell, Biol.,* 6, 2409–2419.
9. Gerhard, D. S., Dobner, P. R. and Bruns, G. (1985) Testis Specific α-tubulin is on chromosome 2q. *Cytogenet. Cell Generlk* 40, 639–640.
10. Dobner, P. R., Kislauskis, E., Wentworth, B. M. and Villa-Komaroff, L. (1087) Alternative 5' exons either provide or deny an initiator methionine codon to the same α-tubulin coding region. *Nucleic Acids Res.,* 15, 199–218.
11. Brands, J. H. G. M., Maassen, J. A., Van Hemert, F. J. Amons, R. and Moeller, W. (1986) The primary structure of the α-subunit of the human elongation factor 1. Structural aspects of guanine nucleotide-binding sites. *Eur. J. Biochem.,* 155, 167–171.
12. Uetsuki, T., Naito, A., Nagata, S. and Kaziro, Y. (1089) Isolation and characterization of the human chromosomal gene for polypeptide elongation factor 1-α. *J Biol. Chem.,* 264, 5791–5798.
13. Madsen, H. O., Poulsen, K., Dahl, O. Clark, B. F. C. and Hjorth, J. P. (1990) Retropseudogenes constitute the major part of the human elongation factor 1-α gene family. *Nucleic Acids Res.,* 18, 1513–1516.
14. Arcari, P., Martinelli, R. and Salvatore, F. (1984) The complete sequence of a full length cDNA for human liver glyceraldehyde-3-phosphate dehydrogenase: evidence for multiple mRNA species. *Nucleic Acids Res.,* 12, 9179–9189.
15. Tokunaga, K., Nakamura, Y., Skata, K., Fujimori, K., Ohkubo, M., Sawada, K. and Sakiyama, S. (1987) Enhanced expression of glyceraldehyde-3-phosphate dehydrogenase gene in human lung cancers. *Cancer Res.,* 47, 5616–5619.
16. Ercolani, L., Florence, B., Denaro, M. and Alexander, M. (1988) Isolation and complete sequence of a functional human glyceraldehyde-3-phosphate dehydrogenase gene. *J. Biol. Chem.,* 263, 15335–15341.
17. Meyer-Siegler, K., Mauro, D. J., Seal, G. Wurzer, J. and DeRiel, J. K. (1001) A human nuclear uracil DNA glycosylase is the 37-kDa subunit of glyceraldehyde-3-phosphate dehydrogenase. *Proc. Natl. Acad. Sci. USA,* 88, 8460–8464.
18. Benham, F. J., Hodgkinson, S. and Davies, K. E. (1984) A glyceraldehyde-3-phosphate dehydrogenase pseudogene on the short arm of the human X chromosome defines a multigene family. *EMBO J.,* 3, 2635–2640.
19. Benham, F. J. and Povey, S. (1989) Members of the human glyceraldehyde-3-phosphate dehydrogenase-related gene family map to dispersed chromosomal locations. *Genomics,* 5, 209–214.
20. Mager, D. L. and Freeman, J. D. (1087) Human endogenous retroviruslike genome with type C pol sequences and gag sequences related to human T-cell lymphotropic viruses. *J. Virol.,* 61, 4060–4066.
21. Hanks, S. K., Wuinn, A. M. and Hunter, T. (1988) The protein kinase family: conserved features and deduced phylogeny of the catalytic domains. *Science,* 241, 42–52.
22. Wallace, M. R., Marchuk, D. A., Andersen, L. B., Letcher, R., Odeh, H. M., Saulino, A. M., Fountain, J. W., Bereton, A., Nicholson, J., Mitchell, A. L., Brownstein, B. H. and Collins, F. S. (1990) Type 1 Neurofibromatosis gene: identification of a large transcript disrupted in three NF1 patients. *Science,* 249, 181–186,
23. Elvin, P., Slynn, G., Black, D., Graham, A., Butler, R., Riley, J. Anand, R. and Markham, A. F. (1990) Isolation of cDNA clones using yeast artificial chromosome probes. *Nucleic Acids Res.* 18, 3913–3917.
24. Yokoi, T., Lovett, M., Cheng, Z. Y. and Epstein, C. J. (1986) Isolation of transcribed sequences from chromosome 21 using mouse fetal cDNA. *Hum. Genet.,* 74, 137–142.
25. Hochgeschwender, U., Sutcliffe, J. G. and Brennan, M. B. (1089). construction and screening of a genomic library specific for mouse chromosome 16. *Proc. Natl. Acad. Sci. USA,* 86, 8482–8486.
26. Duyk, G. M., Kim, S., Myers, R. M. and Cos, D. R. (1990) Exon trapping: A genetic screen to identify candidate transcribed sequences in cloned mammalian genomic DNA. *Proc. Natl, Acad. Sci. USA.,* 87, 8995–8999.
27. Hamaguchi, M., Sakamoto, H., Tsuruta, H., Muto, T., Sugimura, T. and Terada, M. (1002) Establishment of a highly sensitive and specific exon-trapping system. *Proc. Natl. Acad. Sci. USA,* 89, 9779–9783.
28. Bukler, A. J., Chang, D. D., Graw, S. L., Brook, J. D., Haber, D. A., Sharp, P; A. and Housman, D. E. (1991)

Exon amplification: a strategy to isolate mammalian genes based on RNA splicing. *Proc. Nat;. Acad. Sci. USA.,* 88, 4005–4009.
29. Bird, A. P. (1086) CpG-rich islands and the function of DNA methylation. *Nature,* 321, 209–213.
30. Lindsay, S. and Bird, A. P. (1987) Use of restriction enzymes to detect potential gene sequences in mammalian DNA. *Nature,* 327, 336–338.
31. Gardiner-Garden, M. and Frommer, M. (1087) CpG islands in vertebrate genomes. *J. Mol. Biol.,* 196, 261–282.
32. Sargent, C. A., Dunham, I. and Campbell, R. D. (1989) Identification of multiple HTF-island associated genes in the human major histocompatibility complex class III region. *EMBO J.,* 8, 2305–2312.
33. Monaco, A. P., Neve, R. L. Colletti-Feener, C., Bertelson, C. J., Kurnit, D. M. and Kunkel, L. M. (1986) Isolation of candidate cDNAs for portions of the Duchenne muscular dystrophy gene. *Nature,* 323, 646–650.
34. Riordan, J. R., Rommens, J. M., Kerem, BOS, Alon, N., Rozmahel, R., Grzelszak, Z., Zielenski, J., Lok, S., Plavsic, N., Chou, J-L., Drumm, M. L., Iannuzzi, M. C., Collins, F. S. and Tsui, L-C. (1989) Identification of the cystic fibrosis gene: cloning and characterization of complementary DNA. *Science,* 245, 1066–1073.
35. Call, K. M., Claser, T., Ito. C. Y., Buckler, A. J., Pelletier, J., Haber, D. A., Rose., E. A., Kral, A., Yeger, H., Lewis, W. H., Jones, C. and Huseman, D. E. (1990) Isolation and characterization of a zinc finger polypeptide gene at the human chromosome 11 Wilms' tumor locus. *Cell,* 60, 509–520.
36. Lovett, M., Kere, J. and Hinton, L. M. (1991) Direct selection: a method for the isolation of cDNAs encoded by large genomic regions. *Proc. Natl. Acad. Sci. USA,* 88, 9628–9632.
37. Parimoo, S., Patanjali, S. R., Shukla, H., Chaplin, D. D. and Weissman, S. M. (1991) cDNA selection: efficient PCR approach for the selection of cDNAs encoded in large chromosomal DNA fragments. *Proc. Natl. Acad. Sci. USA,* 88, 9623–9627.
38. Morgan, J. G., Doglanov, G. M., Robbins, S. E., Hinton, L. M. and Lovett, M. (1992) The selective isolation of novel cDNAs encoded by the regions surrounding the human interleukin 4 and 5 genes. *Nucleic Acids Res.,* 20, 5173–5179.
39. Tagle, D. A., Swaroop, M., Lovett, M. and Collins, F. C. (1993) Magnetic bead capture of expressed sequences encoded within large genomic segments. *Nature,* 361, 751–753.
40. Soares, M. B., Bonaldo, M. F., Jelenc, P., Su, L., Lawton, L. and Efstratiadis, A. Construction and characterization of a normalized cDNA library. *Proc. Natl. Acad. Sci. USA* (in press).
41. Bowcock, A. and Taggart, R. T. (1991) Report of the committee on the genetic constitution of chromosome 13. Cytogenet. *Cell Genet.,* 58, 580–604.
42. Benton, W. D. and Davis, R. W. (1977) Screening lambda gt recombinant clones by hybridization to single plaques. *Science,* 196, 180–182.
43. Soares, M. B. (1984) In Adams, M., Fields, C. and Craig Venter, J. (eds). Automated DNA Sequencing and Analysis Techniques. *Academic Press, pp.* 110–114.
44. Adams, M. D., Soares, M. B., Kerlavage, A. R., Fields, C. and Craig Venter, J. (1993) Rapid cDNA Sequencing (Express Sequence Tags) from a Directionally Cloned Human Infant Brain cDNA Library. *Nature Genet.,* 4, 373–380.
45. Viera, J. and Messing, J. (1987) Production of single-stranded plasmid DNA. *Methods Enzymol.,* 153, 3–11.
46. Dower, W. J., Miller, J. F. and Ragsdale, C. W. (1988) High efficiency transformation of *E.coli* by high voltage electroporation. *Nucleic Acids Res.,* 16, 6127–6145.
47. Reed, K. C. and Mann, D. A. (1985) Rapid transfer of DNA from agarose gels to nylon membranes. *Nucleic Acids Res.,* 13, 7207–7221.
48. Feinberg, A. P. and Vogelstein, B. (1983) A Technique for radiolabeling DNA restriction endoneclease fragments to high specific activity. *Anal. Biochem,* 132, 6–13.
49. Feinberg, A. P. and Vogelstein, P. (1984) A Technique for radiolabeling DNA restriction endonuclease fragments to high specific activity. Addendum. *Anal. Biochem.,* 137, 266–267.
50. Maniatis, T., Fritsch, E. F. and Sambrook, J. (1982) Molecular Cloning: A Laboratory Manual, Cold Spring Harbour.
51. Altschul, S. F., Gish, W., Miller, W., Myers, E. W. and Lipman, D. J. (1990) Basic local alignment search tool. *J. Mol, Biol.,* 215, 403–410.
52. Lee, J. J. Warburton, D. and Robertson, E. D. (1990) Cytogenetic methods in the mouse: preparation of chromosomes, karyotyping and in situ hybridization. *Anal. Biochem.,* 189, 1–17.
53. Burns, J., Chan, V. T. W., Jonasson, J. A., Fleming, K. A., Taylor, S. and McGee, J. O. D. (1985). Sensitive system for visualizing biotinylated DNA probes hybridized in situ:: rapid sex determination of intact cells. *J. Clin. Path.,* 38, 1085–1092.
54. Gosden, J. R. and Porteous, D. J. (1987) HRASI-selected chromosome mediated gene transfer, in situ hybridization with combined biotin and tritium label localizes oncogene and revels duplications of the human transfenome. Cytogenet. *Cell Genet.,* 45, 44–541.
55. Bhatt, B., Burns, J., Flannery, D. and McGee, J. O. (1988) Direct visualization of single copy genes on banded metaphase chromosomes by nonisotopic in situ hybridization. *Nucleic Acids Res.,* 16, 3951–3960.

What is claimed is:

1. A method of producing a tagged normalized directional cDNA library containing cDNA clones constructed in a vector that allows propagation in single-stranded circle form comprising:
- (a) propagating a directional cDNA library in single-stranded circles;
- (b) annealing the single-stranded circles to an appropriate primer, wherein the primer contains a specific sequence tag and performing controlled extension reaction with an appropriate polymerase in the presence of an appropriate ratio between dideoxynucleotide triphosphates and deoxynucleotide triphosphates to generate fragments complementary to the 3' noncoding sequence of the single-stranded circles in the library to produce partial duplexes;
- (c) purifying the partial duplexes;
- (d) melting and reassociating the purified partial duplexes to appropriate Cot; and
- (e) purifying unassociated single-stranded circles, thereby generating a tagged normalized directional cDNA library.

2. A normalized cDNA library generated by the method of claim 1.

3. A library of claim 2, wherein the cDNA library is derived from liver and spleen.

4. A human cDNA catalogue comprising at least two tagged normalized directional cDNA libraries generated by the method of claim 1.

5. A method to normalize the cDNA catalogue of claim 4 comprising:
- (a) propagating the directional cDNA libraries in single-stranded circles;

(b) annealing the single-stranded circles to an appropriate primer and performing controlled extension reactions with an appropriate polymerase in the presence of an appropriate ratio between dideoxynucleotide triphosphates and deoxynucleotide triphosphates to generate fragments complementary to the 3' noncoding sequence of the single-stranded circles in the libraries to produce partial duplexes;

(c) purifying the partial duplexes;

(d) melting and reassociating the purified partial duplexes to appropriate Cot; and (e) purifying the unassociated single-stranded circles, thereby generating a normalized cDNA catalogue.

6. A normalized cDNA catalogue generated by the method of claim 5.

7. A method of isolating cDNA clones specific to a tissue comprising:

(a) hybridizing single-stranded DNA circles from a normalized library of claim 2 with excess RNAs derived from other tissue; and (b) separating the unhybridized DNA circles from the hybridized DNA circles, thereby isolating cDNA clones specific to the tissue.

8. A method of claim 7, wherein the RNAs are synthesized in vitro from at least one normalized cDNA library.

9. A method of claim 7 or 8, wherein the RNAs are at least one hundred fold excess than the single-stranded DNA circles.

10. A method of claim 8, wherein the normalized libraries used are identified by being tagged with a different specific sequence.

11. A method of claim 10, further comprising inputting single-stranded DNA circles of normalized library from other tissue in step (a).

12. A method of isolating cDNA clones specific to a tissue comprising:

(a) hybridizing approximately an equal amount of single-stranded DNA circles from a tagged normalized library produced by the method of claim 1 and single-stranded DNA circles from at least one normalized tagged library of other tissue said library produced by the method of claim 1 with excess in vitro synthesized RNAs from the tagged normalized library of the other tissue;

(b) separating the hybridized DNA circles from unhybridized DNA circles;

(c) determining the specific sequence tag on the unhybridized DNA circles, an absence of the specific sequence tag of the normalized library of the other tissue indicating the completeness of the hybridization in step (a), thereby isolating cDNA clones specific to the tissue.

13. A method of identifying cDNA clones capable of hybridizing a genomic clone comprising:

(a) hybridizing the genomic clone with the single-stranded circles of a normalized cDNA library of claim 2; and (b) separating the hybridized cDNA circles from the unhybridized circles, thereby identifying cDNA clones capable of hybridizing the genomic clone.

14. A method of identifying cDNA clones capable of hybridizing a genomic clone comprising:

(a) immobilizing the genomic clone on a solid matrix;

(b) hybridizing the genomic clone with the single-stranded circles of a normalized cDNA library of claim 2;

(c) separating the hybridized cDNA circles from the unhybridized circles; and (d) eluting the hybridized cDNA circles from the solid matrix, thereby identifying cDNA clones capable of hybridizing the genomic clone.

15. A method of claim 14, where in step (c), the unhybridized circles are separated from the hybridized circles by washing the matrix with an appropriate buffer.

16. A method of identifying cDNA clones capable of hybridizing a genomic clone comprising:

(a) growing the genomic clones from a genomic library on a master plate;

(b) duplicating the genomic clones on a solid matrix such that the positions of the clones on the master plate and the matrix can be correlated;

(c) hybridizing the genomic clones on the solid matrix with the single-stranded circles of a normalized cDNA library of claim 2;

(d) washing the matrix to separate the hybridized cDNA circles from the unhybridized circles;

(e) labelling the hybridized cDNA circles of step (d) with a probe such that the position of the genomic clone on the master plate could be determined; and (f) eluting the hybridized cDNA circles from the solid matrix, thereby identifying cDNA clones capable of hybridizing the genomic clone which is determined on the master plate.

17. A method of claim 16, wherein the solid matrix is a filter.

18. A method of claim 17, wherein the probe is nucleic acid molecule capable of hybridizing to the single-strand circle and is labelled.

19. A method of claim 7, further comprising converting the isolated unhybridized DNA circles to partial duplexes by primed extension.

20. A method of claim 1, wherein the specific sequence tag is between a sequence of a rare restriction site and an oligodT stretch.

21. A method of claim 20, wherein the number of the oligodT stretch ranges from 12 to 18.

22. A method of claim 5, wherein the primer is a primer comprising an oligo(dt) stretch.

23. A method of either of claims 14 or 16, further comprising converting the eluted single-stranded DNA circles to partial duplexes by primed extension.

24. A method of any of claims 19, 20, or 21, further comprising introduction of the partial duplexes into competent host cells.

25. A method of claim 24, wherein the duplexes are introduced into the host cells by electrophoration.

* * * * *

SEQUENCE LISTING ( 1 ) GENERAL INFORMATION:

( i i i ) NUMBER OF SEQUENCES: 78

( 2 ) INFORMATION FOR SEQ ID NO:1:

( i ) SEQUENCE CHARACTERISTICS:
        ( A ) LENGTH: 8 base pairs
        ( B ) TYPE: nucleic acid ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GCGGCCGC                                                                                                              8

( 2 ) INFORMATION FOR SEQ ID NO:2:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

AAUAAA                                                                                                                6

( 2 ) INFORMATION FOR SEQ ID NO:3:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GGCCCTCGAG GCCAAGAATT CCCGACTACG TAGTCGGGGA TCCGTCTTAA TTAAGCGGCC                    60

GCAAGCTT                                                                                                              68

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AACTGGAAGA ATTCGCGGCC GCAGGAA                                                                                        27

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

GGCCGCAGGA A 11

( 2 ) INFORMATION FOR SEQ ID NO:6:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGCCGCAGGA AT 12

( 2 ) INFORMATION FOR SEQ ID NO:7:

( i ) SEQUENCE CHARACTERISTICS:
  ( A ) LENGTH: 8 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TTAATTAA 8

( 2 ) INFORMATION FOR SEQ ID NO:8:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

TTTTTTTAA TTAATTTTTT TTTTTTTTT TT 32

( 2 ) INFORMATION FOR SEQ ID NO:9:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

TTTTTTTTAA TTAAGAGTTT TTTTTTTTT TTTTT    35

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

TTTTTTTTAA TTAATAGGTT TTTTTTTTT TTTTT    35

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

TTTTTTTTAA TTAACGTCTT TTTTTTTTT TTTTT    35

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

TTTTTTTTAA TTAATGCTTT TTTTTTTTT TTTTT    35

( 2 ) INFORMATION FOR SEQ ID NO:13:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

TTTTTTTTAA TTAAAGCATT TTTTTTTTT TTTTT                                                                    35

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

TTTTTTTTAA TTAAGCTATT TTTTTTTTT TTTTT                                                                    35

( 2 ) INFORMATION FOR SEQ ID NO:15:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

TTTTTTTTAA TTAACAATTT TTTTTTTTT TTTTT                                                                    35

( 2 ) INFORMATION FOR SEQ ID NO:16:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

TTTTTTTTAA TTAACTGATT TTTTTTTTT TTTTT                                                                    35

( 2 ) INFORMATION FOR SEQ ID NO:17:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

TTTTTTTTAA TTAAAAGTT TTTTTTTTT TTTTT                                                                     35

( 2 ) INFORMATION FOR SEQ ID NO:18:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

TTTTTTTTAA TTAAACTGTT TTTTTTTTT TTTTT     35

( 2 ) INFORMATION FOR SEQ ID NO:19:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

TTTTTTTTAA TTAAATCCTT TTTTTTTTT TTTTT     35

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

TTTTTTTAA TTAACCACTT TTTTTTTTT TTTTT     35

( 2 ) INFORMATION FOR SEQ ID NO:21:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

TTTTTTTAA TTAAGGAATT TTTTTTTTT TTTTT     35

( 2 ) INFORMATION FOR SEQ ID NO:22:

( i ) SEQUENCE CHARACTERISTICS:
        ( A ) LENGTH: 8 base pairs

```
         ( B ) TYPE: nucleic acid
         ( C ) STRANDEDNESS: single
         ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:
```

G C G G C C T C                                                                                   8

( 2 ) INFORMATION FOR SEQ ID NO:23:

```
  ( i ) SEQUENCE CHARACTERISTICS:
         ( A ) LENGTH: 8 base pairs
         ( B ) TYPE: nucleic acid
         ( C ) STRANDEDNESS: single
         ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:
```

T T A A T T A A                                                                                   8

( 2 ) INFORMATION FOR SEQ ID NO:24:

```
  ( i ) SEQUENCE CHARACTERISTICS:
         ( A ) LENGTH: 16 base pairs
         ( B ) TYPE: nucleic acid
         ( C ) STRANDEDNESS: single
         ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:
```

C C G C T T A A T T   A A N N N N                                                                1 6

( 2 ) INFORMATION FOR SEQ ID NO:25:

```
  ( i ) SEQUENCE CHARACTERISTICS:
         ( A ) LENGTH: 4 base pairs
         ( B ) TYPE: nucleic acid
         ( C ) STRANDEDNESS: single
         ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:
```

C C G C                                                                                           4

( 2 ) INFORMATION FOR SEQ ID NO:26:

```
  ( i ) SEQUENCE CHARACTERISTICS:
         ( A ) LENGTH: 29 base pairs
         ( B ) TYPE: nucleic acid
         ( C ) STRANDEDNESS: single
         ( D ) TOPOLOGY: linear
```

( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

NNNNTTAATT AAGCGGCCGC AAGCTTATT 29

( 2 ) INFORMATION FOR SEQ ID NO:27:

( i ) SEQUENCE CHARACTERISTICS:
        ( A ) LENGTH: 268 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:27:

TCTGTTGAAG GAGAGGGTGA GGAAGAAGGA GAGGAATACT AAAGTTAAAA CGTCACAAAG 60

GTGCTGCTTT TACAGGGAAG CTTATTCTGT TTTAAACATT GAAAAGTTGT GGTCTGATCA 120

GTTAATTTGT ATGTAGCAGT GTATGCTCTC ATATACAATT ACTGACCTAT GCTCTAAAAC 180

ATGAATGCTT TGTTACAGAC CCAAGCTGTC CATTTCTGTG ATGGGTTTTG AATAAAGTAT 240

TCCCTGTCTT AAAAAAAAAA AAAAAAA 268

( 2 ) INFORMATION FOR SEQ ID NO:28:

( i ) SEQUENCE CHARACTERISTICS:
        ( A ) LENGTH: 232 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:28:

TCTGTTGAAG GAGAGGGTGA GGAAGAAGGA GAGGAATACT AATTATCCAT TCCTTTTGGC 60

CCTGCAGCAT GTCATGCTCC CAGAATTTCA GCTTCAGCTT AACTGACAGA TGTTAAAGCT 120

TTCTGGTTAG ATTCTTTTCA CTTGGTGATC ATGTCTTTTC CATGTGTACC TGTAATATTT 180

TTCCATCATA TCTCAAAGTA AAGTCATTAA CATCAAAAAA AAAAAAAAA AA 232

( 2 ) INFORMATION FOR SEQ ID NO:29:

( i ) SEQUENCE CHARACTERISTICS:
        ( A ) LENGTH: 1419 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:29:

TCTAGAGTTT AGTCCTTACT GTCTCACTCG TTCTGTTACC CAGGGCTCTG CAGCACCTCA 60

CCTGAGACCT CCACTCCACA TCTGCATCAC TCATGGAACA CTCATGTCTG GAGTCCCCTC 120

CTCCAGCCGC TGGCAACAAC AGCTTCAGTC CATGGGTAAT CCGTTCATAG AAATTGTGTT 180

TGCTAACAAG GTGCCCTTTA GCCAGATGCT AGGCTGTCTG CGAAGAAGGC TAGGAGTTCA 240

TAGAAGGGAG TGGGCTGGG GAAAGGGCTG GCTGCAATTG CAGCTCACTG CTGCTGCCTC 300

TGAAACAGAA AGTTGGAAAG GAAAAAAGAA AAAAGCAATT AGGTAGCACA GCACTTTGGT 360

TTTGCTGAGA TCGAAGAGGC CAGTAGGAGA CACGACAGCA CACACAGTGG ATTCCAGTGC 420

```
ATGGGAGGC  ACTCGCTGTT  ATCAAATAGC  GATGTGCAGG  AAGAAAAGCC  CCTCTTCATT    480

CCGGGGAACA  AAGACGGGTA  TTGTTGGGAA  AGGAACAGGC  TTGGAGGGAA  GGGAGAAAGT    540

AGGCCGCTGA  TGATATATTC  GGGCAGGACT  GTTGTGGTAC  TGGCAATAAG  ATACACAGCT    600

CCGAGCTGTA  GGAGAGTCGG  TCTGCTTTGG  ATGATTTTTT  AAGCAGACTC  AGCTGCTATA    660

CTTATCACAT  TTTATTAAAC  ACAGGGAAAG  CATTTAGGAG  AATAGCAGAG  AGCCAAATCT    720

GACCTAAAAG  TTGAAAAGCC  AAAGGTCAAA  CAGGCTGTAA  TTCCATCATC  ATCGTTGTTA    780

TTAAAGAATC  CTTATCTATA  AAAGGTAGGT  CAGATCCCCC  TCCCCCCAGG  TTCCTCCTTC    840

CCCTCCCGAT  TGAGCCTTAC  GACACTTTGG  TTTATGCGGT  GCTGTCCGGG  TGCCAGGGCT    900

GCAGGGTCGG  TACTGATGGA  GCCTGCAGCG  CCCGGTGCTC  TGTGTCAAGG  TGAAGCACAT    960

ACGGCAGACC  TCTTAGAGTC  CTTAAGACGG  AAGTAAATTA  TGATGTCCAG  GGGGAGAAGG   1020

AAGATAGGAC  GTATTTATAA  TAGGTATATA  GAACACAAGG  GATATAAAAT  GAAAGATTTT   1080

TACTAATATA  TATTTTAAGG  TTGCACACAG  TACACACCAG  AAGATGTGAA  ATTCATTTGT   1140

GGCAATTAAG  TGGTCCCAAT  GCTCAGCGCT  TAAAAAAACA  AATTGGACAG  CTACTTCTGG   1200

GAAAAACAAC  ATCATTCCAA  AAAGAACAAT  AATGAGAGCA  AATGCAAAAA  TAACCAAGTC   1260

CTCCGAAGGC  ATCTCACGGA  ACCGTAGACT  AGGAAGTACG  AGCCCACAG   AGCAGGAAGC   1320

CGATGTGACT  GCATCATATA  TTTAACAATG  ACAAGATGTT  CCGGCGTTTA  TTTCTGCGTT   1380

GGGTTTTCCC  TTGCCTTATG  GGCTGAAGTG  TTCTCTAGA                            1419
```

( 2 ) INFORMATION FOR SEQ ID NO:30:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:30:

```
TCTAGAGTTT  AGTCCTTACT  GTCTCACTCG  TTCTGTTACC  CAGGGCTCTG  CAGCACCTCA     60

CCTGAGACCT  CCACTCCACA  TCTGCATCAC  TCATGGAACA  CTCATGTCTG  GAGTCCCCTC    120

CTCCAGCCGC  TGGCAACAAC  AGCTTCAGTC  CATGGGTAAT  CCGTTCATAG  AAATTGTGTT    180

TGCTAACAAG  GTGCCCTTTA  GCCAGATGCT  AGGCTGTCTG  CGAAGAAGGC  TAGGAGTTCA    240

TAGAAGGGAG  TGGGGCTGGG  GAAAGGGCTG  GCTGCAATTG  CAGCTCACTG  CTGCTGCCTC    300

TGAAACAGAA  AGTTGGAAAG  GAAAAAAAAA  AAAAAAAA                              339
```

( 2 ) INFORMATION FOR SEQ ID NO:31:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:31:

```
TACTTCTGGG  AAAAACAACA  TCATTCCAAA  AAGAACAATA  ATGAGAGCAA  ATGCAAAAAT     60

AACCAAGTCC  TCCGAAGGCA  TCTCACGGAA  CCGTAGACTA  GGAAGTACGA  GCCCACAGA    120

GCAGGAAGCC  GATGTGACTG  CATCATATAT  TTAACAATGA  CAAGATGTTC  CGGCGTTTAT    180

TTCTGCGTTG  GGTTTTCCCT  TGCCTTATGG  GCTGAAGTGT  TCTCTAGA                  228
```

( 2 ) INFORMATION FOR SEQ ID NO:32:

( i ) SEQUENCE CHARACTERISTICS:
           ( A ) LENGTH: 254 base pairs
           ( B ) TYPE: nucleic acid
           ( C ) STRANDEDNESS: single
           ( D ) TOPOLOGY: linear ( i i ) MOLECULE TYPE: other nucleic acid ( x i ) SEQUENCE DESCRIPTION: SEQ ID NO:32:

```
TTGTCTTTTG ATCTTTTATT TCTGAAACAC TCAAACACCT TACAAAGTGC TGAGTAGGTA        60
ATAGTGACCC AACTTGTTTG CTAAATGATT ATTTGTTTAA ATCTGTACAG TTTTAAGTGT       120
TCACTTATAC AAAGAGTGTA TATACTTTCA AATAATTTAA AATGCTTTAT ATTATGGCTA       180
GAAATTGCTG TTTTTAATAA ATGTGAATTT TTTAAAAATA AAGATTTTTG CTTCCTAAAA       240
AAAAAAAAAA AAAA                                                         254
```

( 2 ) INFORMATION FOR SEQ ID NO:33:

( i ) SEQUENCE CHARACTERISTICS:
           ( A ) LENGTH: 239 base pairs
           ( B ) TYPE: nucleic acid
           ( C ) STRANDEDNESS: single
           ( D ) TOPOLOGY: linear ( i i ) MOLECULE TYPE: other nucleic acid ( x i ) SEQUENCE DESCRIPTION: SEQ ID NO:33:

```
TTGTCTTTTG ATCTTTTATT TCTGAAACAC TCAAACACCT TACAAAGTGC TGAGTAGGTA        60
ATAGTGACCC AACTTGTTTG CTAAATGATT ATTTGTTTAA ATCTGTACAG TTTTAAGTGT       120
TCACTTATAC AAAGAGTGTA TATACTTTCA AATAATTTAA AATGCTTTAT ATTATTTGGC       180
TAGAAATTGC TGTTTTTAAT AAATGTGAAT TTTTTAAAAA TAAAAAAAAA AAAAAAAA         239
```

( 2 ) INFORMATION FOR SEQ ID NO:34:

( i ) SEQUENCE CHARACTERISTICS:
           ( A ) LENGTH: 324 base pairs
           ( B ) TYPE: nucleic acid
           ( C ) STRANDEDNESS: single
           ( D ) TOPOLOGY: linear ( i i ) MOLECULE TYPE: peptide ( i x ) FEATURE:
           ( A ) NAME/KEY: CDS
           ( B ) LOCATION: 12..311

( x i ) SEQUENCE DESCRIPTION: SEQ ID NO:34:

```
TTCTCCGGCA G GTG  GGC  ATT  AAC  TAC  CAG  CCC  CCC  ACG  GTG  GTC  CCT  GGG         50
              Val  Gly  Ile  Asn  Tyr  Gln  Pro  Pro  Thr  Val  Val  Pro  Gly
               1              5                        10

GGA  GAC  CTG  GCC  AAG  GTG  CAG  CGG  GCT  GTG  TGC  ATG  CTG  AGC  AAC  ACC       98
Gly  Asp  Leu  Ala  Lys  Val  Gln  Arg  Ala  Val  Cys  Met  Leu  Ser  Asn  Thr
     15                  20                      25

ACG  GCC  ATC  GCG  GAG  GCC  TGG  GCT  CGC  CTG  GAC  CAT  AAG  TTC  GAT  CTC      146
Thr  Ala  Ile  Ala  Glu  Ala  Trp  Ala  Arg  Leu  Asp  His  Lys  Phe  Asp  Leu
30            Ile            35                      40                       45

ATG  TAT  GCC  AAG  CGG  GCC  TTT  GTG  CAC  TGG  TAC  GTG  GGA  GAA  GGC  ATG      194
Met  Tyr  Ala  Lys  Arg  Ala  Phe  Val  His  Trp  Tyr  Val  Gly  Glu  Gly  Met
                    50                      55                       60

GAG  GAG  GGG  GAG  TTC  TCT  GAG  GCC  CGC  GAG  GAC  CTG  GCA  GCT  CTG  GAG      242
Glu  Glu  Gly  Glu  Phe  Ser  Glu  Ala  Arg  Glu  Asp  Leu  Ala  Ala  Leu  Glu
```

|   |   |   |   |   | 65 |   |   |   |   | 70 |   |   |   |   | 75 |   |   |   |   |
|---|---|---|---|---|---|---|---|---|---|---|---|---|---|---|---|---|---|---|---|

AAG GAT TAT GAA GAG GTG GGC GTG GAT TCC GTG GAA GCC GAG GCT GAA    290
Lys Asp Tyr Glu Glu Val Gly Val Asp Ser Val Glu Ala Glu Ala Glu
         80                    85                    90

GAA GGT GAA GAA GAA GAA TAC TGAGGGGAGG GTG    324
Glu Gly Glu Glu Glu Glu Tyr
     95                  100

( 2 ) INFORMATION FOR SEQ ID NO:35:

( i ) SEQUENCE CHARACTERISTICS:
       ( A ) LENGTH: 100 amino acids
       ( B ) TYPE: amino acid
       ( D ) TOPOLOGY: linear ( i i ) MOLECULE TYPE: protein ( x i ) SEQUENCE DESCRIPTION: SEQ ID NO:35:

Val Gly Ile Asn Tyr Gln Pro Pro Thr Val Val Pro Gly Gly Asp Leu
 1               5                  10                  15

Ala Lys Val Gln Arg Ala Val Cys Met Leu Ser Asn Thr Thr Ala Ile
             20                  25                  30

Ala Glu Ala Trp Ala Arg Leu Asp His Lys Phe Asp Leu Met Tyr Ala
         35                  40                  45

Lys Arg Ala Phe Val His Trp Tyr Val Gly Glu Gly Met Glu Glu Gly
     50                  55                  60

Glu Phe Ser Glu Ala Arg Glu Asp Leu Ala Ala Leu Glu Lys Asp Tyr
 65                  70                  75                  80

Glu Glu Val Gly Val Asp Ser Val Glu Ala Glu Ala Glu Glu Gly Glu
                 85                  90                  95

Glu Glu Glu Tyr
            100

( 2 ) INFORMATION FOR SEQ ID NO:36:

( i ) SEQUENCE CHARACTERISTICS:
       ( A ) LENGTH: 318 base pairs
       ( B ) TYPE: nucleic acid
       ( C ) STRANDEDNESS: single
       ( D ) TOPOLOGY: linear ( i i ) MOLECULE TYPE: peptide ( x i ) SEQUENCE DESCRIPTION: SEQ ID NO:36:

TTCTCTGGCA GGTGGGCATT AACTACCAGC CCCCCACAGT GGTCCCCGGG GGAGACCTGG    60

CCAAGGTGCA GCGGGCCGTG TGCATGCTGA GCAACACCAC GGCCATTGCG GAGGCCTGGG    120

CCCGCCTGGA CCACAAGTTC GATCTCATGT ATGCCAAGCG TGCCTTTGTG CACTGGTACG    180

TGGGCGAAGG CATGGAAGAG GGAGAGTTCT CTGAGGCCCG CGAGGACCTG GCAGCTCTAG    240

AGAAGGATTA TGAAGAGGTG GGCGTGGATT CCGTGGAAGC TGAGGCTGAA GAAGGCGAAG    300

AATACTGAGG GGAGGGTG    318

( 2 ) INFORMATION FOR SEQ ID NO:37:

( i ) SEQUENCE CHARACTERISTICS:
       ( A ) LENGTH: 323 base pairs
       ( B ) TYPE: nucleic acid
       ( C ) STRANDEDNESS: single
       ( D ) TOPOLOGY: linear ( i i ) MOLECULE TYPE: other nucleic acid ( i x ) FEATURE:

( A ) NAME/KEY: CDS
( B ) LOCATION: 1..309

( x i ) SEQUENCE DESCRIPTION: SEQ ID NO:37:

| TGC | CCC | ACA | GGC | TTC | AAG | GTT | GGT | ATC | AAC | TAC | CAG | CCT | CCC | ACT | GTG | 48 |
| Cys | Pro | Thr | Gly | Phe | Lys | Val | Gly | Ile | Asn | Tyr | Gln | Pro | Pro | Thr | Val | |
| | | | | 105 | | | | | 110 | | | | | 115 | | |
| GTG | CCT | GGG | GGT | GAC | CTG | GCC | AAG | GTG | CAG | CGT | GCC | GTG | TGC | ATG | CTG | 96 |
| Val | Pro | Gly | Gly | Asp | Leu | Ala | Lys | Val | Gln | Arg | Ala | Val | Cys | Met | Leu | |
| | | | 120 | | | | | 125 | | | | | 130 | | | |
| AGC | AAC | ACG | ACC | GCC | ATC | GCC | GAG | GCC | TGG | GCC | CGC | CTG | GAC | CAC | AAG | 144 |
| Ser | Asn | Thr | Thr | Ala | Ile | Ala | Glu | Ala | Trp | Ala | Arg | Leu | Asp | His | Lys | |
| | | 135 | | | | | 140 | | | | | 145 | | | | |
| TTC | GAC | CTG | ATG | TAT | GCC | AAG | AGG | GCG | TTT | GTG | CAC | TGG | TAT | GTG | GGT | 192 |
| Phe | Asp | Leu | Met | Tyr | Ala | Lys | Arg | Ala | Phe | Val | His | Trp | Tyr | Val | Gly | |
| | 150 | | | | | 155 | | | | | 160 | | | | | |
| GAG | GGC | ATG | GAG | GAG | GGT | GAG | TTC | TCC | GAG | GCC | CGT | GAG | GAT | ATG | GCT | 240 |
| Glu | Gly | Met | Glu | Glu | Gly | Glu | Phe | Ser | Glu | Ala | Arg | Glu | Asp | Met | Ala | |
| 165 | | | | | 170 | | | | | 175 | | | | | 180 | |
| GCC | CTG | GAG | AAG | GAT | TAT | GAG | GAG | GTG | GGC | ATC | GAC | TCC | TAT | GAG | GAC | 288 |
| Ala | Leu | Glu | Lys | Asp | Tyr | Glu | Glu | Val | Gly | Ile | Asp | Ser | Tyr | Glu | Asp | |
| | | | | 185 | | | | | 190 | | | | | 195 | | |
| GAG | GAT | GAG | GGA | GAA | GAA | TAC | TAAAGCAGCT | | GCCT | | | | | | | 323 |
| Glu | Asp | Glu | Gly | Glu | Glu | Tyr | | | | | | | | | | |
| | | | 200 | | | | | | | | | | | | | |

( 2 ) INFORMATION FOR SEQ ID NO:38:

( i ) SEQUENCE CHARACTERISTICS:
( A ) LENGTH: 103 amino acids
( B ) TYPE: amino acid
( D ) TOPOLOGY: linear ( i i ) MOLECULE TYPE: protein ( x i ) SEQUENCE DESCRIPTION: SEQ ID NO:38:

| Cys | Pro | Thr | Gly | Phe | Lys | Val | Gly | Ile | Asn | Tyr | Gln | Pro | Pro | Thr | Val |
| 1 | | | | 5 | | | | | 10 | | | | | 15 | |
| Val | Pro | Gly | Gly | Asp | Leu | Ala | Lys | Val | Gln | Arg | Ala | Val | Cys | Met | Leu |
| | | | 20 | | | | | 25 | | | | | 30 | | |
| Ser | Asn | Thr | Thr | Ala | Ile | Ala | Glu | Ala | Trp | Ala | Arg | Leu | Asp | His | Lys |
| | | 35 | | | | | 40 | | | | | 45 | | | |
| Phe | Asp | Leu | Met | Tyr | Ala | Lys | Arg | Ala | Phe | Val | His | Trp | Tyr | Val | Gly |
| | 50 | | | | | 55 | | | | | 60 | | | | |
| Glu | Gly | Met | Glu | Glu | Gly | Glu | Phe | Ser | Glu | Ala | Arg | Glu | Asp | Met | Ala |
| 65 | | | | | 70 | | | | | 75 | | | | | 80 |
| Ala | Leu | Glu | Lys | Asp | Tyr | Glu | Glu | Val | Gly | Ile | Asp | Ser | Tyr | Glu | Asp |
| | | | | 85 | | | | | 90 | | | | | 95 | |
| Glu | Asp | Glu | Gly | Glu | Glu | Tyr | | | | | | | | | |
| | | | 100 | | | | | | | | | | | | |

( 2 ) INFORMATION FOR SEQ ID NO:39:

( i ) SEQUENCE CHARACTERISTICS:
( A ) LENGTH: 57 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:39:

| Ile | Lys | Tyr | Met | Glu | Lys | His | Lys | Val | Lys | Pro | Asp | Ser | Lys | Ala | Phe |

|  | 1 |  |  |  | 5 |  |  |  |  | 10 |  |  |  |  | 15 |
|---|---|---|---|---|---|---|---|---|---|---|---|---|---|---|---|
|  | His | Leu | Leu | Gln | Lys | Leu | Leu | Thr | Met | Asp | Pro | Ile | Lys | Arg | Ile | Thr |
|  |  |  |  | 20 |  |  |  |  | 25 |  |  |  |  | 30 |
|  | Ser | Glu | Gln | Ala | Met | Gln | Asp | Pro | Tyr | Phe | Leu | Glu | Asp | Pro | Leu | Pro |
|  |  |  | 35 |  |  |  |  | 40 |  |  |  |  | 45 |
|  | Thr | Ser | Asp | Val | Phe | Gly | Gly | Cys | Gln |
|  |  |  | 50 |  |  |  | 55 |

( 2 ) INFORMATION FOR SEQ ID NO:40:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

Asp Ser Lys Ala
1

( 2 ) INFORMATION FOR SEQ ID NO:41:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

Lys Arg Ile Thr
1

( 2 ) INFORMATION FOR SEQ ID NO:42:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

Glu Asp Pro Leu Pro
1              5

( 2 ) INFORMATION FOR SEQ ID NO:43:

( i ) SEQUENCE CHARACTERISTICS:
        ( A ) LENGTH: 846 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: CDS
        ( B ) LOCATION: 1..528

( x i ) SEQUENCE DESCRIPTION: SEQ ID NO:43:

| ACC | AAC | TGC | AGC | CTT | ATC | AAG | TAT | ATG | GAA | AAA | CAT | AAA | GTT | AAA | CCA | 48 |
| Thr | Asn | Cys | Ser | Leu | Ile | Lys | Tyr | Met | Glu | Lys | His | Lys | Val | Lys | Pro |  |
| 105 |  |  |  |  | 110 |  |  |  |  | 115 |

| | | | | | | | | | | | | | | | | |
|---|---|---|---|---|---|---|---|---|---|---|---|---|---|---|---|---|
| GAT | AGT | AAA | GCA | TTC | CAC | TTG | CTT | CAG | AAG | CTG | CTT | ACC | ATG | GAC | CCA | 96 |
| Asp | Ser | Lys | Ala | Phe | His | Leu | Leu | Gln | Lys | Leu | Leu | Thr | Met | Asp | Pro | |
| 120 | | | | | 125 | | | | | 130 | | | | | 135 | |
| ATA | AAG | CGA | ATT | ACC | TCA | GAA | CAG | GCT | ATG | CAG | GAC | CCC | TAT | TTC | TTA | 144 |
| Ile | Lys | Arg | Ile | Thr | Ser | Glu | Gln | Ala | Met | Gln | Asp | Pro | Tyr | Phe | Leu | |
| | | | | 140 | | | | | 145 | | | | | 150 | | |
| GAA | GAC | CCA | CTT | CCT | ACA | TCA | GAC | GTT | TTT | GGC | GGT | TGT | CAA | ATC | CCT | 192 |
| Glu | Asp | Pro | Leu | Pro | Thr | Ser | Asp | Val | Phe | Gly | Gly | Cys | Gln | Ile | Pro | |
| | | | 155 | | | | | 160 | | | | | 165 | | | |
| TAC | CCA | AAA | CGA | GAA | TTT | TTA | ACG | GAA | GAA | GAA | CCT | GAT | GAC | AAA | GGA | 240 |
| Tyr | Pro | Lys | Arg | Glu | Phe | Leu | Thr | Glu | Glu | Glu | Pro | Asp | Asp | Lys | Gly | |
| | | 170 | | | | | 175 | | | | | 180 | | | | |
| GAC | AAA | AAG | AAC | CAG | CAG | CAG | CAG | CAG | GGC | AAT | AAC | CAC | ACT | AAT | GGA | 288 |
| Asp | Lys | Lys | Asn | Gln | Gln | Gln | Gln | Gln | Gly | Asn | Asn | His | Thr | Asn | Gly | |
| | 185 | | | | | 190 | | | | | 195 | | | | | |
| ACT | GGC | CAC | CCA | GGG | AAT | CAA | GAC | AGC | AGT | CAC | ACA | CAG | GGA | CCC | CCG | 336 |
| Thr | Gly | His | Pro | Gly | Asn | Gln | Asp | Ser | Ser | His | Thr | Gln | Gly | Pro | Pro | |
| 200 | | | | | 205 | | | | | 210 | | | | | 215 | |
| TTG | AAG | AAA | GTG | AGA | GTT | GTT | CCT | CCT | ACC | ACT | ACC | TCA | GGT | GGA | CTT | 384 |
| Leu | Lys | Lys | Val | Arg | Val | Val | Pro | Pro | Thr | Thr | Thr | Ser | Gly | Gly | Leu | |
| | | | | 220 | | | | | 225 | | | | | 230 | | |
| ATC | ATG | ACC | TCA | GAC | TAT | CAG | CGT | TCC | AAT | CCA | CAT | GCT | GCC | TAT | CCC | 432 |
| Ile | Met | Thr | Ser | Asp | Tyr | Gln | Arg | Ser | Asn | Pro | His | Ala | Ala | Tyr | Pro | |
| | | | 235 | | | | | 240 | | | | | 245 | | | |
| AAC | CCT | GGA | CCA | AGC | ACA | TCA | CAG | CCG | CAG | AGC | AGC | ATG | GGA | TAC | TCA | 480 |
| Asn | Pro | Gly | Pro | Ser | Thr | Ser | Gln | Pro | Gln | Ser | Ser | Met | Gly | Tyr | Ser | |
| | | 250 | | | | | 255 | | | | | 260 | | | | |
| GCT | ACC | TCC | CAG | CAG | CCT | CCA | CAG | TAC | TCA | CAT | CAG | ACA | CAT | CGG | TAC | 528 |
| Ala | Thr | Ser | Gln | Gln | Pro | Pro | Gln | Tyr | Ser | His | Gln | Thr | His | Arg | Tyr | |
| | | 265 | | | | | 270 | | | | | 275 | | | | |

| | | | | |
|---|---|---|---|---|
| TGAGCTGCAT | CGGAATCTTG | TCCATGCACT | GTTGCGAATG | CTGCAGGGCT | GACTGTGCAG | 588 |
| CTCTCTGCGG | GAACCTGGTA | TGGGCCATGA | GAATGTACTG | TACAACCACA | TCTTCAAAAT | 648 |
| GTCCAGTAGC | CAAGTTCCAC | CACTTTTCAC | AGATTGGGGT | AGTGGCTTCC | AAGTTGTACC | 708 |
| TATTTTGGAG | TTAGACTTGA | AAAGAAAGTG | CTAGCACAGT | TTGTGTTGTG | GATTTGCTAC | 768 |
| TTCCATAGTT | TACTTGACAT | GGTTCAGACT | GACCTATGCA | TTTTTTTCAG | TGACAGTCTG | 828 |
| TAGCAGTTGA | AGCTGTGA | | | | | 846 |

( 2 ) INFORMATION FOR SEQ ID NO:44:

( i ) SEQUENCE CHARACTERISTICS:
        ( A ) LENGTH: 176 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

| | | | | | | | | | | | | | | | |
|---|---|---|---|---|---|---|---|---|---|---|---|---|---|---|---|
| Thr | Asn | Cys | Ser | Leu | Ile | Lys | Tyr | Met | Glu | Lys | His | Lys | Val | Lys | Pro |
| 1 | | | | 5 | | | | | 10 | | | | | 15 | |
| Asp | Ser | Lys | Ala | Phe | His | Leu | Leu | Gln | Lys | Leu | Leu | Thr | Met | Asp | Pro |
| | | | 20 | | | | | 25 | | | | | 30 | | |
| Ile | Lys | Arg | Ile | Thr | Ser | Glu | Gln | Ala | Met | Gln | Asp | Pro | Tyr | Phe | Leu |
| | | | 35 | | | | | 40 | | | | | 45 | | |
| Glu | Asp | Pro | Leu | Pro | Thr | Ser | Asp | Val | Phe | Gly | Gly | Cys | Gln | Ile | Pro |
| | | 50 | | | | | 55 | | | | | 60 | | | |
| Tyr | Pro | Lys | Arg | Glu | Phe | Leu | Thr | Glu | Glu | Glu | Pro | Asp | Asp | Lys | Gly |
| 65 | | | | | 70 | | | | | 75 | | | | | 80 |
| Asp | Lys | Lys | Asn | Gln | Gln | Gln | Gln | Gln | Gly | Asn | Asn | His | Thr | Asn | Gly |

|     |     |     |     |     | 85  |     |     |     |     | 90  |     |     |     |     | 95  |
| --- | --- | --- | --- | --- | --- | --- | --- | --- | --- | --- | --- | --- | --- | --- | --- |

Thr Gly His Pro Gly Asn Gln Asp Ser Ser His Thr Gln Gly Pro Pro
            100                 105                 110

Leu Lys Lys Val Arg Val Val Pro Pro Thr Thr Thr Ser Gly Gly Leu
        115                 120                 125

Ile Met Thr Ser Asp Tyr Gln Arg Ser Asn Pro His Ala Ala Tyr Pro
    130                 135                 140

Asn Pro Gly Pro Ser Thr Ser Gln Pro Gln Ser Ser Met Gly Tyr Ser
145                 150                 155                 160

Ala Thr Ser Gln Gln Pro Pro Gln Tyr Ser His Gln Thr His Arg Tyr
                165                 170                 175

( 2 ) INFORMATION FOR SEQ ID NO:45:

( i ) SEQUENCE CHARACTERISTICS:
        ( A ) LENGTH: 474 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:45:

```
GATCAGCGTT  TTTGGCGGTT  GTCAAATCCC  TTACCCAAAA  CGAGAATTTT  TAACGGAAGA      60

AGAACCTGAT  GACAAAGGAG  ACAAAGTAAG  TATTAAAGTA  CTGTTAGCAG  CTTCTTGTTT     120

CGTGAATGCC  TCCATAACAT  TTTCCATTGT  GGGTATATTT  TGTTCTCCCT  CTGAGCTGAA     180

CTTTTTCTGT  TTAACCAATT  GAGAAGAACC  AGCAGCAGCA  GCAGGGCAAT  AACCACACTA     240

ATGGAACTGG  CCACCCAGGG  AATCAAGACA  GCAGTCACAC  ACAGGGACCC  CCGTTGAAGA     300

AAGTGAGAGT  TGTTCCTCCT  ACCACTACCT  CAGGTGGACT  TATCATGACC  TCAGACTATC     360

AGGTATTCCA  AGTTTATTTT  GGGTTGGACT  GCATGTCAGN  GTTTACATAT  GGGTTTATGA     420

TCCGGGGGAA  AATGTGATTT  AATTGAGAAC  TGCATGTCAG  NNGTTTACAT  ATGG           474
```

( 2 ) INFORMATION FOR SEQ ID NO:46:

( i ) SEQUENCE CHARACTERISTICS:
        ( A ) LENGTH: 578 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:46:

```
GATCCGGGGG  AAAATGTGAT  TTAATTGAGC  CTATACATCC  TTTCTTCGTT  GAAACATAAT      60

GACACATCAG  TCACATATTG  GGATTGAGCT  TCCCCTAGAA  GCANCTGAAT  CACACTTTTC     120

CCTCATCTCC  TTTCCAGCGT  NCCAATCNAC  ATGCTGCCTA  TCCCAACCCT  GGACCAAGCA     180

CATCACAGCC  GCAGAGCAGC  ATGGATACT   CAGCTACCTC  CCAGCAGCCT  CCACAGTACT     240

CACATCAGAC  ACATCGGTAC  TGAGCTGCAT  CGGAATCTTG  TCCATGCACT  GTTGCAATN      300

CTGCAGGGCT  GACTGTGCAG  CTCTCTGCGG  GAACCTGGTA  TGGGCCATGA  GAATGTACTG     360

TACAACCACA  TCTTCAAAAT  GTCCAGTAGC  CAAGTTCCAC  CACTTTTCAC  AGATTGGGGT     420

AGTGGCTTCC  AAGTTGTACC  TATTTTGGAG  TTAGACTTGA  AAAGAAAGTG  CTAGCACAGT     480

TTGTGTTGTG  GATTTGCTAC  TTCCATAGTT  TACTTGACAT  GGTTCAGACT  GACCAATGCA     540

TTTTTTTCAG  TGACAGTCTG  TAGCAGTTGA  AGCTGTGA                              578
```

( 2 ) INFORMATION FOR SEQ ID NO:47:

( i ) SEQUENCE CHARACTERISTICS:
           ( A ) LENGTH: 28 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:47:

AACTGGAAGA ATTCGCGGCC GCAGGAAT                              28

( 2 ) INFORMATION FOR SEQ ID NO:48:

( i ) SEQUENCE CHARACTERISTICS:
           ( A ) LENGTH: 11 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:48:

GGCCGCAGGA A                                                11

( 2 ) INFORMATION FOR SEQ ID NO:49:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:49:

AAGCAGGTTC TTGTTGGTGC                                    20

( 2 ) INFORMATION FOR SEQ ID NO:50:

( i ) SEQUENCE CHARACTERISTICS:
           ( A ) LENGTH: 22 base pairs
           ( B ) TYPE: nucleic acid
           ( C ) STRANDEDNESS: single
           ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:50:

AGAATGTCAA CAAAACAGCT GC                                 22

( 2 ) INFORMATION FOR SEQ ID NO:51:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:51:

ACCCCCCTGT ACACAACTCA                                    20

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:52:

TGCAAAATAC CACCAGGACA        20

( 2 ) INFORMATION FOR SEQ ID NO:53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:53:

AAGGTGCAGC GGGCT        15

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:54:

CTTCACCTTC TTCAGCCTCG        20

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:55:

CAGTACCCTC TCTCCATTTT CA        22

( 2 ) INFORMATION FOR SEQ ID NO:56:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:56:

GACAGAGTAT CCCCTTGAGG G                                                                                          21

( 2 ) INFORMATION FOR SEQ ID NO:57:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:57:

CTGTTTGTTT CAATTGGCCA                                                                                            20

( 2 ) INFORMATION FOR SEQ ID NO:58:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:58:

AAATTCTGGG ACAAATTTTT GG                                                                                         22

( 2 ) INFORMATION FOR SEQ ID NO:59:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:59:

CCTCCAAGGA GTAAGACCCC                                                                                            20

( 2 ) INFORMATION FOR SEQ ID NO:60:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:60:

GGTACATGAC AAGGTGCGG                                                                                             19

( 2 ) INFORMATION FOR SEQ ID NO:61:

( i ) SEQUENCE CHARACTERISTICS:
    ( A ) LENGTH: 20 base pairs
    ( B ) TYPE: nucleic acid
    ( C ) STRANDEDNESS: single ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:61:

TCCATGGGTA ATCCGTTCAT                                           20

( 2 ) INFORMATION FOR SEQ ID NO:62:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:62:

ACCCAACGCA GAAATAAACG                                           20

( 2 ) INFORMATION FOR SEQ ID NO:63:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:63:

TTTCTTCAGC AAGCCTCTTT T                                         21

( 2 ) INFORMATION FOR SEQ ID NO:64:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:64:

TTCCCCCTT TTGAAAGC                                              18

( 2 ) INFORMATION FOR SEQ ID NO:65:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:65:

AAATATTTTC GTCCTGATTT TAAAGC                                    26

( 2 ) INFORMATION FOR SEQ ID NO:66:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:66:

CCTCAAAAAT TCTAAGGCTC TCC     23

( 2 ) INFORMATION FOR SEQ ID NO:67:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:67:

TCTTAGAAGC CCACTTCCTA CATC     24

( 2 ) INFORMATION FOR SEQ ID NO:68:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:68:

TTTTGGGTAA GGGATTTGAC A     21

( 2 ) INFORMATION FOR SEQ ID NO:69:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:69:

CCCAGTGCAG AAATCAGGAT     20

( 2 ) INFORMATION FOR SEQ ID NO:70:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:70:

AAAATCAGAA TCGCTTCCCA 20

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:71:

TCCTTCTCAA ACTGCAAAAG G 21

( 2 ) INFORMATION FOR SEQ ID NO:72:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:72:

GAGCTCCAAA CTGAATGGGT 20

( 2 ) INFORMATION FOR SEQ ID NO:73:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:73:

CATTTGTTCC CACTGCCTTT 20

( 2 ) INFORMATION FOR SEQ ID NO:74:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:74:

TTCTGCAAAC CACAATATGT CA 22

( 2 ) INFORMATION FOR SEQ ID NO:75:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear -continued (i i) MOLECULE TYPE: DNA (genomic)

(i v) ANTI-SENSE: NO (x i) SEQUENCE DESCRIPTION: SEQ ID NO:75:

ACACCTTACA AAGTGCTGAG TAGG 24

(2) INFORMATION FOR SEQ ID NO:76:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (i i) MOLECULE TYPE: DNA (genomic)

(i v) ANTI-SENSE: YES (x i) SEQUENCE DESCRIPTION: SEQ ID NO:76:

TTAAAAACAG CAATTTCTAG CCATA 25

(2) INFORMATION FOR SEQ ID NO:77:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (i i) MOLECULE TYPE: DNA (genomic)

(i v) ANTI-SENSE: NO (x i) SEQUENCE DESCRIPTION: SEQ ID NO:77:

ACACCTTACA AAGTGCTGAG TAGG 24

(2) INFORMATION FOR SEQ ID NO:78:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (i i) MOLECULE TYPE: DNA (genomic)

(i v) ANTI-SENSE: YES (x i) SEQUENCE DESCRIPTION: SEQ ID NO:78:

AAAAACAGCA ATTTCTAGCC AAAT 24